US008119336B2

(12) United States Patent
Sampath et al.

(10) Patent No.: US 8,119,336 B2
(45) Date of Patent: Feb. 21, 2012

(54) COMPOSITIONS FOR USE IN IDENTIFICATION OF ALPHAVIRUSES

(75) Inventors: Rangarajan Sampath, San Diego, CA (US); Thomas A. Hall, Oceanside, CA (US); Mark W. Eshoo, Solana Beach, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 1134 days.

(21) Appl. No.: 11/070,632

(22) Filed: Mar. 2, 2005

(65) Prior Publication Data

US 2010/0035227 A1 Feb. 11, 2010

Related U.S. Application Data

(60) Provisional application No. 60/550,023, filed on Mar. 3, 2004.

(51) Int. Cl.
*C12Q 1/70* (2006.01)

(52) U.S. Cl. ........................................ 435/5; 536/24.33

(58) Field of Classification Search ........................ None
See application file for complete search history.

(56) References Cited

U.S. PATENT DOCUMENTS 4,075,475 A 2/1978 Risby et al.
4,683,195 A 7/1987 Mullis et al.
4,683,202 A 7/1987 Mullis et al.
4,965,188 A 10/1990 Mullis et al.
5,015,845 A 5/1991 Allen et al.
5,072,115 A 12/1991 Zhou
5,143,905 A 9/1992 Sivasubramanian et al.
5,213,961 A 5/1993 Bunn et al.
5,219,727 A 6/1993 Wang et al.
5,288,611 A 2/1994 Kohne
5,436,129 A 7/1995 Stapleton
5,451,500 A 9/1995 Stapleton
5,472,843 A 12/1995 Milliman
5,476,774 A 12/1995 Wang et al.
5,484,908 A 1/1996 Froehler et al.
5,502,177 A 3/1996 Matteucci et al.
5,503,980 A 4/1996 Cantor et al.
5,504,327 A 4/1996 Sproch et al.
5,504,329 A 4/1996 Mann et al.
5,523,217 A 6/1996 Lupski et al.
5,527,669 A 6/1996 Resnick et al.
5,527,675 A 6/1996 Coull et al.
5,547,835 A 8/1996 Koster
5,567,587 A 10/1996 Kohne
5,576,204 A 11/1996 Blanco et al.
5,580,733 A 12/1996 Levis et al.
5,605,798 A 2/1997 Koster
5,608,217 A 3/1997 Franzen et al.
5,612,179 A 3/1997 Simons
5,622,824 A 4/1997 Koster
5,625,184 A 4/1997 Vestal et al.
5,639,606 A 6/1997 Willey
5,641,632 A 6/1997 Kohne
5,645,985 A 7/1997 Froehler et al.
5,683,869 A 11/1997 Ramsay Shaw et al.
5,686,242 A 11/1997 Bruice et al.
5,691,141 A 11/1997 Koster
5,700,642 A 12/1997 Monforte et al.
5,702,895 A 12/1997 Matsunaga et al.
5,707,802 A 1/1998 Sandhu et al.
5,712,125 A 1/1998 Uhlen
5,716,825 A 2/1998 Hancock et al.
5,727,202 A 3/1998 Kucala
5,745,751 A 4/1998 Nelson et al.
5,747,246 A 5/1998 Pannetier et al.
5,747,251 A 5/1998 Carson et al.
5,753,467 A 5/1998 Jensen et al.
5,753,489 A 5/1998 Kistner et al.
5,759,771 A 6/1998 Tilanus
5,763,169 A 6/1998 Sandhu et al.
5,763,588 A 6/1998 Matteucci et al.
5,770,367 A 6/1998 Southern et al.
5,777,324 A 7/1998 Hillenkamp
5,814,442 A 9/1998 Natarajan et al.
5,822,824 A 10/1998 Dion
5,828,062 A 10/1998 Jarrell et al.
5,830,653 A 11/1998 Froehler et al.
5,830,655 A 11/1998 Monforte et al.
5,830,853 A 11/1998 Backstrom et al.
5,832,489 A 11/1998 Kucala
5,834,255 A 11/1998 vanGemen et al.
5,845,174 A 12/1998 Yasui et al.
5,849,492 A 12/1998 Rogan
5,849,497 A 12/1998 Steinman
5,849,901 A 12/1998 Mabilat et al.
5,851,765 A 12/1998 Koster (Continued)

FOREIGN PATENT DOCUMENTS

AU 2003245488 6/2002

(Continued)

OTHER PUBLICATIONS

Buck (Biotechniques (1999) 27(3):528-536).*
Kinney et al. (American J. Trop. Med. Hyg., 1998, vol. 59, No. 6, p. 952-954).*
Lowe et al. (Nucleic Acids Research, 1990, vol. 18, No. 7, p. 1757-1761).*
Xu et al. (Analytical Chemistry, 1997, vol. 69, No. 17, p. 3595-3602).*
Magnuson et al. (Biotechniques, 1996, 21(4):700-709).*
Widjojoatmodjo et al. (Journal of Clinical Microbiology, 1992, vol. 30, No. 12, p. 3195-3199).*
Armstrong, P. et al., "Sensitive and Specific Colorimetric Dot Assay to Detect Eastern Equine Encephalomyelitis Viral RNA in Mosquitoes (Diptera: Culcidiea) After Polymerase Chain Reaction Amplification," *J. Med. Entomol.* (1995) 32(1): 42-52.
Boivin-Jahns, V. et al., "Bacterial Diversity in a Deep-Subsurface Clay Environment," *Appl. Environ. Microbiol.* (1996) 62(9): 3405-3412.
Brightwell, G. et al., "Genetic targets for the detection and identification of Venezuelan equine encephalitis viruses," *Arch. Virol.* (1998) 143(4): 731-742.

(Continued)

*Primary Examiner* — Stephanie K Mummert
(74) *Attorney, Agent, or Firm* — Casimir Jones, S.C.

(57) ABSTRACT

The present invention provides oligonucleotide primers and compositions and kits containing the same for rapid identification of alphaviruses by amplification of a segment of viral nucleic acid followed by molecular mass analysis.

10 Claims, 3 Drawing Sheets

U.S. PATENT DOCUMENTS

| | | | |
|---|---|---|---|
| 5,856,174 A | 1/1999 | Lipschutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz |
| 6,270,973 B1 | 8/2001 | Lewis et al. |
| 6,270,974 B1 | 8/2001 | Shultz et al. |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,286,146 B1 | 9/2001 | Rocker |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,716,634 B1 | 4/2004 | Myerson |
| 6,783,939 B2 * | 8/2004 | Olmsted et al. .................. 435/6 |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Koster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Koster et al. |
| 7,501,251 B2 | 3/2009 | Koster et al. |
| 7,666,588 B2 | 2/2010 | Ecker et al. |
| 7,718,354 B2 | 5/2010 | Ecker et al. |
| 7,741,036 B2 | 6/2010 | Ecker et al. |

| | | |
|---|---|---|
| 7,781,162 B2 | 8/2010 | Ecker et al. |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 | 4/2002 | Krstyanne et al. |
| 2002/0045178 A1 | 4/2002 | Cantor et al. |
| 2002/0055101 A1 | 5/2002 | Bergereon et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150903 A1 | 10/2002 | Koster |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0082539 A1 | 5/2003 | Ecker et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0124556 A1 | 7/2003 | Ecker et al. |
| 2003/0129589 A1 | 7/2003 | Koster et al. |
| 2003/0134312 A1 | 7/2003 | Burgyone et al. |
| 2003/0143201 A1 | 7/2003 | Nagata et al. |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Mamellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0161770 A1 | 8/2004 | Ecker et al. |
| 2004/0180328 A1 | 9/2004 | Ecker et al. |
| 2004/0185438 A1 | 9/2004 | Ecker et al. |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Michelevich et al. |
| 2005/0130196 A1 | 6/2005 | Hofstadler |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0020391 A1 | 1/2006 | Kreiswirth et al. |
| 2006/0057605 A1 | 3/2006 | Sampath et al. |
| 2006/0121520 A1 | 6/2006 | Ecker et al. |
| 2006/0172330 A1 | 8/2006 | Osborn et al. |
| 2006/0205040 A1 | 9/2006 | Sampath et al. |
| 2006/0240412 A1 | 10/2006 | Hall et al. |
| 2006/0259249 A1 | 11/2006 | Sampath et al. |
| 2006/0275788 A1 | 12/2006 | Ecker et al. |
| 2007/0048735 A1 | 3/2007 | Ecker et al. |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster et al. |
| 2009/0092977 A1 | 4/2009 | Koster et al. |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2010/0070194 A1 | 3/2010 | Ecker et al. |
| 2010/0145626 A1 | 6/2010 | Ecker et al. |
| 2010/0184035 A1 | 7/2010 | Hall et al. |

FOREIGN PATENT DOCUMENTS

| | | |
|---|---|---|
| CN | 1202204 | 12/1998 |
| DE | 19732086 | 1/1999 |
| DE | 19802905 | 7/1999 |
| DE | 19824280 | 12/1999 |
| DE | 19852167 | 5/2000 |
| DE | 19943374 | 3/2001 |
| DE | 10132147 | 2/2003 |
| EP | 0281390 | 9/1988 |
| EP | 0620862 | 10/1994 |
| EP | 0633321 | 11/1995 |
| EP | 1035219 | 9/2000 |
| EP | 1138782 | 10/2001 |
| EP | 1234888 | 8/2002 |
| EP | 1308506 | 5/2003 |
| EP | 1310571 | 5/2003 |
| EP | 1333101 | 8/2003 |
| EP | 1365031 | 11/2003 |
| EP | 1234888 A3 | 1/2004 |
| EP | 1748072 | 1/2007 |
| FR | 2811321 | 1/2002 |
| GB | 2325002 | 11/1998 |
| GB | 2339905 | 2/2000 |
| JP | 5-276999 | 10/1993 |
| JP | 11137259 A | 5/1999 |
| JP | 2004-200 | 1/2004 |
| JP | 2004-24206 | 1/2004 |
| JP | 2004-201641 | 7/2004 |
| JP | 2004-201679 | 7/2004 |
| WO | WO 88/03957 | 6/1988 |

| | | |
|---|---|---|
| WO | WO 90/15157 | 12/1990 |
| WO | WO 92/08117 | 5/1992 |
| WO | WO 92/09703 | 6/1992 |
| WO | WO 92/05182 | 11/1992 |
| WO | WO 92/19774 | 11/1992 |
| WO | WO 93/03186 | 2/1993 |
| WO | WO9305182 A1 | 3/1993 |
| WO | WO 93/08297 | 4/1993 |
| WO | WO 94/16101 | 7/1994 |
| WO | WO 94/19490 | 9/1994 |
| WO | WO 94/21822 | 9/1994 |
| WO | WO 95/04161 | 2/1995 |
| WO | WO 95/11996 | 5/1995 |
| WO | WO 95/13395 | 5/1995 |
| WO | WO 95/13396 | 5/1995 |
| WO | WO95/31997 | 11/1995 |
| WO | WO9606187 A1 | 2/1996 |
| WO | WO 96/16186 | 5/1996 |
| WO | WO 96/29431 | 9/1996 |
| WO | WO 96/32504 | 10/1996 |
| WO | WO 96/35450 | 11/1996 |
| WO | WO 96/37630 | 11/1996 |
| WO | WO 97/33000 | 9/1997 |
| WO | WO 97/34909 | 9/1997 |
| WO | WO 97/37041 | 10/1997 |
| WO | WO 97/47766 | 12/1997 |
| WO | WO 98/03684 | 1/1998 |
| WO | WO 98/12355 | 3/1998 |
| WO | WO 98/14616 | 4/1998 |
| WO | WO 98/15652 | 4/1998 |
| WO | WO 98/20020 | 5/1998 |
| WO | WO 98/20157 | 5/1998 |
| WO | WO 98/20166 | 5/1998 |
| WO | WO 98/26095 | 6/1998 |
| WO | WO 98/31830 | 7/1998 |
| WO | WO 98/35057 | 8/1998 |
| WO | WO 98/40520 | 9/1998 |
| WO | WO 98/54751 | 12/1998 |
| WO | WO9854571 A1 | 12/1998 |
| WO | WO 99/05319 | 2/1999 |
| WO | WO 99/12040 | 3/1999 |
| WO | WO 99/13104 | 3/1999 |
| WO | WO 99/14375 | 3/1999 |
| WO | WO 99/29898 | 6/1999 |
| WO | WO 99/31278 | 6/1999 |
| WO | WO 00/63362 | 10/1999 |
| WO | WO 99/57318 | 11/1999 |
| WO | WO 99/58713 | 11/1999 |
| WO | WO 99/60183 | 11/1999 |
| WO | WO0032750 A1 | 6/2000 |
| WO | WO0038636 A1 | 7/2000 |
| WO | WO 00/66789 | 11/2000 |
| WO | WO0066762 A2 | 11/2000 |
| WO | WO0077260 A1 | 12/2000 |
| WO | WO0100828 A2 | 1/2001 |
| WO | WO 01/07648 | 2/2001 |
| WO | WO 01/12853 | 2/2001 |
| WO | WO0120018 A2 | 3/2001 |
| WO | WO 01/23604 | 4/2001 |
| WO | WO 01/23608 | 4/2001 |
| WO | WO 01/32930 | 5/2001 |
| WO | WO 01/40497 | 6/2001 |
| WO | WO 01/46404 | 6/2001 |
| WO | WO 01/51661 | 7/2001 |
| WO | WO 01/51662 | 7/2001 |
| WO | WO 01/57263 | 8/2001 |
| WO | WO 01/57518 | 8/2001 |
| WO | WO 01/73119 | 10/2001 |
| WO | WO 01/73199 | 10/2001 |
| WO | WO 01/77392 | 10/2001 |
| WO | WO0196388 A2 | 12/2001 |
| WO | WO 02/02811 | 1/2002 |
| WO | WO 02/10186 | 2/2002 |
| WO | WO 02/10444 | 2/2002 |
| WO | WO 02/18641 | 3/2002 |
| WO | WO 02/21108 | 3/2002 |
| WO | WO 02/22873 | 3/2002 |
| WO | WO 02/24876 | 3/2002 |
| WO | WO 02/50307 | 6/2002 |
| WO | WO 02/057491 | 7/2002 |
| WO | WO 02/070664 | 9/2002 |
| WO | WO 02/070728 | 9/2002 |
| WO | WO02070737 A2 | 9/2002 |
| WO | WO 02/077278 | 10/2002 |
| WO | WO 02/099034 | 12/2002 |
| WO | WO 02/099095 | 12/2002 |
| WO | WO 02/099129 | 12/2002 |
| WO | WO 02/099130 | 12/2002 |
| WO | WO 03/002750 | 1/2003 |
| WO | WO 03/008636 | 1/2003 |
| WO | WO03001976 A2 | 1/2003 |
| WO | WO 03/012058 | 2/2003 |
| WO | WO 03/012074 | 2/2003 |
| WO | WO 03/014382 | 2/2003 |
| WO | WO 03/016546 | 2/2003 |
| WO | WO 03/020890 | 3/2003 |
| WO | WO03018636 A2 | 3/2003 |
| WO | WO 03/033732 | 4/2003 |
| WO | WO 03/054162 | 7/2003 |
| WO | WO 03/054755 | 7/2003 |
| WO | WO 03/060163 | 7/2003 |
| WO | WO 03/075955 | 9/2003 |
| WO | WO 03/088979 | 10/2003 |
| WO | WO 03/093506 | 11/2003 |
| WO | WO 03/097869 | 11/2003 |
| WO | WO 03/100035 | 12/2003 |
| WO | WO 03/100068 | 12/2003 |
| WO | WO 03/102191 | 12/2003 |
| WO | WO 03/104410 | 12/2003 |
| WO | WO03106635 A2 | 12/2003 |
| WO | WO 2004/003511 | 1/2004 |
| WO | WO2004009849 A1 | 1/2004 |
| WO | WO 2004/011651 | 2/2004 |
| WO | WO 2004/013357 | 2/2004 |
| WO | WO 2004/040013 | 5/2004 |
| WO | WO 2004/044123 | 5/2004 |
| WO | WO 2004/044247 | 5/2004 |
| WO | WO 2004/052175 | 6/2004 |
| WO | WO 2004/053076 | 6/2004 |
| WO | WO 2004/053141 | 6/2004 |
| WO | WO 2004/053164 | 6/2004 |
| WO | WO 2004/060278 | 7/2004 |
| WO | WO 2004/070001 | 8/2004 |
| WO | WO 2004/072230 | 8/2004 |
| WO | WO 2004/072231 | 8/2004 |
| WO | WO 2004/101809 | 11/2004 |
| WO | WO 2005/003384 | 1/2005 |
| WO | WO 2005/012572 | 2/2005 |
| WO | WO2005009202 A2 | 2/2005 |
| WO | WO 2005/024046 | 3/2005 |
| WO | WO2005036369 A2 | 4/2005 |
| WO | WO 2005/053141 | 6/2005 |
| WO | WO 2005/054454 | 6/2005 |
| WO | WO2005086634 A2 | 9/2005 |
| WO | WO 2005/075686 | 10/2005 |
| WO | WO 2005/091971 | 10/2005 |
| WO | WO 2005/098047 | 10/2005 |
| WO | WO2005116263 A2 | 12/2005 |
| WO | WO 2006/089762 | 8/2006 |
| WO | WO 2006/094238 | 9/2006 |
| WO | WO 2006/116127 | 11/2006 |
| WO | WO2006135400 A2 | 12/2006 |
| WO | WO2007014045 A2 | 2/2007 |
| WO | WO 2007/086904 | 8/2007 |
| WO | WO2008104002 A2 | 8/2008 |
| WO | WO 2008/118809 | 10/2008 |

OTHER PUBLICATIONS

Bronzoni, R. V. M. et al., "Multiplex nested PCR for Brazilian Alphavirus diagnosis," *Trans. R. Soc. Trop. Med. Hyg.* (2004) 98(8): 456-461.

Bronzoni, R. V. M. et al., "Duplex Reverse Transcription-PCR Followed by Nested PCR Assays for Detection and Identification of Brazilian Alphaviruses and Flaviviruses," *J. Clin. Microbiol.* (2005) 43(2): 696-702.

Chandra, S. et al., "Virus reduction in the preparation of intravenous immune globulin: in vitro experiments," *Transfusion* (1999) 39 (3): 249-257.

Hasebe, F. et al., "Combined Detection and Genotyping of *Chikungunya* Virus by a Specific Reverse Transcription-Polymerase Chain Reaction," *J. Med. Virol.* (2002) 67(3): 370-374.

Huang, C. et al, "Detection of arboviral RNA directly from mosquito homogenates by reverse-transcription-polymerase chain reaction,"*J. Virol. Methods* (2001) 94(1-2): 121-128.

Kramer, L. D. et al., "Detection of St. Louis Encephalitis and Western Equine Encephalomyelitis RNA in Mosquitoes Tested Without Maintenance of a Cold Chain," *J. Am. Mosq. Control Assoc.* (2001) 17(4): 213-215.

Kramer, L. D. et al., "Detection of Encephalitis Viruses in Mosquitoes (Diptera: Culicidea) and Avian Tissues," *J. Med. Entomol.* (2002) 39(2): 312-323.

Lambert, A. J. et al., "Detection of North American Eastern and Western Equine Encephalitis Viruses by Nucleic Acid Amplification Assays," *J. Clin. Microbiol.* (2003) 41(1): 379-385.

Lee, J.-H. et al., "Simultaneous Detection of Three Mosquito-Borne Encephalitis Viruses (Eastern Equine, La Crosse, and St. Louis) with a Single-Tube Multiplex Reverse Transcriptase Polymerase Chain Reaction Assay," *J. Am. Mosq. Control. Assoc.* (2002) 18(1): 26-31.

Linssen, B. et al., "Development of Reverse Transcription-PCR Assays Specific for Detection of Equine Encephalitis Viruses," *J. Clin. Microbiol.* (2000) 38(4): 1527-1535.

Monroy, A. M. et al., "Evaluation of Reverse Transcriptase Polymerase Chain Reaction for the Detection of Eastern Equine Encephalomyelitis Virus during Vector Surveillance," *J. Med. Entomol.* (1996) 33(3): 449-457.

Muddiman, D. C. et al., "Length and Base Composition of PCR-Amplified Nucleic Acids Using Mass Measurements from Electrospray Ionization Mass Spectrometry," *Anal. Chem.* (1997) 69(8): 1543-1549.

Muddiman, D. C. et al., "Characterization of PCR Products from Bacilli Using Electrospray Ionization FTICR Mass Spectrometry," *Anal. Chem.* (1996) 68(21): 3705-3712.

O'Guinn, M. L. et al., "Field Detection of Eastern Equine Encephalitis Virus in the Amazon Basin Region of Peru Using Reverse Transcription-Polymerase Chain Reaction Adapted for Field Identification of Arthropod-Borne Pathogens," *Am. J. Trop. Med. Hyg.* (2004) 70(2): 164-171.

Pastorino, B. et al., "Development of a TaqMan® RT-PCR assay without RNA extraction step for the detection and quantification of African Chikungunya viruses," *J. Virol. Methods* (2005) 124(1-2): 65-71.

Pfeffer, M. et al., "Genus-Specific Detection of Alphaviruses by a Semi-Nested Reverse Transcription-Polymerase Chain Reaction," *Am. J. Trop. Med. Hyg.* (1997) 57(6): 709-718.

Pfeffer, M. et al., "Specific Detection of Chikungunya Virus Using a RT-PCR/Nested PCR Combination," *J. Vet. Med. B* (2002) 49(1): 49-54.

Sánchez-Seco, M. P. et al., "A generic nested-RT-PCR followed by sequencing for detection and identification of members of the alphavirus genus," *J. Virol. Methods* (2001) 95(1-2): 153-161.

Sellner, L. N. et al., "Sensitive detection of Ross River virus—a one-tube nested RT-PCR," *J. Virol. Methods* (1994) 49(1): 47-58.

Sellner, L., "A Single-Tube Nested RT-PCR for the Detection of Ross River Virus," *Methods Mol. Biol.* (1998) 92: 145-152.

Studdert, M. J. et al., "Polymerase chain reaction tests for the identification of Ross River, Kunjin and Murray Valley encephalitis virus infections in horses," *Aust. Vet. J.* (2003) 81(1-2): 76-80.

Widjojoatmodjo, M. N. et al., "Rapid Identification of Bacteria by PCR-Single-Strand Conformation Polymorphism,"*J. Clin. Microbiol.* (1994) 32(12): 3002-3007.

Examiner Interview Summary mailed Jun. 7, 2011 for U.S. Appl. No. 11/930,108, filed Oct. 31, 2007.

Final Office Action mailed Jun. 14, 2011 for U.S. Appl. No. 12/616,422, filed Nov. 11, 2009.

International Preliminary Report on Patentability and Written Opinion for Application No. PCT/US04/007236, mailed on Mar. 16, 2006, 7 pages.

International Preliminary Report on Patentability for Application No. PCT/US2005/018031, mailed on Nov. 29, 2006, 1 page.

Notice of Allowance mailed Jun. 9, 2011 for U.S. Appl. No. 11/331,987, filed Jan. 13, 2006.

Notice of Allowance mailed Jun. 9, 2011 for U.S. Appl. No. 11/491,376, filed Jul. 21, 2006.

Aaserud et al., "Accurate base composition of double-strand DNA by mass spectrometry" *J. Am. Soc. Spec.* (1996) 7:1266-1269.

Aaserud et al., "DNA sequencing with balckbody infrared radioactive dissociation of electrosprayed ions" Int. J. Mass. Spectrom. Ion Processes, (1997) 167-168: 705-712 (Reference not found in PubMed).

Adam et al., Molecular structure of the two-dimensional hexon crystalline array and of adenovirus capsid: *Acta Microbiol. Immuno. Hung.* (1998) 45:305-310.

Adam et al., "Intertype specific epitope structure of adenovirus hexon" *Acta Microbiol. Immuno. Hung.* (1998) 45:311-316.

Adam et al., "Characterization of intertype specific epitopes on adenovirus hexons" *Arch. Virol.* (1998) 143:1669-1682.

Adrian et al., "DNA restriction analysis of adenovirus prototypes 1 to 41" *Arch. Virol.* (1986) 91:277-290.

Adzhar et al., "Universal oligonucleotides for the detection of infectious bronchitis virus by the polymerase chain reaction" Avian Pathology (1996) 25:817-836.

Agostini et al. "Complete genome of a JC virus genotype Type 6 from the brain of an African American with progressive multifocal leukoencephalopathy" (1998) 1:267-272.

Akalu et al., "Rapid identification of subgenera of human adenovirus by serological and PCR assays" *J. Virol Methods* (1998) 71:187-196.

Allaouchiche et al., "Clinical Impact of Rapid Oxacillin Susceptibility Testing Using a PCR Assay in *Staphylococcus aureus* Bactaeremia" J. Infect. (1999) 39(3):198-204.

Allawi, H.T. & Santa Lucia J., Jr. Thermodynamics and NMR of internal G.T. mismatches in DNA, Biochemistry, 36, 10581-94 (1997).

Altschul et al., J. Mol. Biol., 215, 403-410 (1990).

Altschul et al., Nucl. Acid Res., 25:3389-3402 (1997).

Alves-Silva, J. et al., "The Ancestry of Brazilian mtDNA Lineages," *Am. J. Hum. Genet.* (2000) 67:444-461.

Amano et al., "Detection of influenza virus: traditional approaches and development of biosensors" Anal. Bioanal. Chem. (2005) 381:156-164.

Amexis et al., "Quantitiative mutant analysis of viral quasispecies by chip-based matrix-assisted laser desorption/ionization of time-of-flight mass spectrometry" PNAS (2001) 98(21):12097-12102; Correction: 98(24):14186.

Anderson et al., "Sequence and organization of the human mitochondrial genome," *Nature* (1981) 290:457-465.

Anderson and Young, Quantitative Filter Hybridization in Nucleic Acid Hybridization (1985).

Andreasson et al., "Mitochondrial Sequence Analysis for Forensic Identification Using Pyrosequencing Technology" *BioTechniques* (2002) 32:124-133.

Anthony et al., "Use of the Polymerase Chain Reaction for Rapid Detection of High-Level Mupirocin Resistance in *Staphylococci*" Eur. J. Clin. Microbiol. Infect. Dis. (1999) 18(1):30-34.

Application for Grant by David Mitchell Lubmann dated Oct. 25, 1992 and Oct. 29, 1992.

Application for Continuation Grant by David Mitchell Lubmann dated Jun. 10, 1994 and Jun. 24, 1994.

Application for Grant by David Mitchell Lubmann dated Sep. 1, 1994 and Sep. 27, 1994.

Application for Continuation Grant by David Mitchell Lubmann dated Jun. 4, 1996 and Jun. 14, 1996.

U.S. Appl. No. 09/798,007 Office Communication Mailed Apr. 16, 2002.

U.S. Appl. No. 09/798,007 Office Communication Mailed Jun. 20, 2002.

U.S. Appl. No. 09/798,007 Office Communication Mailed Nov. 6, 2002.

U.S. Appl. No. 09/798,007 Office Communication Mailed Jan. 8, 2003.

U.S. Appl. No. 09/798,007 Office Communication Mailed Jan. 31, 2003.

U.S. Appl. No. 09/798,007 Office Communication Mailed Feb. 27, 2003.

U.S. Appl. No. 09/798,007 Office Communication Mailed May 20, 2003.
U.S. Appl. No. 09/798,007 Office Communication Mailed May 28, 2003.
U.S. Appl. No. 09/798,007 Office Communication Mailed Jul. 11, 2003.
U.S. Appl. No. 09/798,007 Office Communication Mailed Sep. 22, 2003.
U.S. Appl. No. 09/798,007 Office Communication Mailed Nov. 19, 2003.
U.S. Appl. No. 09/798,007 Office Communication Mailed Jun. 30, 2004.
U.S. Appl. No. 09/798,007 Office Communication Mailed Aug. 10, 2004.
U.S. Appl. No. 09/798,007 Office Communication Mailed Feb. 10, 2005.
U.S. Appl. No. 09/891,793 Office Communication Mailed Dec. 18, 2002.
U.S. Appl. No. 09/891,793 Office Communication Mailed May 19, 2003 interview summary report.
U.S. Appl. No. 09/891,793 Office Communication Mailed May 23, 2003.
U.S. Appl. No. 09/891,793 Office Communication Mailed Aug. 26, 2003.
U.S. Appl. No. 09/891,793 Office Communication Mailed Nov. 13, 2003.
U.S. Appl. No. 09/891,793 Office Communication Mailed Mar 9, 2004.
U.S. Appl. No. 09/891,793 Office Communication Mailed Jun. 14, 2004.
U.S. Appl. No. 09/891,793 Office Communication Mailed Jul. 13, 2004.
U.S. Appl. No. 09/891,793 Office Communication Mailed Aug. 10, 2004.
U.S. Appl. No. 09/891,793 Office Communication Mailed Oct. 20, 2004.
U.S. Appl. No. 09/891,793 Office Communication Mailed Mar. 8, 2005.
U.S. Appl. No. 09/891,793 Office Communication Mailed May 19, 2005.
U.S. Appl. No. 09/891,793 Office Communication Mailed Aug. 11, 2005.
U.S. Appl. No. 09/891,793 Office Communication Mailed Mar. 16, 2006.
U.S. Appl. No. 09/891,793 Office Communication Mailed Jul. 12, 2006.
U.S. Appl. No. 09/891,793 Office Communication Mailed Sep. 13, 2006.
U.S. Appl. No. 09/891,793 Office Communication Mailed Nov. 20, 2006.
U.S. Appl. No. 09/891,793 Office Communication Mailed Jul. 22, 2008.
U.S. Appl. No. 10/156,608 Office Communication Mailed Apr. 1, 2004.
U.S. Appl. No. 10/156,608 Office Communication Mailed Aug. 10, 2004.
U.S. Appl. No. 10/156,608 Office Communication Mailed Oct. 14, 2004.
U.S. Appl. No. 10/156,608 Office Communication Mailed Nov. 19, 2004.
U.S. Appl. No. 10/156,608 Office Communication Mailed Dec. 9, 2004.
U.S. Appl. No. 10/156,608 Office Communication Mailed May 23, 2005.
U.S. Appl. No. 10/156,608 Office Communication Mailed May 26, 2005.
U.S. Appl. No. 10/156,608 Office Communication Mailed Jul. 20, 2005.
U.S. Appl. No. 10/156,608 Office Communication Mailed Sep. 15, 2005.
U.S. Appl. No. 10/156,608 Office Communication Mailed Jun. 2, 2006.
U.S. Appl. No. 10/323,438 Office Communication Mailed Nov. 20, 2003.
U.S. Appl. No. 10/323,438 Office Communication Mailed Jul. 26, 2004.
U.S. Appl. No. 10/325,527 Office Communication Mailed Dec. 3, 2003.
U.S. Appl. No. 10/325,527 Office Communication Mailed Aug. 16, 2004.
U.S. Appl. No. 10/325,527 Office Communication Mailed Mar. 11, 2005.
U.S. Appl. No. 10/326,642 Office Communication Mailed Nov. 21, 2003.
U.S. Appl. No. 10/326,642 Office Communication Mailed Jul. 14, 2004.
U.S. Appl. No. 10/418,514 Office Communication Mailed Sep. 29, 2005.
U.S. Appl. No. 10/418,514 Office Communication Mailed Feb. 27, 2006.
U.S. Appl. No. 10/418,514 Office Communication Mailed Mar. 27, 2007.
U.S. Appl. No. 10/418,514 Office Communication Mailed Dec. 6, 2007.
U.S. Appl. No. 10/418,514 Office Communication Mailed Apr. 15, 2008.
U.S. Appl. No. 10/418,514 Office Communication Mailed Jul. 1, 2008.
U.S. Appl. No. 10/418,514 Office Communication Mailed Mar. 23, 2009.
U.S. Appl. No. 10/418,514 Office Communication Mailed Sep. 29, 2009.
U.S. Appl. No. 10/660,122 Office Communication Mailed Mar. 17, 2006.
U.S. Appl. No. 10/660,122 Office Communication Mailed Jul. 6, 2006.
U.S. Appl. No. 10/660,122 Office Communication Mailed Sep. 19, 2006.
U.S. Appl. No. 10/660,122 Office Communication Mailed Apr. 20, 2007.
U.S. Appl. No. 10/660,122 Office Communication Mailed Sep. 19, 2007.
U.S. Appl. No. 10/660,122 Office Communication Mailed Mar. 21, 2008.
U.S. Appl. No. 10/660,122 Office Communication Mailed Jul. 9, 2008.
U.S. Appl. No. 10/660,122 Office Communication Mailed Sep. 17, 2008.
U.S. Appl. No. 10/660,996 Office Communication Mailed Feb. 28, 2006.
U.S. Appl. No. 10/660,996 Office Communication Mailed May 30, 2006.
U.S. Appl. No. 10/660,996 Office Communication Mailed Jul. 12, 2006.
U.S. Appl. No. 10/660,996 Office Communication Mailed Sep. 5, 2006.
U.S. Appl. No. 10/660,996 Office Communication Mailed Nov. 22, 2006.
U.S. Appl. No. 10/660,996 Office Communication Mailed Jul. 10, 2007 with associated Information Disclosure Statement filed Feb. 21, 2007.
U.S. Appl. No. 10/660,997 Office Communication Mailed Mar. 13, 2006.
U.S. Appl. No. 10/660,997 Office Communication Mailed May 26, 2006.
U.S. Appl. No. 10/660,997 Office Communication Mailed Sep. 18, 2006.
U.S. Appl. No. 10/660,997 Office Communication Mailed Nov. 21, 2006.
U.S. Appl. No. 10/660,997 Office Communication Mailed Apr. 26, 2007 with associated Information Disclosure Statement filed Feb. 20, 2007.
U.S. Appl. No. 10/660,998 Office Communication Mailed May 1, 2006.

U.S. Appl. No. 10/660,998 Office Communication Mailed Aug. 3, 2006.
U.S. Appl. No. 10/660,998 Office Communication Mailed Jan. 24, 2007.
U.S. Appl. No. 10/660,998 Office Communication Mailed Aug. 7, 2007.
U.S. Appl. No. 10/660,998 Office Communication Mailed Dec. 11, 2007.
U.S. Appl. No. 10/660,998 Office Communication Mailed Sep. 19, 2008.
U.S. Appl. No. 10/660,998 Office Communication Mailed Apr. 7, 2009.
U.S. Appl. No. 10/728,486 Office Communication Mailed Apr. 10, 2006.
U.S. Appl. No. 10/728,486 Office Communication Mailed Jul. 27, 2006.
U.S. Appl. No. 10/728,486 Office Communication Mailed Oct. 17, 2007.
U.S. Appl. No. 10/728,486 Office Communication Mailed Dec. 20, 2006.
U.S. Appl. No. 10/728,486 Office Communication Mailed May 11, 2007.
U.S. Appl. No. 10/728,486 Office Communication Mailed Jan. 23, 2008.
U.S. Appl. No. 10/728,486 Office Communication Mailed Nov. 3, 2008.
U.S. Appl. No. 10/754,415 Office Communication Mailed Mar. 13, 2006.
U.S. Appl. No. 10/754,415 Office Communication Mailed Aug. 28, 2006.
U.S. Appl. No. 10/754,415 Office Communication Mailed Nov. 17, 2006.
U.S. Appl. No. 10/754,415 Office Communication Mailed Feb. 27, 2007.
U.S. Appl. No. 10/754,415 Office Communication Mailed Aug. 30, 2007.
U.S. Appl. No. 10/754,415 Office Communication Mailed Oct. 10, 2007.
U.S. Appl. No. 10/754,415 Office Communication Mailed Jun. 12, 2008.
U.S. Appl. No. 10/754,415 Office Communication Mailed Jun. 4, 2009.
U.S. Appl. No. 10/829,826 Office Communication Mailed Jul. 6, 2007.
U.S. Appl. No. 10/829,826 Office Communication Mailed Apr. 4, 2008.
U.S. Appl. No. 10/829,826 Office Communication Mailed Dec. 10, 2008.
U.S. Appl. No. 10/844,938 Office Communication Mailed Feb. 2, 2007.
U.S. Appl. No. 10/844,938 Office Communication Mailed Aug. 7, 2007.
U.S. Appl. No. 10/844,938 Office Communication Mailed May 20, 2008.
U.S. Appl. No. 10/844,938 Office Communication Mailed Jan. 30, 2009.
U.S. Appl. No. 10/891,337 Office Communication Mailed Apr. 20, 2009.
U.S. Appl. No. 10/933,928 Office Communication Mailed Jun. 2, 2006.
U.S. Appl. No. 10/943,344 Office Communication Mailed Feb. 27, 2007.
U.S. Appl. No. 10/943,344 Office Communication Mailed May 21, 2008.
U.S. Appl. No. 10/943,344 Office Communication Mailed Feb. 23, 2009.
U.S. Appl. No. 10/943,344 Office Communication Mailed Oct. 14, 2009.
U.S. Appl. No. 11/059,776 Office Communication Mailed Jan. 19, 2007.
U.S. Appl. No. 11/059,776 Office Communication Mailed May 29, 2007.
U.S. Appl. No. 11/059,776 Office Communication Mailed Jan. 23, 2008.
U.S. Appl. No. 11/060,135 Office Communication Mailed Dec. 21, 2006.
U.S. Appl. No. 11/060,135 Office Communication Mailed Mar. 8, 2007.
U.S. Appl. No. 11/060,135 Office Communication Mailed Jul. 24, 2007.
U.S. Appl. No. 11/060,135 Office Communication Mailed Mar. 25, 2008.
U.S. Appl. No. 11/060,135 Office Communication Mailed Jan. 2, 2009.
U.S. Appl. No. 11/060,135 Office Communication Mailed Jul. 15, 2009.
U.S. Appl. No. 11/136,134 Office Communication Mailed Jun. 20, 2007.
U.S. Appl. No. 11/136,134 Office Communication Mailed Mar. 26, 2008.
U.S. Appl. No. 11/136,134 Office Communication Mailed Oct. 31, 2008.
U.S. Appl. No. 11/136,134 Office Communication Mailed Feb. 12, 2009.
U.S. Appl. No. 11/136,134 Office Communication Mailed May 21, 2009.
U.S. Appl. No. 11/210,516 Office Communication Mailed Jun. 8, 2007.
U.S. Appl. No. 11/210,516 Office Communication Mailed Oct. 19, 2007.
U.S. Appl. No. 11/233,630 Office Communication Mailed Jun. 8, 2007.
U.S. Appl. No. 11/233,630 Office Communication Mailed Jul. 13, 2007.
U.S. Appl. No. 11/233,630 Office Communication Mailed Apr. 16, 2008.
U.S. Appl. No. 11/233,630 Office Communication Mailed Oct. 2, 2008.
U.S. Appl. No. 11/331,978 Office Communication Mailed Nov. 15, 2007.
U.S. Appl. No. 11/331,978 Office Communication Mailed Aug. 15, 2008.
U.S. Appl. No. 11/331,978 Office Communication Mailed Oct. 17, 2008.
U.S. Appl. No. 11/331,978 Office Communication Mailed Jun. 2, 2008 (interview summary).
U.S. Appl. No. 11/331,987 Office Communication Mailed Jul. 16, 2007.
U.S. Appl. No. 11/331,987 Office Communication Mailed Oct. 22, 2007.
U.S. Appl. No. 11/331,987 Office Communication Mailed Jul. 9, 2008.
U.S. Appl. No. 11/331,987 Office Communication Mailed Nov. 20, 2009.
U.S. Appl. No. 11/404,561 Office Communication Mailed May 16, 2008.
U.S. Appl. No. 11/404,561 Office Communication Mailed Feb. 4, 2009.
U.S. Appl. No. 11/409,535 Office Communication Mailed Oct. 31, 2007.
U.S. Appl. No. 11/409,535 Office Communication Mailed Apr. 16, 2008.
U.S. Appl. No. 11/491,376 Office Communication Mailed Oct. 31, 2008.
U.S. Appl. No. 11/491,376 Office Communication Mailed Apr. 22, 2009.
U.S. Appl. No. 11/582,859 Office Communication Mailed Oct. 21, 2008.
U.S. Appl. No. 11/582,863 Office Communication Mailed Aug. 20, 2007.
U.S. Appl. No. 11/582,863 Office Communication Mailed Jun. 17, 2008.
U.S. Appl. No. 11/582,863 Office Communication Mailed Feb. 26, 2009.

U.S. Appl. No. 11/582,875 Office Communication Mailed Nov. 17, 2009.
U.S. Appl. No. 11/582,930 Office Communication Mailed Sep. 14, 2007.
U.S. Appl. No. 11/582,930 Office Communication Mailed May 2, 2008.
U.S. Appl. No. 11/582,930 Office Communication Mailed Oct. 24, 2008.
U.S. Appl. No. 11/582,930 Office Communication Mailed Jan. 16, 2009.
U.S. Appl. No. 11/582,930 Office Communication Mailed Jul. 2, 2009.
U.S. Appl. No. 11/685,598 Office Communication Mailed Aug. 18, 2009.
U.S. Appl. No. 11/754,163 Office Communication Mailed Jul. 28, 2009.
U.S. Appl. No. 11/754,169 Office Communication Mailed Aug. 25, 2009.
U.S. Appl. No. 11/754,174 Office Communication Mailed Aug. 3, 2009.
U.S. Appl. No. 11/754,182 Office Communication Mailed Jul. 2, 2009.
U.S. Appl. No. 11/929,707 Office Communication Mailed Jul. 17, 2009.
U.S. Appl. No. 11/929,707 Office Communication Mailed Oct. 2, 2009.
U.S. Appl. No. 12/211,641 Office Communication Mailed Apr. 17, 2009.
U.S. Appl. No. 12/326,800 Office Communication Mailed Oct. 21, 2009.
U.S. Appl. No. 90/010,209 Office Communication Mailed Jun. 27, 2008.
U.S. Appl. No. 90/010,209 Office Communication Mailed Jul. 22, 2008.
U.S. Appl. No. 90/010,210 Office Communication Mailed Jun. 27, 2008.
U.S. Appl. No. 90/010,210 Office Communication Mailed Jul. 22, 2008.
U.S. Appl. No. 90/010,447 Office Communication Mailed Apr. 24, 2009.
U.S. Appl. No. 90/010,447 Office Communication Mailed Mar. 12, 2009.
U.S. Appl. No. 90/010,447 Office Communication Mailed Oct. 29, 2009.
U.S. Appl. No. 90/010,448 Office Communication Mailed Apr. 24, 2009.
U.S. Appl. No. 90/010,448 Office Communication Mailed Mar. 12, 2009.
Arbique et al., "Comparison of the Velogene Rapid MRSA Identification Assay, Denka MRSA-Screen Assay, and BBL Crystal MRSA ID System for rapid identification of methicillin-resistant *Staphylococcus aureus*" Diagn. Microbiol. Infect. Dis. (2001) 40(1-2):5-10.
Archer, G. L. et al., "Detection of Methicillin Resistance in Staphylococci by Using a DNA Probe," *Antimicrob. Agents Chemother*. (1990) 34(9): 1720-1724.
Arnal et al., "Quantification of Hepatitis A virus in shellfish by competitive reverse transcription PCR with coextraction of standard RNA" Applied and Environmental Microbiology, American Society for Microbiology (1999) 65(1):322-326.
Aronsson et al., Persistence of the influenza A/WSN/33 virus RNA at midbrain levels of immunodefective mice, Online Publication Date: Apr. 1, 2001, Journal of the NeuroVirology 7:117-124, 2001.
Ausubel et al., Current Protocols in Molecular Biology (Relevant portions of the book), 1992.
Avellon et al. "Rapid and sensitive diagnosis of human adenovirus infections by a generic polymerase chain reaction" *J. Virol. Methods* (2001) 92:113-120.
Azevedo et al. "Detection of influenza, parainfluenza, adenovirus and respiratory syncytial virus during asthma attacks in children older than two years old." Allergol. lmmunopathol. (2003) 31:311-317.
Baba et al., "Genome and virulence determinants of high virulence community-acquired MRSA" Lancet (2002) 359:1819-1827.

Bahrmand et al., "Polymerase chain reaction of bacterial genomes with single universal primer: application to distinguishing mycobacteria species" *Molecular and Cellular Probes* (1996) 10:117-122.
Bahrmand et al., "Use of restriction enzyme analysis of amplified DNA coding for the hsp65 gene and polymerase chain reaction with universal primer for rapid differentiation of mycobacterium species in the clinical laboratory" *Scandinavian Journal of Infectious Diseases* (1998) 30:477-480.
Bai, J, T.H. Liu and D.M.. Lubman, "Matrix-Assisted Laser Desorption/Ionization Mass Spectrometry of Restriction Enzyme-Digested Plasmid DNA Using an Active Nafion Substrate," 8 Rapid Commun. Mass Spectrom. 687-691 (1994) ('787 reexamination).
Baker et al., "Review and re-analysis of domain-specific 16S primers" *J. Microbiol. Methods* (2003) 55:541-555.
Banik et al. "Multiplex PCR assay for rapid identification of oculopathogenic adenoviruses by amplification of the fiber and hexon genes" *J. Clin. Microbiol* (2005) 43:1064-1068.
Barbour et al. "Identification of an uncultivatable Borrelia species in the hard tick *Amblyomma americanum*: Possible agent of a Lyme disease-like illness" The Journal of Infectious Diseases (1996) 173:403-409.
Barns et al., "Detection of diverse new Francisella-like bacteria in environmental samples." Applied and Environmental Microbiology (2005) 71:5494-5500.
Baron, E. J., "Genetic Aspects of Methicillin Resistance in *Staphylococcus aureus* and Methods Used for its Detection in Clinical Laboratories in the United States," *J. Chemother*. (1995) 7(Suppl. 3): 87-92.
Barr et al., "An Influenza A(H3) Reassortant Was Epidemic in Australia and New Zealand in 2003" J. Med. Virol. (2005) 76:391-397.
Barski, P. et al., "Rapid assay for detection of methicillin-resistant *Staphylococcus aureus* using multiplex Pcr," *Mol. Cell Probes* (1996) 10:471-475.
Bastia et al., "Organelle DNA analysis of Solanum and Brassica somatic hybrids by PCR with 'universal primers'." *Theoretical and Applied Genetics* (2001) 102:1265-1272.
Batey et al., "Preparation of Isotopically Labeled Ribonucleotides for Multidimensional NMR Spectroscopy of RNA" *Nucleic Acids Research* (1992) 20:4515-4523.
Baumer et al., "Age-related Human mtDNA Deletions: A Heterogeneous Set of Deletions Arising at a Single Pair of Directly Repeated Sequences" *Am. J. Hum. Genet*. (1994) 54:618-630.
Beall, B., et al. "Survey of emm Gene Sequences and T-Antigen Types from Systemic *Streptococcus pyogenes* Infection Isolates Collected in San Francisco, California; Atlanta, Georgia; and Connecticut in 1994 and 1995" (1997), J. Clin. Micro. 35, 1231-1235.
Beall et al., "Sequencing emm-Specific PCR Products for Routine and Accurate Typing of Group A Streptococci" (1996) J. Clin. Micro. 34, 953-958.
Benko, M. et al., "Family Adenoviridae", Virus taxonomy, VIIIth report of the International Committee on Taxonomy of Viruses (2004) Fauquet, C.M. et al. (Eds.) Academic Press, New York, pp. 213-228.
Benson et al., "Advantages of Thermococcus kodakaraenis (KOD) DNA polymerase for PCR-mass spectrometry based analyses" *J. Am. Soc. Mass Spectrom*. (2003) 14:601-604.
Berencsi, G. et al., "Molecular Biological Characterization of Adenovirus DNA", Acta Microbiol. Immunol. Hung, 1998, vol. 45, Nos. 3-4; pp. 297-304.
Bisno, A.L. (1995) "Streptococcus Pyogenes," Infectious Diseases and Their Etiologic Agents in "Principles and Practice of Infectious Diseases", eds., Mandell, G.L., Bennett, J.E. & Dolin, R. (Churchill Livingston, New York), vol. 2, pp. 1786-1799.
Black et al., "Detection of trace levels of tricothecene mycotoxins in human urine by gas chromatography-mass spectrometry" *J. Chromatog* (1986) 367:103-115.
Blaiotta, G. et al., "PCR detection of staphylococcal enterotoxin genes in *Staphylococcus* spp. strains isolated from meat and dairy products. Evidence for new variants of seG and sel in *S. aureus* AB-8802," *J. Appl. Microbiol*. (2004) 97:719-730.
BLAST Search results (Mar. 2006).
Bolton and McCarthy, Proc. Natl. Acad. Sci. U.S.A., 48, 1390 (1962).

Bont, Thomas et al., "Matrix-assisted laser desorption/ionization time-of-flight mass spectrometry-based detection of microsatellite instabilities in coding DNA sequences: a novel approach to identify DNA-mismatch repair-deficient cancer cells," Clinical Chemistry, 49(4):552-561 Apr. 2003.

Borrow et al., "SiaD PCR Elisa for confirmation and identification of serogroup Y and W135 meningococcal infections" *FEMS Microbiological Letters* (1998) 159:209-214.

Boubaker, K. et al., "Panton-Valentine Leukocidin and Staphylococcal Skin Infections in Schoolchildren," *Emerg.Infct. Dis.* (2004) 10(1):121-124.

Bowen et al., "The native virulence plasmid combination affects the segregational stability of a theta-replicating shuttle vector in *bacillus anthracis* var, New Hampshire" *J. Appl. Microbiol.* (1999) 87:270-278.

Bowers, K. M. et al., "Screening for methicillin resistance in *Staphylococars aureus* and coagulase-negative staphylococci: evaluation of three selective and Mastalex-MRSA latex agglutination," Br. *J. Biomed. Sci*. (2003) 60(2):71-74.

Brakstad, O. G. et al., "Multiplex polylnerase chain reaction for detection of genes for *Staphylococcus aureus* themonuclease and methicillin resistance and correlation with oxacillin resistance," *APMIS* (1993) 101:681-688.

Brakstad, O. G. et al., "Direct identification of *Staphylococcus aureus* in blood cultures by detection of the gene, encoding the thermostable nuclease or the gene product," *APMIS* (1995) 103:209-218.

Brandt, C.D., et al., "Infections in 18,000 Infants and Children in a Controlled Study of Respiration Tract Disease. I. Adenovirus Pathogenicity in Relation to Serologic Type and Illness Syndrome," Am. J. Epidemio.; 1969, vol. 90, No. 6, pp. 484-500.

Brayshaw, D. P., "Methicillin-resistant *Staphylococcus aureus*: evaluation of detection techniques on laboratory-passaged organisms," *Br. J Biomed. Sci*. (1999) 56:170-176.

Brightwell et al., "Development of internal controls for PCR detection of *Bacillus anthracis*" Molecular and Cellular Probes (1998) 12(6):367-377.

Brown, "Advances in Molecular Diagnostics for Avian Influenza" Dev. Biol. (2006) 124:93-97.

Brownstein et al., "Modulation of Non-Templated Nucleotide Addition by Taq DNA Polymerase: Primer Modifications that Facilitate Genotyping" BioTechniques (1996) 20:1004-1010.

Brunaud et al., "T-DNA integration into the *Arabidopsis* genome depends on sequences of pre-insertion sites" EMBO Rep. (2002) 3(12):1152-1157.

Butel et al. "Cell and molecular biology of simian virus 40: implications for human infections and diseases" J. Natl. Cancer Institute (1999) 91(2):119-134.

Butler "DNA profiling and quantitation of human DNA" CCQM BAWG 04122005, 2001.

Campbell et al., "Detection of California serogroup Bunyaviruses in tissue culture and mosquito pools by PCR" *J. Virol. Methods* (1996) 57:175-179.

Carracedo et al., "DNA commission of the international society for forensic genetics: guidelines for mitochondrial DNA typing" *Forensic Science International* (2000) 110:79-85.

Carroll, K. C. et al., "Rapid Detection of the Staphylococcal *mec*A Gene from BACTEC Blood Culture Bottles by the Polymerase Chain Reaction," *Am. J. Clin. Pathol*. (1996) 106:600-5.

Case et al., "Maternal inheritance of mitochondrial DNA polymorphisms in cultured human fibroblasts," *Somatic Cell Genetics* (1981) 7:103-108.

Cattoli et al., "Comparison of three rapid detection systems for type A influenza virus on tracheal swabs of experimentally and naturally infected birds" Avian Pathology (2004) 33(4):432-437.

Cavassini, M. et al., "Evaluation of MRSA-Screen, a Simple Anti-PBP 2a Slide Latex Agglutination Kit, for Rapid Detection of Methicillin Resistance in *Staphylococcus aureus," J. Clin. Microbial*. (1999) 37(5): 1591-1594.

Cespedes et al., "Polymerase chain reaction restriction fragment length polymorphism analysis of a short fragment of the cytochrome b gene for identification of flatfish species" *J. Food Protection* (1998) 61:1684-1685.

Chamberlin et al., "New RNA polymerase from *Escerichia coli* infected with bacteriophage T7" Nature 228:227 (1970).

Chang, P.-K. et al., "aflT, a MFS transporter-encoding gene located in the aflatoxin gene cluster, does not have a significant role in aflatoxin secretion," Fungal Genet.Biol. (2004) 41:911-920.

Chaves, F. et al., "Molecular Characterization of Resistance to Mupirocin in Methidlin-Susceptible and -Resistant Isolates of *Staphylococcus aureus* from Nasal Samples," *J. Clin. Microbiol*. (2004) 42(2):822-824.

Chelly et al., "Transcription of the dystrophin gene in human muscle and non-muscle tissue" Nature (1988) 333(6176):858-860.

Chen et al., "Universal primers for amplification of mitochondrial small subunit ribosomal RNA-encoding gene in scleractinian corals" *Marine Biotechnology* (2000) 2:146-153.

Chen et al., "A universal PCR primer to detect members of the Potyviridae and its use to examine the taxonomic status of several members of the family" *Archives of Virology* (2001) 146:757-766.

Chen, Y. Z. et al., "A BAC-Based STS-Content Map Spanning a 35-Mb Region of Human Chromosome 1p35-36," Genomics (2001) 74(1):55-70.

Chen, N. et al., "The genomic sequence of ectromelia virus, the causative agent of mousepox," *Virology* (2003) 317:165-186.

Chen et al., "Genetic mapping of the cold-adapted phenotype of B/Ann Arbor/1/66, the master donor virus for live attenuated influenza vaccines (FluMist)" Virology (2006) 345:416-423.

Chen, Ch, K. Tang, N. Taranenko and S. Allman, "Laser Desorption Mass Spectrometry for Fast DNA Sequencing," (Nov. 1994), http://www.ornl.gove/sci/techresources/Human_Genome/publicat/94SANTA/sequencing/seqtoc.shtml ('787 reexamination).

Chmielewicz, B. et al., "Development of a PCCR-Based Assay for Detection, Quantification, and Genotyping of Human Adenoviruses," Clin. Chem., 2005, vol. 51, No. 8, pp. 1365-1373.

Cho et al., "Application of the ribonuclease P (RNase P) RNA gene sequence for phylogenetic analysis of the gene Saccharomonospora" *International Journal of Systematic Bacteriology* (1998) 48:1223-1230.

Choi et al., "Detection and subtying of swine influenza H1N1, H1N2 and H3N2 viruses in clinical samples using two multiplex RT-PCR assays" J. Virol. Methods (2002) 102:53-59.

Choi, S. et al., "Real-Time PCR Quantification of Human Adenoviruses in Urban Rivers Indicates Genome Prevalence but Low Infectivity," Appl. Environ. Microbiol., 2005, vol. 71, No. 11, pp. 7426-7433.

Christel, LA et al., "Rapid, Automated Nucleic Acid Probe Assays Using Silicon Microstructures for Nucleic Acid Concentration" J. Biomech. Eng., 1999, 121, 22-27.

Claas, E.C.J. et al., "Internally Controlled Real-Time PCT Monitoring of Adenovirus DNA Load in Serum or Plasma of Transplant Recipients," J. Clin. Microbiol., 2005, vol. 43, No. 4, pp. 1738-1744.

Cloney, L. et al., "Rapid detection of *mecA* in methicillin resistant *Stuphylococcus aureus* using cycling probe technology," *Mol. Cell Probes* (1999) 13:191-197.

Conrads et al., "16S-23S rDNA internal transcribed spacer sequences for analysis of the phylogenetic relationships among species of the genus Fusobacterium" *International Journal of Systematic and Evolutionary Microbiology* (2002) 52:493-499.

Contreras-Salazar et al. "up regulation of the Epstein-Barr virus (EBV)-encoded membrane protein LMP in the Burkitt's lymphoma line Daudi after exposure to n-Butyrate and after EBV superinfection" J. Virol. (1990) 64(11):5441-5447.

Cornel et al., "Polymerase chain reaction species diagnostic assay for Anopheles quadrimaculatus cryptic species (Diptera: Culicidae) based on ribosomal DNA ITS2 sequences" *Journal of Medical Entomology* (1996) 33:109-116.

Couto, I. et al., "Devetopment of Methicillin Resistance in Clinical Isolates of *Staphylococcus sciuri* by Transcriptional Activation of the *mecA* Homologue Native to the Species," *J. Bacteriol*. (2003) 185(2):645-653.

Crain et al., "Applications of mass spectrometry of the characterization of oligonucleotides and nucleic acids" *Curr. Opin. Biotechnol*. (1998) 9:25-34.

Crawford-Miksza, L.K. et al., "Analysis of 15 Adenovirus Hexon Proteins Reveals the Location and Structure of Seven Hypervariable Regions Containing Serotype-Specific Residues," J. Virol., 1996, vol. 70, No. 3, pp. 1836-1844.

Crawford-Miksza, L.K. et al., "Adenovirus Serotype Evolution is Driven by Illegitimate Recombination in the Hypervariable Regions of the Hexon Protein," Virol., 1996, vol. 224, pp. 357 367.

Crawfor-Miksza et al., "Strain variation in adenovirus serotypes 4 and 7a causing acute respiratory disease." (1999) 37:1107-1112.

Crespillo et al., "Mitochondrial DNA sequences for 118 individuals from northeastern Spain" Int J. Legal Med. (2000) 114:130-132.

Cui, L. et al., "Contribution of a Thickened Cell Wall and Its Glutamine Nonamidated Component to the Vancomnycin Resistance Expressed by *Staphylococcus aureus* Mu50," Antimicrob. Agents Chemother. (2000) 44(9):2276-2285.

Dasen et al., "Classification and identification of Propionibacteria based on 16S ribosomal RNA genes and PCR" *Systematic and Applied Microbiology* (1998) 21:251-259.

De Sousa, M. A. et al., "Bridges from hospitals to the laboratory: genetic portraits of methicillin-resistant *Staphylococcus aureus* clones," FEMS Immunol. Med. Microbiol. (2004) 40:101-111.

Deforce et al., "Analysis of oligonucleotides by ESI-MS" *Advances in Chromatography* (2000) 40:539-566.

Deforce et al., "Characterization of DNA Oligonucleotides by Coupling of Capillary Zone Electrophoresis to Electrospray Ionization Q-TOF Mass Spectrometry" *Analytical Chemistry* (1998) 70:3060-3068.

De Jong, J.C. et al., "Adenoviruses from Human Immunodeficiency Virus-Infected Individuals, Including Two Strains That Represent New Candidate Serotypes Ad50 and Ad51 of Species B1 and D, Respectively," J. Clin. Microbiol., 1999, vol. 37, No. 12, pp. 3940-3945.

De La Puente-Redondo et al., "Comparison of different PCR approaches for typing of *Francisella tularensis* strains." (2000) 38:1016-1022.

Del Blanco et al., "Genotyping of *Francisella tularensis* strains by pulsed-field gel electrophoresis, amplified fragment length polymorphism fingerprinting, and 16S rRNA gene sequencing." (2002) 40:2964-2972.

Del Vecchio, V. G. et al., "Molecular Genotyping of Methicillin—Resistant *Staphylococcus aureus* via Fluorophore-Enhanced Repetitive-Sequence PCR," J. Clin. Microbiol. (1995) 33(8):2141-2144.

Demesure et al., "A set of universal primers for amplification of polymorphic non-coding regions of mitochondrial and chloroplast DNA in plants" *Molecular Ecology* (1995) 4:129-131.

Denis et al., "Development of a semiquantitative PCR assay using internal standard and colorimetric detection on microwell plate for pseudorabies virus" Mol. Cell. Probes (1997) 11(6):439-448.

Deurenberg et al., "Rapid detection of Panton-Valentine leukocidin from clinical isolates of *Staphylococcus aureus* strains by real-time PCR" FEMS Microbiol. Lett. (2004) 240(2):225-228.

Deurenberg et al., "The prevalence of the *Staphylococcus aureus* tst gene among community-and hospital-acquired strains and isolates from Wegener's Granulomatosis patients" FEMS Microbiol. Lett. (2005) 245:185-189.

Dias Neto et al., "Shotgun sequencing of the human transcriptome with ORF expressed sequence tags" *PNAS* (2000) 97:3491-3496.

Di Guilmi, A.M. et al., "Human adenovirus serotype 3 (Ad3) and the Ad3 fiber p[protein bind to a 130-kDa membrane protein on HeLa cells," Virus Res., 1995, vol. 38, pp. 71-81.

Diep, B. A. et al., "Complete genome sequence of USA300, an epidemic clone of community acquired meticillin-resistant *Staphylococcus aureus*," Lancet (2006) 367:731-739.

Dinauer et al., "Sequence-based typing of HLA class II DQB1" *Tissue Anigens* (2000) 55:364-368.

Ding et al., "A high-throughput gene expression analysis technique using competitive PCR and matrix-assisted laser desorption ionization time-of-flight MS" PNAS (2003) 100(6):3059-3064.

Donehower, et al., "The use of primers from highly conserved pol regions to identify uncharacterized retroviruses by the polymerase chain reaction," J. Vir. Methods (1990) 28:33-46.

Donofrio et al., "Detection of influenza A and B in respiratory secretions with the polymerase chain reaction" PCR methods and applications, Cold Spring Harbor Lab. Press vol. 1, No. 4, (1992) pp. 263-268.

Doty et al., Proc. Natl. Acad. Sci. USA 46:461 (1960).

Drosten et al., New England Journal of Medicine, 2003, 348, 1967.

Dubernet et al., "A PCR-based method for identification of *Lactobacilli* at the genus level" FEMS Microbiology Letters (2002) 214:271-275.

EBI Accession No. AEM14131 (Jan. 11, 2007)—Bacterial DNA PCR Primer SEQ ID No. 874.

Ebner, K. et al., "Molecular Detection and Quantitative Analysis of the Entire Spectrum of Human Adenoviruses by a Two-Reaction Real-Time PCR Assay," J. Clin. Microbiol., 2005, vol. 43, No. 7, pp. 3049-3053.

Ebner et al., "Typing of human adenoviruses in specimens of immunosuppressed patients by PCR-fragment length analysis and real-time quantitative PCR" Journal of Clinical Microbiology (2006) 44:2808-2815.

Echavarria, M. et al., "PCR Method for Detection of Adenovirus in Urine of Healthy and Human Immunodeficiency Virus-Infected Individuals," J. Clin. Microbiol., 1998, vol. 36, No. 11, pp. 3323-3326.

Echavarria, M. et al., "Detection of Adenoviruses (AdV) in Culture-Negative Environmental Samples by PCR During an AdV-Associated Respiratory Disease Outbreak," J. Clin. Microbiol., 2000, vol. 38, No. 8, pp. 2982-2984.

Echavarria, M. et al., "Prediction of severe disseminated adenovirus infection by serum PCR," Lancet, 2001, vol. 358, pp. 384-385.

Echavarria, M. et al., "Rapid Detection of Adenovirus in Throat Swab Specimens by PCR During Respiratory Disease Outbreaks among Military Recruits", J. Clin. Microbiol., 2003, vol. 41, No. 2, pp. 810-812.

Echavarria, M. et al., "Use of PCR to demonstrate of Adenovirus Species B, C, of F as Well as Coinfection with Two Adenovirus Species in Children with Flu-Like Symptoms", J. Clin. Microbiol, 2006, vol. 44, No. 2, pp. 625-627.

Ecker et al., "Rapid identification and strain-typing of respiratory pathogens for epidemic surveillance" PNAS (2005) 102(22):8012-8017.

Ecker et al., "The Ibis T5000 Universal Biosensor: An Automated Platform for Pathogen Identification and Strain Typing" JALA (2006) 11:341-351.

Edwards, K.M. et al., "Adenovirus Infections in Young Children", Pediatrics, 1985, vol. 76, No. 3, pp. 420-424.

Ellis et al., "Molecular diagnosis of influenza" Rev. Med. Virol. (2002) 12(6):375-389.

Elnifro et al., "PCR and Restriction Endonuclease Analysis for Rapid Identification of Adenovirus Subgenera" *Journal of Clinical Microbiology* (2000) 38:2055-2061.

Elsayed, S. et al., "Development and Validation of a Molecular Beacon Probe-Based Real-Time Polymerase Chain Reaction Assay for Rapid Detection of Methicillin Resistance in *Staphylococcus aureus*," Arch. Pathol. Lab. Med. (2003) 127:845-849.

EMBL Accession No. S90302, Human, Muscle, Mitochondrial Mutant, 22 nt, segment 2 of 2 (XP002436791) Nov. 26, 1993.

EMBL Accession AJ552897 (Mar. 29, 2003).

EMBL Accession AR321656 (Aug. 12, 2003).

EMBL Accession L15697 (Mar. 4, 2000).

EMBL Accession AB068711 (May 21, 2003).

EMBL Accession Z48571 (Jun. 9 1995).

Enright, M. C, et al., "Multilocus Sequence Typing for Characterization of Methicillin-Resistant and Methicillin-Susceptible Clones of *Staphylococcus aureus*," J. Clin. Microbial. (2000) 38(3): 1008-1015.

Enright, M. C. et al., "The evolutionary history of methicillin-resistant *Staphylococcus aureus* (MRSA)," PNAS(2002) 99(11): 7687-7692.

Enright, M. C. et al., "The evolution of a resistant pathogen—the case of MRSA," Curr. Opin. Pharmacol. (2003) 3:474-479.

Enright, M.C., et al., "Multilocus Sequence Typing of *Streptococcus pyogenes* and the Relationships between emm Type and Clone" Infection and Immunity, 2001, 69, 2416-2427.

Eremeeva et al., "Evaluation of a PCR Assay for Quantitation of *Rickettsia rickettsii* and Closely Related Spotted Fever Group Rickettsiae" J. Clin. Microbiol. (2003) 41(12):5466-5472.
Erlich (ed.). PCR Technology, Stockton Press (1989).
Esmans et al., "Liquid Chromatography-Mass Spectrometry in Nucleoside, nucleotide and modified nucleotide characterization" *J. of Chromatography A* (1998) 794:109-127.
Evans & Wareham, "Practical Algorithms for Universal DNA Primer Design: An Exercise in Algorithm Engineering", 2001.
European Patent Office Communication 96(2) EPC for 02709785.6 dated Nov. 20, 2006.
European Patent Office Communication 94(3) EPC for 02709785.6 dated Nov. 4, 2009.
European Patent Office Communication for 06849755.1 dated Mar. 12, 2008.
European Patent Office Communication for 07760292.8 dated Apr. 7, 2009.
European Search Report for 02709785.6 dated Oct. 10, 2005.
European Supplemental Search Report for 03796752.8 dated Aug. 14, 2007.
European Supplemental Search Report for 03810055.8 dated Jul. 9, 2007.
European Supplemental Search Report for 02709785.6-2405 (PCT/US0206763) dated Oct. 12, 2005.
European Supplemental Search Report for 04752257.8 dated Feb. 15, 2006.
European Supplemental Search Report for 05751872.2 dated Jan. 28, 2008.
European Supplemental Search Report for 05753037 dated Aug. 28, 2009.
European Supplemental Search Report for 05856582.1 dated Nov. 10, 2008.
European Supplemental Search Report for 04775904.8 dated Jul. 25, 2008.
Facklam, R., et al., "emm Typing and Validation of Provisional M Types for Group A *Streptococci*" (1999) Emerging Infectious Diseases, 5, 247-253.
Fang, H. et al., "Rapid Screening and Identification of Methicillin-Resistant *Staphylococcus aureus* from Clinical Samples by Selective-Broth and Real-Time PCR Assay," *J. Clin. Microbial.* (2003) 41 (7):2894-2899.
Farlow et al., "*Francisella tularensis* Strain Typing Using Multiple-Locus, Variable-Number Tandem Repeat Analysis" Journal of Critical Microbiology, (2001) 39(9):3186-3192.
Farrell, D. J., "The Reliability of Microscan Conventional and Rapid Panels to Identify *Staphylococcus aureus* and Detect Methicillin Resistance: an Evaluation Using the Tube Coagulase Test and *mec* A PCR," *Pathology* ( 1 997) 29:406-410.
Fedele C G et al., "Multiplex polymerase chain reaction for the simultaneous detection and typing of polyomavirus JC, BK, and SV40 DNA in clinical samples", Journal of Virological Methods, 82(2), Oct. 1999, pp. 137-144.
Fedele C G et al., "Quantitation of polyomavirus DNA by a competitive nested polymerase chain reaction," Journal of Virological Methods, 88(1):51-61 (Jul. 2000).
Feng, P., "Impact of molecular biology on the detection of food pathogens" Mol. Biotechnol., 1997, 7, 267-278.
Figueiredo et al., "Identification of Brazilian flaviviruses by a simplified reverse transcription-polymerase chain reaction method using Flavivirus universal primers" *American Journal of Tropical Medicine and Hygiene* (1998) 59:357-362.
Flora, et al., "Dual-micro-ESI source for precise mass determination on a quadrupole time-of-flight mass spectrometer for genomic and proteomic applications" *Anal. Bioanal. Chem.* (2002) 373:538-546.
Fong, W. K., et al., "Rapid Solid-Phase Immunoassay for Detection of Methicillin-Resistant *Staphylococcus aureus* Using Cycling Probe Technology." *J. Clin. Microbiol.* (2000) 38(7): 2525-2529.
Fox et al., "Identification and Detection of Bacteria: Electrospray MS-MS Versus Derivatization/GC-MS" *Proceedings of the ERDEC Scientific Conference on Chemical and Biological Defense Research* (1994) 39-44.
Fox et al., "Identification of Brucella by Ribosomal-spacer-region PCR and differentiation of, *Brucella canis* from other *Brucella* spp. pathogenic for humans by carbohdrate profiles" *Journal of Clinical Microbiology* (1998) 36:3217-3222.
Fox et al., "Report of the 'Bioterrorism Workshop' Duke University Thomas Center on Apr. 24, 2002 organized by US Army Research Office" *Journal of Microbiological Methods* (2002) 51:247-254.
Fox, J.P. et al., "The Virus Watch Program: A Continuing Surveillance of Viral Infections in Metropolitan New York Families", Am. J. Epidemiol., 1969, vol. 89, No. 1, pp. 25-50.
Francois et al. "Sequence-specific recognition and cleavage of duplex DNA via triple-helix formation by oligonucleotides covalently linked to a phenanthroline-copper chelate" Proc. Natl. Acad. Sci. USA (1989) 86:9702-9706.
Francois, P. et al., "Rapid Detection of Methicillin-Resistant *Staphylococcus aureus* Directly from Sterile or Nonsterile Clinical Samples by a New Molecular Assay," *J. Clin. Microbiol.* (2003) 41(1):254-260.
Fraser et al., "The Minimal Gene Complement of Mycoplasma Genitalium" *Science* (1995) 270:397-403.
Freiberg et al. Genome-wide mRNA profiling: impact on compound evaluation and target identification in anti-bacterial research. Targets 1(1):20-29 (2002).
Freymuth et al., "Comparison of Multiplex PCR Assays and Conventional Techniques for the Diagnostic of Respiratory Virus Infections in Children Admitted to Hospital with an Acute Respiratory Illness" J. Med. Virol. (2006) 78(11):1498-1504.
Freymuth, F. et al., "Detection of respiratory syncytial virus, parainfluenzavirus 3, adenovirus and rhinovirus sequences in respiratory tract of infants by polymerase chain reaction and hybridization", Clin. Dian. Virol, 1997, vol. 8, pp. 31-40.
Fuerstenau et al., "Molecular Weight Determination of Megadalton DNA Electrospray Ions Using Charge Detection Time-of-flight Mass Spectrometry" *Rapid Comm. Mass Spec.* (1995) 9:1528-1538.
Fujimoto, T. et al., "Single-Tube Multiplex PCR for Rapid and Sensitive Diagnosis of Subgenus B and Other Subgenera Adenoviruses in Clinical Samples", Microbiol. Immunol., 2000, vol. 44, No. 10, pp. 821-826 (abstract only).
Fujimura, S, et al., "Characterization of the *mupA* Gene in Strains of Methicillin-Resistant *Staphylococcus aureus* with a Low Level of Resistance to Mupirocin," *Antimicrob. Agents Chemother.* (2001) 45(2):641-642.
Fujimura, S. et al., "Isoleucyl-tRNA Synthetase Mutations in *Staphylococcus aureus* Clinical Isolates and in Vitro Selection of Low-Level Mupirocin-Resistant Strains," *Antimicrob. Agents Chemother.* (2003) 47(10): 3373-3374.
Fujioka et al., "Analysis of enterovirus genotypes using single-strand conformation polymorphisms of polymerase chain reaction products" *J. Virol. Meth.* (1995) 51:253-258.
Gabriel et al., "Improved mtDNA sequence analysis of forensic remains using a "mini-primer set" amplification strategy" *Journal of Forensic Sciences* (2001) 46:247-253.
Gall, J.G.D. et al., "Construction and Characterization of Hexon-Chimeric Adenoviruses: Specification of Adenovirus Serotype", J. Virol, 1998, vol. 72, No. 12, pp. 10260-10264.
Gammelin et al., "Two Subtypes of Nucleoproteins (NP) of Influenza A Viruses" Virology (1989) 170:71-80.
Garcia et al., "Quantitative Real-Time PCR Detection of Rift Valley Fever Virus and Its Application to Evaluation of Antiviral Compounds" J. Clin. Microbiol. (2001) 39(12):4456-61.
Garcia-Martinez et al. "Use of the 16s-23s ribosomal genes spacer region in studies of prokaryotic diversity" Journal of Microbiological Methods (1999) 36:55-64.
Gattermann et al., "Heteroplasmic Point Mutations of Mitochondrial DNA Affecting Subunit I of Cytochrome c Oxidase in Two Patients with Acquired Idiopathic Sideroblastic Anemia" *Blood* (1997) 90:4961-4972.
Gaydos, C.A. et al., "Adenovirus Vaccines in the U.S. Military", Military Med., 1995, vol. 160, No. 6, pp. 300-304.
Geha et al., "Multiplex PCR for Identification of Methicillin-Resistant Staphylococci in the Clinical Laboratory" J. Clin. Microbiol. (1994) 32:1768-1772.
GenBank Accession No. NC_000913, Jan. 16, 1997.
GenBank accession No. AE009948.1 (gi:22535226; Aug. 8, 2002).
GenBank accession No. AE009949.1 (gi:19913450; Apr. 3, 2002).

GenBank accession No. AE015927.1 (gi:28204652; Feb. 4, 2003).
GenBank accession No. AE015929.1 (gi:27316888; Jan. 2, 2003).
GenBank accession No. AF274728 (gi:11612419; Dec. 11, 2000).
GenBank accession No. AF276257.1 (gi:1457889; Jul. 1, 2001).
Genbank Accession AF304460 (Jul. 11, 2001).
Genbank Accession No. M21150 Apr. 26, 1993.
Genbank Accession No. AF375051.1 (Jun. 26, 2001).
GenBank Accession No. BX571857.1 (gi:49243355; Jun. 25, 2004).
Genbank Accession No. Z48571 (Jun. 9, 1995).
Genbank Accession No. X84646 (Jul. 2, 1995).
GenBank GI:147581 [online] Sep. 14, 1992 [retrieved on Jul. 20, 20091 from http://www.ncbi.nlm.nih.gov/sviewer/viewer.fqi?I47581:OLDID:114614.
Genbank GI:15922990 [online] Oct. 4, 2001 [retrieved on Jun. 22, 2008] retrieved from: http://www.ncbi.nlm.nih.gov/entrez/viewer.fcgi?I5922990:OLD08:50885 (pp. 1, 12, 15, 148, 216, 476, 722, 723, 725, 881, 1251).
Genbank GI:18542231 [online] Sep. 16, 2003 [retrieved on Jun. 23, 20081 retrieved from http://www.ncbi.nlm.nih.gov/entrez/viewer.fcgi?db=nuccore&id=I8542231 (2 pages).
GenBank GI:174375 [online] Aug. 11, 1995 [retrieved on Jul. 20, 20091 retrieved from http://www.ncbi.nlm.nih.gov/nuccore/I74375.
Genbank GI:21281729 [online], publicly available at least as of May 31, 2002 [retrieved on Apr. 11, 20081, retrieved from: http://www.ncbi.nlm.nih.gov/entrez/viewer.fcgi?21281729:OLD11:599579 (pp. 1, 723 and 1137).
GenBank GI:42813 [online] Feb. 28, 1992 [retrieved on Jul. 20, 2009] retrieved from the Internet at http://www.ncbi.nlm.nih.gov/sviewer/viewer.fqi?42813:OLDID:25896.
GenBank GI:49243355 [online] Jun. 24, 2004 [retrieved on Jul. 27, 2009] retrieved from http://www.ncbi.nlm.nih.govlsviewer/viewer.fi?49243355:OLDO4:1481434.
GenBank GI:73916349 [online] Sep. 30, 2005 [retrieved on Jul. 25, 2009] retrieved from http://www.ncbi.nlm.nih.gov/nuccore/73916349.
GenBank GI:78099429 [online] Mar. 11, 2006 [retrieved on Jul. 22, 20091 retrieved from http://www.ncbi.nlm.nih.gov/sviewer/viewer.fi?78099429:NCBI:I2971731.
Gendel et al., "Computational analysis of the specificity of 16S rRNA-derived signature sequences for identifying food-related microbes" Food Microbiology (1996) 13:1-15.
Gibb et al., "Development and evaluation of a 5' fluorogenic nuclease assay to detect and differentiate between Ebola Virus subtypes Zaire and Sudan", Journal of Clinical Microbiology, 39(11):4125-4130 (Nov. 2001).
Gilbert et al., "Comparison of commercial assays for the quantitation of HBV DNA load in health care workers: calibration differences" J. Virol. Methods (2002) 100(1-2):37-47.
Giles et al., "Maternal inheritance of human mitochondrial DNA," PNAS (1980) 77:6715-6719.
Gill, S. R. et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," *J. Bacteriol.* (2005) 187(7): 2426-2438.
Gilliland et al., "Analysis of cytokine mRNA and DNA: detectionf and quantitation by competitive polymerase chain reaction" PNAS (1990) 87(7):2725-2729.
Ginther et al., "Identifying individuals by sequencing mitochondrial DNA from teeth," *Nature Genetics* (1992) 2:135-138.
Gjoen et al., "Specific detection of coxsackie viruses A by the polymerase chain reaction" Clinical and Diagnostic Virology (1997) 8:183-188.
Golden et al., Pilot Study of COBAS PCR and Ligase Chain Reaction for Detection of Rectal Infections Due to *Chlamydia trachomatis*, J. Clin. Microbiol., 41(5):2174-2175 (May 2003).
Goto et al., "Applications of the partial 16S rDNA sequence as an index for rapid identification of species in the genus *Bacillus" J. Gen. Appl. Microbiol.* (2000) 46:1-8.
Gravet et al., "Characterization of a novel structural member, LukE-LukD, of the bi-component staphylococcal leucotoxins family" FEBS Lett. (1998) 436(2):202-208.

Gray, G.C. et al., "Adult Adenovirus Infections: Loss of Orphaned Vaccines Precipitates Military Respiratory Disease Epidemics", Clin. Infect. Diseases, 2000, vol. 31, pp. 663-670.
Greenberg et al., "Intraspecific nucleotide sequence variability surrounding the origin of replication in human mitochondrial DNA," *Gene* (1983) 21:33-49.
Griffey et al., "Detection of base pair mismatches in duplex DNA and RNA oligonucleotides using electrospray mass spectrometry" *Proceedings of SPIE—The International Society for Optical Engineering* (1997) 2985:82-86.
Griffin et al., "Direct genetic analysis by matrix-assisted laser desorption/ionization mass spectrometry" PNAS (1999) 96:6301-6306.
Griffin et al., "Single-nucleotide polymorphism analysis by MALDI-TOF mass spectrometry" *Trends in Biotechnology* (2000) 18:77-84.
Grondahl, B. et al., "Rapid Identification of Nine Microorganisms Causing Acute Respiratory Tract Infections by Single-Tube Multiplex Reverse Transcription-PCR: Feasibility Study", J. Clin. Microbiol., 1999, vol. 37, No. 1, pp. 1-7.
Grundmann, H. et al., "Emergence and resurgence of meticillin—resistant *Staphylococcus aureus* as a public-health threat," Lancet (2006) 368: 874-885.
Grzybowski "Extremely high levels of human mitochondrial DNA heteroplasmy in single hair roots" *Electrophoresis* (2000) 21:548-553.
Gu, Z et al., "Multiplexed, Real-Time PCR for Quantitative Detection of Human Adenovirus", J. Clin. Microbiol., 2003, vol. 41, No. 10, pp. 4636-4641.
Guatelli et al., "Nucleic Acid Amplification in Vitro: Detection of Sequences with Low Copy Numbers and Application to Diagnosis of Human Immunodeficiency Virus Type 1 Infection" Clin. Microbiol. Rev. (1989) 2(2):217-226.
Haff et al., "Multiplex Genotyping of PCR Products with Mass Tag-Labeled Primers" Nucleic Acids Research (1997) 25(18):3749-3750.
Hahner et al., "Analysis of short tandem repeat polymorphisms by electrospray ion trap mass spectrometry" *Nucleic Acids Research* (2000) 28:E82.
Heim, A. et al., "Rapid and Quantitative Detection of Human Adenovirus DNA by Real-Time PCR", J. Med. Virol., 2003, vol. 70, pp. 228-239.
Haines, J.D., et al., "Medical response to bioterrorism: Are we prepared?" J. Okla. State Med. Assoc. 2000, 93, 187-196.
Hall et al., "Base composition analysis of human mitochondrial DNA using electrospray ionization mass spectrometry: a novel tool for the identification and differentiation of humans" Analytical Biochemistry (2005) 344:53-69.
Hamdad, F. et al., "Detection of Methicillin/Oxacillin Resistance and Typing in Aminoglycoside-Susceptible Methicillin-Resistant and Kanamycin-Tobramycin-Resistant Methicillin-Susceptible" *Microbial Drug Resistance* (2006) 12(3): 177-185.
Hamels et al., "Consensus PCR and Microarray for Diagnosis of the Genus *Staphylococcus*, Species, and Methicillin Resistance" BioTechniques (2001) 31(6):1364-1366.
Hammerle et al., "A sensitive PCR assay system for the quantitation of viral genome equivalents: hepatitis C virus (HCV)" Arch. Virol. (1996) 141:2103-2114.
Hannis et al., "Accurate characterization of the tyrosine hydroxylase forensic allele 9.3 through development of electrospray ionization Fourier transform ion cyclotron resonance mass spectrometry" *Rapid Communications in Mass Spectrometry* (1999) 13:954-962.
Hannis et al., "Detection of double-stranded PCR amplicons at the attomole level electrosprayed from low nanomolar solutions using FT-ICR mass spectrometry" *Fresenius Journal of Analytical Chemistry* (2001) 369: 246-251.
Hannis et al., "Genotyping short tandem repeats using flow injection and electrospray ionization Fourier transform ion cyclotron resonance mass spectrometry" *Rapid Communications in Mass Spectrometry* (2001) 15:348-350.
Hannis et al., "Genotyping complex short tandem repeats using electrospray ionization Fourier transform ion cyclotron resonance multistage mass spectrometry" *Proceedings of SPIE—The International Society for Optical Engineering* (2000) 3926:36-47.

Hanssen. A.M. et al., "SCC*mec* in staphylococci: genes on the move," *FEMS Immuol. Med. Microbiol.* (2006) 46:8-20.

Hassan et al., "Inter- and Intraspecies Variations of the 16S-23S rDNA Intergenic Spacer Region of Various Streptococcal Species" Systematic and Applied Microbiology (2003) 26(1):97-103.

Haugland et al., "Identification of putative sequence specific PCR primers for detection of the toxigenic fungal species *Stachybotrys chartarum*" *Mol. Cell. Probes* (1998) 12:387-396.

Hayashi et al., "Phylogenetic analysis of the human gut microbiota using 16S rDNA clone libraries and strictly anaerobic culture-based methods" *Microbiology and Immunology* (2002) 46:535-548.

Henchal et al., "Sensitivity and specificity of a universal primer set for the rapid diagnosis of dengue virus infections by polymerase chain reaction and nucleic acid hybridization" *American Journal of Tropical Medicine and Hygiene* (1991) 45:418-428.

Herrmann et al., "Differentiation of *Chlamydia* spp. By Sequence Determination and Restriction Endonuclease Cleavage of RNase P RNA Genes" *J. Clin. Microbiol*. (1996) 34:1897-1902.

Higgins et al., "Competitive oligonucleotide single-base extension combined with mass spectrometric detection for mutation screening" *BioTechniques* (1997) 23:710-714.

Higgins, J.A., et al., Sensitive and Rapid Identification of Biological Threat AgentsHIGGINS et al., "Competitive oligonucleotide single-base extension combined with mass spectrometric detection for mutation screening" BioTechniques (1997) 23:710-714. *Ann. NY Acad. Sci.*, 1999, 894, 130-148.

Hill, F., et al., "Polymerase recognition of synthetic oligodeoxyribonucleotides incorporating degenerate pyrimidine and purine bases," Proc. Natl. Acad. Sci. USA 95:4258-4263 (1998).

Hiramatsu, K. et al., "The emergence and evolution of methicillin-resistant *Staphylococcus aureus*." *Trends Microbiol.* (2001) 9(10):486-493.

Hoffmann et al., "Rescue of influenza B virus from eight plasmids" *PNAS* (2002) 99:11411-11416.

Hoffmann et al., "Universal primer set for the full-length amplification of all influenza A viruses" *Archives of Virology* (2001) 146:2275-2289.

Hofstadler et al., "TIGER: the universal biosensor" Inter. J. Mass Spectrom. (2005) 242:23-41.

Hodgson et al. Molecular Characterization of the Gene Encoding High-Level Mupirocin Resistance in *Staphylococcus aureus* J2870. Antimicrobial Agents and Chemotherapy 38(5):1205-1208, May 1994.

Holden, M. T. G. et al., "Complete genomes of two clinical *Staphylocuccus aureus* strain: Evidence for the rapid evolution of virulence and drug resistance," *PNAS* (2004) 101(26):9786-9791.

Holland et al., "Mitochondrial DNA Sequence Analysis of Human Skeletal Remains: Identification of Remains from the Vietnam War," *Journal of Forensic Sciences* (1993) 38:542-553.

Holland, M.M. and T.J. Parsons "Mitochondrial DNA analsysis_ Validation and use for forensic casework" (1999) Forensic Science Review, vol. 11, pp. 25-51.

Holm et al., "Removing near-neighbour redundancy from large protein sequence collections" *Bioinformatics* (1998) 14:423-429.

Holmes et al., "Whole-Genome Analysis of Human Influenza A Virus Reveals Multiple Persistent Lineages and Reassortment among Recent H3N2 Viruses" PLoS Biol. (2005) 3(9):1579-1589.

Honda et al., "Universal method of hypersensitive nested PCR toward forensic DNA typing" *International Congress Series* (1998) 7:28-30.

Hongoh et al., "Evaluation of primers and PCR conditions for the analysis of 16s rRNA genes from a natural environment" FEMS Microbiol. Lett. (2003) 221:299-304.

Hood, E., "Chemical and biological weapons: New questions, new answers" Environ. Health Perspect., 1999, 107:931-932.

Houng, H.-S. H. et al., "Rapid type-specific diagnosis of adenovirus type 4 infection using a hexon-based quantitative fluorogenic PCR", Diagn. Microbiol. Infect. Dis., 2002, vol. 42, pp. 227-236.

Howell et al., "Persistent Heteroplasmy of a Mutation in the Human mtDNA Control Region: Hypermutation as an Apparent Consequence of Simple-Repeat Expansion/Contraction" *Am. J. Hum. Genet*. (2000) 66:1589-1598.

Huber et al., On-line cation exchange for suppression of adduct formation in negative-ion electrospray mass spectrometry of nucleic acids. Anal. Chem. (1998) 70:5288-5295.

Huletsky, A. et al., New real-time PCR assay for rapid detection of methicillin-resistant *Staphylococcus aureus* directly from specimens containing a mixture of staphylococci. J. Clin. Microbial. (2004) 42(5): 1875-84.

Hung, "Detection of SARS coronavirus RNA in the cerebrospinal fluid of a patient with severe acute respiratory syndrome" Clin. Chem. (2003) 49:2108.

Hurdle, J. G. et al., "Analysis of Mupirocin Resistance and Fitness in *Staphylococcus aureus* by Molecular Genetic and Structural Modeling Techniques," *Antimicrob. Agents Chemother.* (2004) 48(11):4366-4376.

Hurst et al., "Detection of bacterial DNA polymerase chain reaction products by matrix-assisted laser desorption/ionization mass spectrometry" *Rapid Commun. Mass. Spec.* (1996) 10:377-382.

Hurst et al., "MALDI-TOF Analysis of Polymerase Chain Reaction Products from Methanotrophic Bacteria" *Anal. Chem.* (1998) 70:2693-2698.

Hutchison et al., "Maternal inheritance of mammalian mitochondrial DNA," *Nature* (1974) 251:536-538.

Hyde-Deruyscher, R. et al., "Polyomavirus early-late switch is not regulated at the level of transcription initiation and is associated with changes in RNA processing" Proc. Natl. Acad. Sci. USA (1988) 85:8993-8997.

Ieven, M. et al., "Rapid Detection of Methicillin Resistance in Coagulase-Negative Staphylococci by Commercially Available Fluorescence Test," *J. Clin. Microbiol*. (1995) 33(8):2183-2185.

Ihle et al., "Efficient purification of DNA fragments using a protein binding membrane" *Nucleic Acids Research* (2000) 28:e76.

Inglis, T. J. et al., "Rapid Genotypic Confirmation of Methicillin Resistance," *Pathology* (1996) 28(3):259-261.

Ingman et al., "Mitochondrial genome variation and the origin of modern humans" *Nature* (2000) 408:708-713.

Australian Search Report for AU 2003297687 dated Sep. 4, 2008.

Australian Search Report for AU 2003302236 dated Sep. 10, 2008.

Australian Search Report for AU 2004248107 dated Jul. 30, 2008.

Canadian patent office communication for Application No. 2,567,839 dated Apr. 7, 2009.

Canadian patent office communication for Application No. 2,525,498 dated Feb. 5, 2009.

Chinese Office Communication for CN2004800161.9 dated Jun. 12, 2009.

International Prelim. Exam. Report for PCT/US02/20336 dated May 12, 2004.

International Prelim. Exam. Report for PCT/US2005/033707 dated Mar. 20, 2007.

International Search Report for PCT/US02/20336 dated Feb. 3, 2003.

International Search Report for PCT/US02/20336 dated May 12, 2004.

International Search Report for PCT/US02/06763 dated Oct. 23, 2002.

International Search Report for PCT/US03/009802 dated Aug. 20, 2004.

International Search Report for PCT/US03/22835 dated Dec. 12, 2003.

International Search Report for PCT/US03/38757 dated Jun. 24, 2004.

International Search Report for PCT/US03/38795 dated Apr. 19, 2004.

International Search Report for PCT/US03/38830 dated Aug. 25, 2004.

International Search Report for PCT/US03/38505 dated Apr. 12, 2005.

International Search Report for PCT/US03/38761 dated Dec. 30, 2005.

International Search Report for PCT/US04/007236 dated Feb. 24, 2006.

International Search Report for PCT/US2004/011877 dated Apr. 20, 2006.

International Search Report for PCT/US04/012671 dated Sep. 28, 2007.

International Search Report for PCT/US04/015123 dated Oct. 3, 2005.
International Search Report for PCT/US04/015196 dated Jul. 1, 2005.
International Search Report for PCT/US2004/028869 dated Jul. 17, 2006.
International Search Report for PCT/US04/033742 dated May 15, 2006.
International Search Report for PCT/US2005/000386 dated May 9, 2006.
International Search Report for PCT/US05/005356 dated Aug. 7, 2007.
International Search Report for PCT/US05/007022 dated Oct. 20, 2006.
International Search Report for PCT/US2005/018031 dated Jun. 28, 2006.
International Search Report for PCT/US05/018337 dated Oct. 10, 2006.
International Search Report for PCT/US05/024799 dated Dec. 28, 2006.
International Search Report for PCT/US05/030058 dated Aug. 20, 2007.
International Search Report for PCT/US05/033707 dated Feb. 6, 2006.
International Search Report for PCT/US05/06133 dated Jul. 26, 2007.
International Search Report for PCT/US05/09557 dated Sep. 19, 2005.
International Search Report for PCT/US06/007747 dated Sep. 5, 2006.
International Search Report for PCT/US2006/040747 dated Mar. 17, 2009.
International Search Report for PCT/US06/015160 dated Oct. 10, 2006.
International Search Report for PCT/US2006/061307 dated Jan. 9, 2008.
International Search Report for PCT/US2007/020045 dated Jan. 8, 2009.
International Search Report for PCT/US2007/066194 dated Jan. 15, 2008.
International Search Report for PCT/US2008/054926 dated Jan. 26, 2009.
International Search Report for PCT/US2008/057717 dated Jan. 13, 2009.
International Search Report for PCT/US2008/064891 dated Aug. 28, 2008.
International Search Report for PCT/US2008/057901 dated Jun. 29, 2009.
International Search Report for PCT/US2008/065332 dated Nov. 28, 2008.
International Search Report for PCT/US2009/045635 dated Oct. 7, 2009.
Inyaku, K. et al., "Rapid Detection and Identification of Mycobacteria in Sputum Samples by Nested Polymerase Chain Reaction and Restriction Fragment Length Polymorphisms of dnaJ Heat Shock Protein Gene," 42 J. Med. Sci. 21-31 (1993) ('787 reexamination).
Isola et al., "MALDI-TOF mass spectrometric method for detection of hybridized DNA oligomers" *Analytical Chemistry* (2001) 73:2126-2131.
Iqbal et al., "A review of molecular recognition technologies for detection of biological threat agents" Biosensors & Bioelectronics, 15:549-578 (2000).
Ito, T. et al., "Structural Comparison of Three Types of Staphylococcal Cassette Chromosome *mec* Integrated in the Chromosome in Methicillin-Resistant *Staphylococcus aureus*," Antimicrob. Agents Chemother. (2001) 45(5): 1323-1336.
Ito, T. et al., "Insights on antibiotic resistance of Staphylococcus aureus from its whole genome: genomic istand SCC," *Drug Resist. Updat.* (2003) 6(1):41-52.
Jackson et al., "Mass spectrometry for genotyping: an emerging tool for molecular medicine" Molecular Medicine Today (2000) 6:271-276.

Jambrina et al., GenBank: AF005737.1 influenza B virus B/Panama/45/90 polymerase (PB2) mRNA, complete cds, (1997), pp. 1-3.
James et al., "Borelia lonestari infection after a bite by an Amblyomma americanum tick" The Journal of Infectious Diseases (2001) 183:1810-1814.
Jankowski et al., "Mass spectrometry of DNA. Part 2. Quantitative estimation of base composition" *European Journal of Mass Spectrometry in Biochemistry, Medicine, and Environmental Research* (1980) 1:45-52.
Jansen et al., "Genotype-by-environment Interaction in Genetic Mapping of Multiple Quantitative Trait Loci" *Theor. Appl. Genet.* (1995) 91:33-37.
Jaulhac, B. et al., "Specific detection of the toxic shock syndrome toxin-1 gene using the polymerase chain reaction" Mol. Cel. Probes (1991) 5:281-284.
Jaulhac, B. et al., "Synthetic DNA probes for detection of genes for enterotoxins A, B, C, D, E and for TSST-1 in staphylococcal strains," *J. Appl. Bacterial.* (1992) 72(5):386-392.
Jensen et al., "Rapid Identification of Bacteria on the Basis of Polymerase C+A409hain Reaction-Amplified Ribosomal DNA Spacer Polymorphisms" *Appl. Environ. Microbiol.* (1993) 59:945-952.
Jeong, J, et al., "Early Screening of Oxacillin-Resistant *Staphylococcus aureus* and *Staphylcoccus epidermidis* from Blood Culture," *J. Korean Med. Sci.* (2002) 17: 168-172.
Jiang et al., "Multiple Trait Analysis of Genetic Mapping for Quantitative Trait Loci Genetics" *Genetics* (1995) 140:1111-1127.
Jiang et al., "A highly efficient and automated method of purifying and desalting PCR products for analysis by electrospray ionization mass spectrometry." *Anal. Biochem.* (2003) 316:50-57.
Johansson et al., "Evaluation of PCR-based methods for discrimination of Francisella species and subspecies and development of a specific PCR that distinguishes the two major subspecies of *Francisella tularensis*." Journal of Clinical Microbiology (2000) 38:4180-4185.
Johnson et al. "Detection of genes for enterotoxins, exfoliative toxins, and toxic shock Syndrome toxin 1 in *Staphylococcus aureus* by the polymerase chain reaction" J. Clin. Microbiol. (1991) 29:426-430.
Johnson et al., "Precise molecular weight determination of PCR products of the rRNA intergenic spacer region using electrospray quadrupole mass spectroemtry for differentiation of *B. subtilis* and *B. atrophaeus*, closely related species of bacilli" *Journal of Microbiological Methods* (2000) 40:241-254.
Jonas, D. et al., "Rapid PCR-Based Identification of Methicillin-Resistant *Staphylococcus aureus* from Screening Swabs," *J. Clin. Microbiol.* (2002) 40(5): 1821-1823.
Jurinke C et al., "Application of nested PCR and mass specctrometry for DNA based virus detection: HBV-DNA detected in the majority of isolated anti-Hbc positive sera", Genetic Analysis: Biomolecular Engineering, Elsevier Science Publishing, US, 14(3):97-102 (Jan. 3, 1998)+A627+A661.
Jurinke et al., "Detection of hepatitis B virus DNA in serum samples via nested PCR and MALDI-TOF mass spectrometry" *Genetic Analysis: Biomolecular Engineering* (1996) 13:67-71.
Jurinke et al., "MALDI-TOF Mass Spectrometry. A Versatile Tool for High-Performance DNA Analysis" Molecular Biotechnology (2004) 26(2):147-163.
Kacian et al., "A Replicating RNA Molecule Suitable for a Detailed Analysis of Extracellular Evolution and Replication" Proc. Natl. Acad. Sci. USA 69:3038 (1972).
Kageyama et al., "Rapid detection of human fecal Eubacterium species and related genera by nested PCR method" *Microbiology and Immunology* (2001) 45:315-318.
Kajon, A.E. et al., "Genome Type Analysis of Brazilian Adenovirus Strains of Serotypes 1, 2, 3, 5, and 7 Collected Between 1976 and 1995", J. Med. Virol., 1999, vol. 58, pp. 408-412.
Katano, H., et al., "Identification of Adeno-associated virus contamination in cell and virus stocks by PCR", Biotechniques, Informa Life Sciences Publishing, Westborough, MA, US, 36(4):676-680 (Apr. 2004).
Katayama, Y. et al., "Genetic Organization of the Chromosome Region Surrounding *mecA* in Clinical Staphylococcal Strains: Role of IS431-Mediated mecI Deletion in Expression of Resistance in med-Canying, Low-Level Methicillin-Resistant *Staphylococcus haemolyticus*," Antimicrob. Agents Chemother. (2001) 45(7): 1955-1963.

Ke et al., "Development of a PCR Assay for Rapid Detection of Enterococci" *Journal of Clinical Microbiology* (1999) 37:3497-3503.

Kearns, A. M. et al., "Rapid detection of methicillin-resistant staphylococci by multiplex PCR," *J. Hosp. Infect.* (1999) 43:33-37.

Keller et al., "Empirical Statistical Model to Estimate the Accuracy of Peptide Identifications Made by MS/MS and Database Search" *Anal. Chem* (2002) 74:5383-5392.

Khan, A.S., et al., "An outbreak of Crimean-Congo haemorrhagic fever in the United Arab Emirates, 1994-1995" Am. J. Trop. Med. Hyg., 1997, 57, 519-525.

Khan, S. A. et al., "Simultaneous detection of erythromycin-resistant methylase genes *ermA* and *ermC* from *Staphylococcus* spp. By multiplex-PCR," *Mol. Cell Probes* (1999) 13:381-387.

Kidd, A.H. et al., "Rapid Subgenus Identification of Human Adenovirus Isolates by a General PPCR", J. Clin. Microbiol., 1996, vol. 34, No. 3, pp. 622-627.

Kilbourne, "Influenza Pandemics: Can We Prepare for the Unpredictable?" Viral Immunol. (2004) 17(3):350-357.

Kilbourne, "Influenza Pandemics of the 20th Century" Emerg. Infect. Dis. (2006) 12(1):9-14.

Kilpatrick et al., "Group-Specific Identification of Polioviruses by PCR Using Primer Containing Mixed-Base or Deoxyinosine Residues at Positions of Codon Degeneracy" *J. Clin. Microbiol.* (1996) 34:2990-2996.

Kim et al. "Identification of Mycobacterial species by comparative sequence analysis of the RNA polymerase gene (rpoB)" Journal of Clinical Microbiology 37(6):1714-1720, Jun. 1999.

Kitagawa et al. "Rapid diagnosis of methicillin-resistant *Staphylococcus aureus* bacteremia by nested polymerase chain reaction" Ann. Surgery (1996) 224:665-671.

Kolbert et al., "Branched-DNA Assay for Detection of the mecA Gene in Oxacillin-Resistant and Oxacillin-Sensitive Staphylococci" J. Clin. Microbiol. (1998) 36:2640-2644.

Krafft, A.E. et al., "Evaluation of PCR Testing of Ethanol-Fixed Nasal Swab Specimens as an Augmented Surveillance Strategy for Influenza Virus and Adenovirus Identification", J. Clin. Microbiol., 2005, vol. 43, No. 4, pp. 1768-1775.

Krahmer et al., "Electrospray quadrupole mass spectrometry analysis of model oligonucleotides and polymerase chain reaction products: determination of base substitutions, nucleotide additions/deletions, and chemical modifications" *Anal. Chem.* (1999) 71:2893-2900.

Krahmer et al., "MS for identification of single nucleotide polymorphisms and MS/MS for discrimination of isomeric PCR products" *Anal. Chem .* (2000) 72:4033-4040.

Kroes et al., "Bacterial diversity within the human subgingival crevice," Proc. Natl. Acad. Sci. USA (1999) 96:14547-14552.

Kresken, M. et al., "Prevalence of mupirocin resistance in clinical isolates of *Staphylococccus aureus* and *Staphylococcus epidermidis*: results of the Antimicrobial Resistance Surveillance Study of the Paul-Ehrlich-Society for Chemotherapy, 2001," Int. J. Antimicrob. Agents (2004) 23:577-581.

Krishnan, P.U. et al., "Detection of methicillin and mupirocin resistance in *Staphylococcus aureus* isolates using conventional and molecular methods: a descriptive study from a burns unit with high prevalence of MRSA," J. Clin. Pathol. (2002) 55:745-748.

Krossoy et al., "The putative polymerase sequence of infectious anemia virus suggests a new geneus within the Orthomyxoviridae" Journal of Virology (1999) 73:2136-2142.

Ksiaxek, Thomas G., et al., "A novel coronavirus associated with severe acute respiratory syndrome," New England Journal of Medicine, 348(20):1953-1966 (Apr. 10, 2003).

Kupke et al., "Molecular Characterization of Lantibiotic-synthesizing Enzyme EpiD Reveals a Function for Bacterial Dfp Proteins i Coenzyme A Biosynthesis" *Journal of Biological Chemistry* (2000) 275:31838-31846.

Kuroda, M., et al., "Whole genome Sequencing of meticillin-resistant *Staphylococcus aureus*", The Lancet, 357(9264):1225-1240 (Apr. 21, 2001).

Kwok, S. and R. Hguchi, "Avoiding false positives with PCR" Nature, 1989, 339,237-238.

Labandeira-Rey, M. et al., "*Staphylococcus aureus* Panton Valentine Leukocidin Causes Necrotizing Pneumonia" Sciencexpress Jan. 18, 2007.

Lacroix et al., "PCR-Based Technique for the Detection of Bacteria in Semen and Urine" *J. Microbiol. Meth* . (1996) 26:61-71.

Lacroix, L. et al., "Triplex Formation by Oligonucleotides Containing 5-(1-Propynyl)-2'- deoxyuridine: Decreased Magnesium Dependence and Improved Intracellular Gene Targeting" Biochem. (1999) 38(6):1893-1 901.

Lamb et al., "Sequence of Interrupted and Uninterrupted mRNAs and Cloned DNA Coding for the Two Overlapping Nonstructural Proteins of Influenza Virus" Cell (1980) 21:475-485.

Lau et al., "Nucleic acid sequence-based amplification methods to detect avian influenza virus" Biochem. Biophys. Res. Commun. (2004) 313:336-342.

Lau et al., "A real-time PCR for SARS-coronavirus incorporating target gene pre-amplification" Biochem. Biophys. Res. Comm. (2003) 312:1290-1296.

Lebedev, Y. et al "Oligonucleotides containing 2-aminoadenine and 5-methycytosine are more effective as primers for PCR amplification than their nonmodified counterparts" Genetic Analysis: Biomolecular Engineering (1996) 13:15-21.

Lednicky, J. A. et al., "Polyomaviruses and Human Tumors: A Brief Review of Current Concepnts and Interpretations," Front. Biosci. (1999) 4:d153-164.

Lee, J.A. et al., "Rapid Identification of Human Adenovirus Types 3 and 7 from Respiratory Specimens via Multiplex Type-Specific PCR", J. Clin. Microbiol., 2005, vol. 43, No. 11, pp. 5509-5514.

Leif et al., "Isolation and characterization of the proton-translocating NADH: ubiquinone oxidoreductase from *Escherichia coli" Eur. J. Biochem.* (1995) 230:538-548.

Lengyel, A. et al., "Characterization of the Main Protein Components of Adenovirus Virion and its Possible Use in Laboratory Diagnostics", Acta Microbiol. Immunol. Hung., 1998, vol. 45, Nos. 3-4; pp. 281-283.

Leroy et al., "Diagnosis of Ebola haemorrhagic fever by RT-PCR in an epidemic setting", Journal of Medical Virology, 60:463-467 (2000).

Levi, K. et al., "Evaluation of an Isothermal Signal Amplification Method for Rapid Detection of Methicillin-Resistant *Staphylococcus aureus* from Patient-Screening Swabs," J. Clin. Microbiol. (2003) 41(7):3 187-3191.

Levine et al., "PCR-based detection of *Bacillus anthracis* in formalin-fixed tissue from a patient receiving ciprofloxacin" Journal of Clinical Microbiology (2002) 40(11):4360-4362.

Levison et al., "Recent developments of magnetic beads for use in nucleic acid purification" Journal of Chromatography (1998) a 816:107-111.

Lewers et al., "Detection of Linked QTL for Soybean Brown Stem Rot Resistance in 'BSR 101' as Expressed in a Growth Chamber Environment" *Molecular Breeding* (1999) 5:33-42.

Le Cann et al., "Quantification of human astroviruses in sewage using real-time RT-PCR" Res. Microbiol. (2004) 155(1):11-15.

Li, Q.-G. et al., "Analysis of 15 Different Genome Types of Adenovirus Type 7 Isolated on Five Continents", J. Virol., 1986, vol. 60, No. 1, pp. 331-335.

Li, Q.-G. et al., "Comparison of 17 Genome Types of Adenovirus Type 3 Identified among Strains Recovered from Six Continents", J. Clin. Microbiol, 1988. vol. 26, No. 5, pp. 1009-1015.

Li, Q.-G. et al., "Genetic variability of hexon loops 1 and 2 between seven genome types of adenovirus serotype 7", Arch. Virol., 1999, Vol. 144, No. 9, pp. 1739-1749.

Li et al., "Screening of the high yield influenza B virus on MDCK cell and cloning of its whole genome" International Congress Series 1263 (2004) 610-614.

Li et al., "Single nucleotide polymorphism determination using primer extension and time of flight mass spectrometry" *Electrophoresis* (1999) 20:1258-1265.

Li et al., "Evolution of H9N2 influenza viruses from domestic poultry in Mainland China" Virology (2005) 340:70-83.

Liebermann, H. et al., "Mapping of linear epitopes on fibre knob of human adenovirus serotype 5", Virus Res., 2001, vol. 73, No. 2, pp. 145-151.
Liebermann, H. et al., "Mapping of Epitopes on the Fiber Knobs of Human Adenovirus Serotypes 8 and 15", Intervirology, 2002, vol. 45, pp. 59-66.
Lim et al., "The microRNAs of Caenorhabditis elegans" Genes and Development 17:991-1008 (2003).
Limbach, P.A., et al., "Enzymatic Sequencing of Oligonucleotides with Electrospray Mass Spectrometry" 42nd ASMS Conference on Mass Spectrometry (Jun. 1994) ('787 reexamination).
Limoncu, M. H. et al., "Emergence of phenotypic resistance to ciprofloxacin and levofloxacin in methicillin-resistant and methicillin-sensitive Staphylococcus aureus strains," Int. J. Antimicrob. Agents (2003) 21:420-424.
Lin et al., "Oxidative Damage to Mitochondrial DNA in Atrial Muscle of Patients with Atrial Fibrillation," Free Radical Biology and Medicine, 35(10):1310-1318 (2003).
Lin, B. et al., "Use of Oligonucleotide Microarrays for Rapid Detection and Serotyping of Acute Respiratory Disease-Associated Adenoviruses", J. Clin. Microbiol., 2004, vol. 42, No. 7, pp. 3232-3239.
Lina, G. et al., "Involvement of Panton-Valentine Leukocidin-Producing Staphylococcus aurues in Primary Skin Infections and Pneumonia," Clin. Infect. Dis. (1999) 29(5):1128-1132.
Lina, G. et al., "Bacterial Competition for Human Nasal Cavity Colonization: Role of Staphylococcal agr Alleles," Appl. Environ. Microbiol. (2003) 69(1):18-23.
Little, et al., "Rapid Sequencing of Oligonucleotides by High-Resolution Mass Spectrometry" J. Am. Chem. Soc. (1994) 116:4893-4897.
Little et al., "Maldi on a Chip: Analysis of Arrays of Low-Femtomole to Subfemtomole Quantities of Synthetic Oligonucleotides and DNA Diagnostic Products Dispensed by a Piezoelectric Pipet" Analytical Chemistry (1997) 69:4540-4546.
Liu et al., "An unusual gene arrangement for the putative chromosome replication origin and circadian expression of dnaN in Synechococcus sp. Strain PCC 7942" Gene (1996) 172:105-109.
Liu et al., "Improving the microdialysis procedure for electrospray ionization mass spectrometry of biological samples" Journal of Mass Spectrometry (1997) 32:425-431.
Liu et al., "Interregional Transmission of the Internal Protein Genes of H2 Influenza Virus in Migratory Ducks from North America to Eurasia" Virus Genes (2004) 29(1):81-86.
Livermore, D. M., "The threat from the pink corner," Ann. Med. (2003) 35(4):226-234.
Loakes et al., "Nitroindoles as universal bases" Nucleosides and Nucleotides (1995) 14:1001-1003.
Loo, J. A et al., "Applying Charge Discrimination with Electrospray Ionization-Mass Spectrometry to Protein Analysis," J. Am. Soc. Mass. Spectrom. (1995) 6:1098-1104.
Lott, "Nucleotide Sequence Analysis of the 5-8s rDNA and Adjacent ITS2 Region of Candida albicans and Related Species" Yeast, 9:1199-1206 (1999).
Louie, L. et al., "Evaluation of Three Rapid Methods for Detection of Methicillin Resistance in Staphylococcus aureus," J. Clin. Microbiol. (2000) 38(6):2170-2173.
Love et al., "Cloning and sequence of the groESL heat-shock operon of Pasteurella multocida" Gene (1995) 166:179-180.
Lovseth, A. et al., "Modified Multiplex PCR Method for Detection of Pyrogenic Exotoxin Genes in Staphylococcal Isolates," J. Clin. Microbiol. (2004) 42(8):3869-3872.
Lu, X. et al., "Molecular typing of human adenoviruses by PCR and sequencing of a partial region of the hexon gene", Arch. Virol.,., 2006, vol. 15, No. 8, pp. 1587-1602.
Ludwig W. "Bacterial phylogeny based on 16s and 23s rRNA sequence analysis" FEMS Microbiol Rev 15(2-3):155-73, Oct. 1994.
Ludwig, S.L. et al., "Prevalence of Antibodies to Adenovirus Serotypes 4 and 7 among Unimmunized US Army Trainees: Results of Retrospective Nationwide Seroprevalence Survey", J. Infect. Dis., (1998) 178, pp. 1776-1778.
Lukashov, V. V. et al., "Evolutionary Relationships among Parvoviruses: Virus-Host Coevolution among Autonomous Primate Parvoviruses and Links between Adeno-Associated and Avian Parvoviruses," J. Virol. (2001) 75(6):2729-2740.
Ma, X. X. et al., "Novel Type of Staphylococcal Cassette Chromosome mec Identified in Community-Acquired Methicillin-Resistant Staphylococcus aureus Strains," Antimicrob. Agents Chemother. (2002) 46(4):1147-1152.
Mack and Sninsky, "A sensitive method for the identification of uncharacterized viruses related to known virus groups: Hepadnavirus model system," Proc. Natl. Acad. Sci. USA (1988) 85:6977-6981.
Maiwald et al., "Characterization of contaminating DNA in Taq polymerase which occurs during amplification with a primer set for Legionella 5S ribosomal RNA" Molecular and Cellular Probes (1994) 8:11-14.
Malasig, M.D. et al., "Simplified Microneutralization Test for Serotyping Adenovirus Isolates", J. Clin. Microbiol., 2001, Vol. 39, No. 8, pp. 2984-2986.
Mangrum et al., "Solution composition and thermal denaturation for the production of single-stranded PCR amplicons: piperdine-induced destabilization of the DNA duplex?" Journal of the American Society for Mass Spectrometry (2002) 13:232-240.
Manian, F. A,, "Asymptomatic Nasal Carriage of Mupirocin-Resistant, Methicillin-Resistant Staphylococcus aureus (MRSA) in a Pet Dog Associated with MRSA Infection in Household Contacts," Clin. Infect. Dis. (2003) 36:e26-e28.
Marmur et al., "Strand Separation and Specific Recombination in Deoxyribonucleic Acids: Biological Studies" Proc. Natl. Acad. Sci. USA 46:453 (1960).
Martemyanov et al., "Extremely Thermostable Elongation Factor G from Aquifex aeolicus: Cloning, Expression, Purification, and Characterization in a Heterologous Translation System" Protein Expr. Purif. (2000) 18:257-261.
Martineau, F. et al., "Species-Specific and Ubiquitous-DNA-Based Assays for Rapid Identification of Staphylococcus aureus," J. Clin. Microbial. (1998) 36(3):618-623.
Martineau, F. et al., "Development of a PCR Assay for Identification of Staphylococci at Genus and Species Levels," J. Clin. Microbial. (2001) 39(7):2541-2547.
Martin-Lopez, J. V. et al., "Simultaneous PCR detection of ica cluster and methicillin and mupirocin resistance genes in catheter-isolated Staphylococcus," Int. Microbial. (2004) 7:63-66.
Mason et al., "Diversity and linkage of replication and mobilisation genes in Bacillus rolling circle-replicating plasmids from diverse geographical origins" FEMS Microbiol. Ecol. 2002, 42:235-241.
Matray et al., "Synthesis and properties of RNA analogs—oligoribonucleotide N3'->P5' phosphoramidates" Nucleic Acids Res (1999) 3976-3985.
Matsuoka, M. et al., "Characteristic expression of three genes, msr(A), mph(C) and erm(Y), that confer resistance to macrolide antibiotics on Staphylococcus aureus," FEMS Microbiol. Lett. (2003) 220:287-293.
May "Percent sequence identity: the need to be explicit" Structure (2004) 12(5):737-738.
McCabe et al., "Bacterial Species Identification after DNA Amplification with a Universal Primer Pair" Molecular Genetics and Metabolism (1999) 66:205-211.
McLafferty et al., "Comparison of Algorithms and Databases for Matching Unknown Mass Spectra" J. Am. Soc. Mass Spectrom. (1998).
McLuckey, S.A., et al., "Ion Trap Tandem Mass Spectrometry Applied to Small Multiply Charged Oligonucleotides with a Modified Base," 5 J. Am. Soc. Mass. Spectrom. 1994 5:740-747.
Mehrotra et al., "Multiplex PCR for detection of genes for Staphylococcus aureus enterotoxins, exfoliative toxins, toxic shock syndrome toxin 1, and methicillin resistance", Journal of Clinical Microbiology, Washington, DC US 38(3):1032-1035 (Mar. 1, 2000)+A256.
Meiyu et al., "Detection of flaviviruses by reverse transcriptase-polymerase chain reaction with the universal primer set" Microbiology and Immunology (1997) 41:209-213.
Mellor et al., "Genotype Dependence of Hepatitis C Virus Load Measurement in Commercially Available Quantitative Assays" J. Clin. Microbiol. (1999) 37(8):2525-2532.

Merlino, J. et al., "New Chromogenic Identification and Detection of *Staphylococcus aureus* and Methicillin-Resistant *S. aureus*." J. Clin. Microbiol (2000) 38(6): 2378-2380.

Merlino, J. et al., "Rapid Detection of Non-Multidrug-Resistant and Multidrug-Resistant Methicillin-Resistant *Staphylococcus aureus* Using Cycling Probe Technology for the mecA Gene," Eur. J. Clin. Microbiol. Infect. Dis. (2003) 22: 322.323.

Messmer et al., "Discrimination of *Streptococcus pneumoniae* from other upper respiratory tract streptococci by arbitrarily primed PCR" *Clinical Biochemistry* (1995) 28:567-572.

Metzgar, D. et al., "PCR Analysis of Egyptian Respiratory Adenovirus Isolates, Including Identification of Species, Serotypes and Coinfections", J. Clin. Microbiol., 2005, vol. 43, No. 11, p. 5743-5752.

Miller et al., "A compendium of human mitochondrial DNA control region: development of an international standard forensic database," Croat Med. J. (2001) 42:315-327.

Miragaia, M. et al., "Genetic Diversity among Methicillin-Resistant *Staphylococcus epidemidis* (MRSE)," Microbial Drug Resistance (2005) 11(2):83-93.

Miura-Ochiai. R. et al., "Quantitative detection and rapid identification of human adenoviruses", J. Clin. Microbiol., 2007, vol. 45, No. 3, pp. 958-967.

Mollet et al. "rpoB sequence analysis as a novel basis for bacterial identification" Molecular Microbiology 26(5):1005-1011 (1997).

Moore et al., "Development and Evaluation of a Real-Time Nucleic Acid Sequence Based Amplification Assay for Rapid Detection of Influenza A" J. Med. Virol. (2004) 74(4):619-628.

Moricca et al., "Detection of Fusarium oxysporum f.sp. Vasinfectum in cotton tissue by polymerase chain reaction" *Plant Pathology* (1998) 47:486-494.

Morinaga, N. er al., "Purification, Cloning and Charactarizarion of Variant LukE-LukD with Strong Leukocidal Activity of Staphylococcal Bi-Component Leukotoxin Family," Microbiol. Immunol. (2003) 47(1):81-90.

Morse et al., "Nucleotide Sequence of Part of the ropC Gene Encoding the B Subunit of DNA-Dependent RNA Polymerase from some Gram-Positive Bacteria and Comparative Amino Acid Sequence Analysis" *System Appl. Microbiol.* (1996) 19:150-157.

Muddiman et al., "Application of secondary ion and matrix-assisted laser desorption-ionization time-of-flight mass spectrometry for the quantitative analysis of biological molecules" *Mass Spectrometry Reviews* (1995) 14:383-429.

Muddiman et al., "Important aspects concerning the quantification of biomolecules by time-of-flight secondary-ion mass spectrometry" *Applied Spectroscopy* (1996) 50:161-166.

Muddiman et al., "Sequencing and Characterization of Larger Oligonucleotides by Electrospray Ionization Fourier Transform Ion Cyclotron Resonance Mass Spectrometry" *Reviews in Analytical Chemistry* (1998) 17:1-68.

Muddiman et al., "Precise mass measurement of a double-stranded 500 base-pair (309 kDa) polymerase chain reaction product by negative ion electrospray ionization fourier transform ion cyclotron resonance mass spectrometry" *Rapid Commun. Mass Spec.* (1999) 13:1201-1204.

Muhammad et al., "Electrospray ionization quadrupole time-of-flight mass spectrometry and quadrupole mass spectrometry for genotyping single nucleotide substitutions in intact polymerase chain reaction products in K-ras and p53" *Rapid Commun. Mass Spectrom* . (2002) 16:2278-2285.

Murakami, K. et al., "Identification of Methicillin-Resistant Strains of Staphylococci by Polymerase Chain Reaction," J. Clin. Microbiol. (1991) 29(10):2240-2244.

Mushegian et al., "A minimal gene set for ceullular life derived by comparison of complete bacterial genomes" Proc. Natl. Acad. Sci. USA (1996) 93:10268-10273.

Na et al., "Detection and typing of respiratory adenoviruses in a single-tube multiplex polymerase chain reaction" Journal of Medical Virology (2002) 66:512-517.

Nagpal et al., "Utility of 16S-23S RNA spacer region methodology: how similar are interspace regions within a genome and between strains for closely related organisms?" *Journal of Microbiological Methods* (1998) 33:211-219.

Nagy, M. et al., "Sequence Analysis of Porcine Adenovirus Serotype 5 Fibre Gene: Evidence for Recombination", Virus Genes, 2002, vol. 24, No. 2, pp. 181-185.

Nakagawa et al., "Gene sequences and specific detection for Panton-Valentine leukocidin" Biochem. Biophys. Res. Commun. (2005) 328(4):995-1002.

Nakao et al., "Development of a Direct PCR Assay for Detection of the Diphtheria Toxin Gene" *J. Clin. Microbiol.* (1997) 35:1651-1655.

Narita et al., "Phage conversion of Panton-Valentine leukocidin in *Staphylococcus aureus*: molecular analysis of a PVL-converting phage, phiSLT" Gene (2001) 268(1-2):195-206.

Naumov et al., "Discrimination of the Soil Yest Species Williopsis saturnus and Williopsis suaveolens by the Polymerase Chain Reaction with the Universal Primer N21" *Microbiology* (Moscow)(Translation of Mikrobiologiya) (2000) 69:229-233.

Neumann et al., "Host Range Restriction and Pathogenicity in the Context of Influenza Pandemic" Emerg. Infect. Dis. (2006) 12(6):881-886.

New England Biolabs (NEB) Catalog (1998-1999) pp. 1, 79, 121, 284.

Newcombe et al. "PCR of peripheral blood for diagnosis of meningococcal disease" (1996) 34:1637-1640.

Ng et al., "Serial analysis of the plasma concentration of SARS coronavirus RNA in pediatric patients with severe acute respiratory syndrome" Clin. Chem. (2003) 49:2085.

Ng et al., "Quantitative analysis and prognostic implication of SARS coronavirus RNA in the plasma and serum of patients with severe acute respiratory syndrome" Clin. Chem. (2003) 49:1976-1980.

Nilsson et al., "Evaluation of mitochondrial DNA coding region assays for increased discrimination in forensic analysis" *Forensic Science International: Genetics* (2008) 2:1-8.

Nishikawa et al., "Reconstitution of active recombinant Shiga toxin (Stx)1 from recombinant Stxl-A and Stxl-B subunits independently produced by *E. coli* clones" FEMS (1999) 178:13-18.

Norder et al., "Typing of Hepatitis B Virus Genomes by a Simplified Polymerase Chain Reaction" *J. Med. Virol.* (1990) 31:215-221.

Nordhoff, E., et al., "Matrix Assisted Laser Desorption/Ionization Mass Spectrometry of Nucleic Acids with Wavelengths in the Ultraviolet and Infrared" 6 Rapid Commun. Mass Spectrom. 771-776 (1992) ('787 reexamination).

Nubel et al., "PCR primers to amplify 16S rRNA genes from Cyanobacteria," Applied and Environmental Microbiology, 63(8):3327-3332 (Aug. 1997).

Null et al., "Preparation of single-stranded PCR products for electrospray ionization mass spectrometry using the DNA repair enzyme lambda exonuclease" *Analyst* (2000) 125:619-626.

Null et al., "Genotyping of Simple and Compound Short Tandem Repeat Loci Using Electrospray Ionization Fourier Transform Ion Cyclotron Resonance Mass Spectrometry" Analytical Chemistry (2001) 73:4514-4521.

Null et al., "Perspectives on the use of electrospray ionization Fourier transform ion cyclotron resonance mass spectrometry for short tandem repeat genotyping in the post-genome era" *Journal of Mass Spectrometry* (2001) 36:589-606.

Null et al., "Evaluation of sample preparation techniques for mass measurements of PCR products using ESI-FT-ICR mass spectrometry" *Journal of the American Society for Mass Spectrometry* (2002) 13:338-344.

Null et al., "Determination of a correction to improve mass measurement accuracy of isotopically unresolved polymerase chain reaction amplicons by electrospray ionization Fourier transform ion cyclotron resonance mass spectrometry" *Rapid Comm. Mass Spectrom*. (2003) 17:1714-1722.

Null et al., "Implications of hydrophobicity and free energy of solvation for characterization of nucleic acids by electrospray ionization mass spectrometry" *Anal. Chem.* (2003) 75:1331-1339.

Nunes, E. L. et al., "Detection of ileS-2 Gene Encoding Mupirocin Resistance in Methicillin-Resistant *Staphvlococcus aureus* bv Multiplex PCR" Diagn. Microbiol. Infect. Dis. (1999) 34(2): 77-81.

Nygren et al., "Quantification of HIV-1 Using Multiple Quantitative Polymerase Chain Reaction Standards and Bioluminometric Detection" Anal. Biochem. (2001) 288(1):28-38.

Oberacher H et al., "Increased foresnic efficiency of DNA fingerprints through simultaneous resolution of length and nucleotide variability by high-performance mass spectrometry," Human Mutation 29(3):427-432 (Mar. 2008)+A613+A714.

Oberacher et al., "Analysis of polymerase chain reaction products by on-line liquid chromatography-mass spectrometry for genotyping of polymeric short tandem repeat loci" (2001) 73:5109-5115.

Oberste, et al., "Molecular phylogeny and proposed classification of the Simian picornaviruses," J. Virol. (2002) 76:1244-1251.

Oberste, et al., "Improved molecular identification of enteroviruses by RT-PCR and amplicon sequencing," J. Clin. Virol. (2003) 26:375-377.

Oberste, et al., "Molecular epidemiology and type-specific detection of echovirus 11 isolates from the Americas, Europe, Africa, Australia, southern Asia and the Middle East," Virus Res. (2003) 91:241-248.

Oizumi, N, et al., "Relationship between mutations in the DNA gyrase and topoisomerase IV genes and nadifloxacin resistance in clinically isolated quinolone-resistant *Staphylococcus aureus*," Journal of Infection and Chemotherapy: Official Journal of the Japan Society of Chemotherapy, 7(3):191-194 (Sep. 2001).

Okada, M. et al., "Detection and sequence-based typing of human adenoviruses using sensitive universal primer sets for the hexon gene", Arch. Virol., 2007, vol. 152, No. 1, pp. 1-9.

Okuma, K. et al., "Dissemination of New Methicillin-Resistant *Staphylococcus aureus* Clones in the Community," J. Clin. Mcrobiol. (2002) 40(11):4289-4294.

Oliveira, D. C. et al., "Genetic Organization of the Downstream Region of the mecA Element in Methicillin-Resistant *Staphylococcus aureus* Isolates Carrying Different Polymorphisms of This Region," Antimicrob. dients Chemother. (2000) 44(7): 1906-1910.

Oliveira, D. C. et al., "Multiplex PCR Strategy for Rapid Identification of Structural Types and Variants of the mec Element in Methicillin—Resistant *Staphylococcus aureus*," Antimicrob. Agents Chemother. (2002) 46(7):2155-2161.

Olsen et al. "Transhemispheric exchange of Lyme disease spyrochetes by seabirds" Journal of Clinical Microbiology (1995) 33:3270-3274.

Osiowy, C. et al., "Direct Detection of Respiratory Syncytial Virus, Parainfluenze Virus, and Adenovirus in Clinical Respiratory Specimens by a Multiplex Reverse Transcription-PCR Assay", J. Clin. Microbiol., 1998, vol. 36, No. 11, pp. 3149-3154.

Ostrander, E. A. et al., "Identification and Characterization of Dinucleotide Repeat (CA)n Markers for Genetic Mapping in Dog," Genomics (1993) 16(1):207-213.

Ounissi, H. et al., "Gene Homogeneity for Aminoglycoside-Modifying Enzymes in Gram-Positive Cocci," Antimicrob. Agents Chemother. (1990) 34(11):2164-2168.

Pan, Z.-Q et al., "Oligonucleotide-targeted degradation of U1 and U2 snRNAs reveals differential interactions of simian virus 40 pre-mRNAs with snRNPs," Nucleic Acids Res. (1989) 17(16):6553-6568.

Pannetier et al., "Quantitative titration of nucleic acids by enzymatic amplification reactions run to saturation" (1993) 21:577-583.

Parson et al., "Population data for 101 Austrian Caucasian mitochondrial DNA d-loop sequences: Application of mtDNA sequence analysis to a forensic case" *Int J. Legal Med.* (1998) 111:124-132.

Paterson et al., "Fine Mapping of Quantitative Trait Loci Using Selected Overlapping Recombinant Chromosomes, in an Interspecies Cross of Tomato" *Genetics* (1990) 124:735-742.

Pawa, A. et al., "Co-transfer of plasmids in association with conjugative transfer of mupirocin or mupirocin and penicillin resistance in methicillin-resistant *Staphylococcus aureus*;" J. Med. Microbiol. (2000) 49: 1103-1107.

Payne et al. Antimicrobials: The challenge of antibiotic resistant bacterial pathogens: the medical need, the market and prospects for new antimicrobial agents. Current Opinion in Microbiology 7:435-438 (2004).

Peng et al., "Rapid detection of Shigella species in environmental sewage by an immunocapture PCR with universal primers" *Applied and Environmental Microbiology* (2002) 68:2580-2583.

Perez-Roth, E. et al., "Multiplex PCR for Simultaneous Identification of *Staphylococcus aureus* and Detection of Methicillin and Mupirocin Resistance," J. Clin. Microbial. (2001) 39(11):4037-4041.

Peters et al., "Quantification of the detection of Pneumocystis carinii by DNA amplification" Mol. Cell. Probes (1992) 6:115-117.

Pieles, U, et al., Matrix-Assisted Laser Desorption Ionization Time-of-Flight Spectrometry: A Powerful Tool for the Mass and Sequence Analysis of Natural and Modified Oligonucleotides 21 Nucleic Acids Res. 3191-3196 (1993) ('787 reexamination).

Pillai, S.D., :Rapid molecular detection of microbial pathogens: breakthroughs and challenges Arch Virol., 1997, 13 Suppl., 67-82.

Piper, J. et al., "Commercially Available Technique for Rapid Laboratory Detection of Methicillin Resistance Among *Staphylococcus aureus*," Diagn. Microbial. Infect. Dis. (1988) 11(3): 177-180.

Poddar, S.K., "Detection of adenovirus using PCR and molecular beacon", J. Virol. Methods., 1999, vol. 82, No. 1, pp. 19-26.

Pomerantz et al., "Determination of oligonucleotide composition from mass spectrometrically measured molecular weight" *Journal of the American Society for Mass Spectrometry* (1993) 4:204-209.

Pring-Akerblom, P., et al., "PCR-based detection and typing of human adenoviruses in clinical samples", Res. Virol., 1997, vol. 148, No. 3, pp. 225-231.

Pring-Akerblom, P., et al., "Multiplex Polymerase Chain Reaction for Subgenus-Specific Detection of Human Adenoviruses in Clinical Samples", J. Med. Virol., 1999, vol. 58, No. 1, pp. 87-92.

Promega T4 Polynucleotide Kinase, Promega Technical Bulletin No. 519, Jul. 2002.

Puthavathana et al., "Molecular characterization of the complete genome of human influenza H5N1 virus isolates from Thailand" J. Gen. Virol. (2005) 86:423-433.

Qadri, S. M. et al., "Rapid Detection of Methicillin-Resistant *Staphylococcus aureus* by Crystal MRSA ID System,"J. Clin. Microbiol. (1994) 32(7):1830-1832.

Raaum, R. L. et al., "Catarrhine primate divergence dates estimated from complete mitochondrial genomes: concordance with fossil and nuclear DNA evidence," J. Hum. Evol. (2005) 48:237-257.

Ramisse et al., "Identification and characterization of Bacillus anthracis by multiplex PCR analysis of sequences on plasmids pX01 and pX02 and chromosomal DNA" FEMS Microbiology Letters (1996) 145(1):9-16.

Rangarajan, Sampath, et al., "Rapid identification of emerging infectious agents using PCR and electrospray ionization mass spectrometry" Ann. N.Y. Acad. Of Sci (2007) 1102:109-120.

Reid et al., "Primary diagnosis of foot-and-mouth disease by reverse transcription polymerase chain reaction" *Journal of Virological Methods* (2000) 89:167-176.

Reilly et al., "Design and use of 16S ribosomal DNA-directed primers in competitive PCRs to enumerate proteolytic bacteria in the rumen" *Microb. Ecol.* (2002) 43:259-270.

Reischl, Frontiers Biosci., 1996, 1, Application of Molecular Biology-Based Methods to the Diagnosis of Infectious Diseases 1, e72-e77.

Reischl, U. et al., "Rapid Identification of Methicillin-Resistant *Staphylococcuss aureus* and Simultaneous Species Confirmation Using Real-Time Fluorescence PCR," J. Clin. Microbiol. (2000) 38(6):2429-2433.

Roberts, M.M. et al., "Three-Dimensional Structure of the Adenovirus Major Coat Protein Hexon", Science, 1986, vol. 232, No. 4754, pp. 1148-1151.

Robinson, D. A. et al., "Multilocus sequence typing and the evolution of methicillin-resistant *Staphylococcus aureus*," Clin. Microbiol. Infect. (2004) 10:92-97.

Rong et al., "Design and Application of 60mer oligonucleotide microarray in SARS coronavirus detection", Chinese Sci. Bull., 2003, 48, 1165-1169.

Ross et al., "Discrimination of Single-Nucleotide Polymorphisms in Human DNA Using Peptide Nucleic Acid Probes Detected by MALDI-TOF Mass Spectrometry" Anal. Chem . (1997) 69:4197-4202.

Ross et al., "Analysis of DNA fragments from conventional and microfabricated PCR devices using delayed extraction MALDI-TOF mass spectrometry" Anal. Chem. (1998) 70:2067-2073.

Ruan et al., Comparative full-length genome sequence analysis of 14 SARS coronavirus isolates and common mutations associated with the putative origins of infection, Lancet (2003) 361:1832.

Rota et al., "Sequencing of a cDNA clone of the nucleoprotein gene of influenza B/Ann Arbor/1/86" Nucleic Acids Research (1989) 17:3595.

Ruest et al., "Comparison of the Directigen Flu A+B test, the QuickVue Influenza Test, and Clinical Case Definition to Viral Culture and Reverse Transcription-PCR for Rapid Diagnosis of Influenza Virus Infection" J. Clin. Microbiol. (2003) 41(8):3487-3493.

Rupf et al., "Quantitative determination of *Streptococcus* mutans by using competitive polymerase chain reaction" Eur. J. Oral. Sci. (1999) 107(2):75-81.

Russell, K.L. et al., "Transmission Dynamics and Prospective Environmental Sampling of Adenovirus in a Military Recruit Setting", J. Infect. Dis., 2006, vol. 194, No. 7, pp. 877-885.

Sabat, A. et al., "Comparison of PCR-Based Methods for Typing *Staphylococcus aureus* Isolates," J. Clin. Microbiol. (2006) 44(10):3804-3807.

Sackesen, C. et al., "Use of polymerase chain reaction for detection of adenovirus in children with or without wheezing", Turk. J. Pediatr., 2005, vol. 47, No. 3, pp. 227-231.

Sakai, H. et al., "Simultaneous Detection of *Staphylococcus aureus* and Coagulase-Negative Staphylococci in Positive Blood Cultures by Real-Time PCR with Two Fluorescence Resonance Energy Transfer Probe Sets," J. Clin. Microbiol. (2004) 42(12):5739-5744.

Sala et al., "Ambiguous base pairing of the purine analogue 1-(20deoxy-B-D-ribofuranosyl)-imidazole-4-carboxamide during PCR" *Nucl. Acids Res.* (1996) 24:3302-3306.

Sambrook et al., Molecular Cloning: A Laboratory Manual, 2nd Edition, Cold Spring Harbor Press, Cold Spring Harbor, NY 1989.

Sampath et al., "Rapid Identification of Emerging Pathogens: Coronavirus" Emerg. Infect. Dis. (2005) 11(3):373-379.

Sampath et al "Global surveillance of emerging influenza virus genotypes by mass spectrometry" Plos ONE (2007) 5:e489.

Sampath et al "Rapid Identification of Emerging Infectious Agents Using PCR and Electrospray Ionization Mass Spectrometry" Ann. N.y. Acad. Sci. (2007) 1102:109-120.

Sanchez et al., "Detection and Molecular Characterizatio of Ebola viruses causing disease in human and nonhuman primates" The Journal of Infectious Diseases, 179(1):S164-S169 (1999).

Sanchez, J.L. et al., "Epidemic of Adenovirus-Induced Respiratory Illness Among US Military Recruits: Epidemiologic and Immunologic Risk Factors in Healthy, Young adults", J. Med. Virol., 2001, vol. 65, No. 4, pp. 710-718.

Santos et al. "Identification and phylogenetic sorting of bacterial lineages with universally conserved genes and proteins" Environmental Microbiology 6(7):754-759, Jul. 2004.

Sarantis, H. et al., "Comprehensive Detection and Serotyping of Human Adenoviruses by PCR and Sequencing", J. Clin. Microbial., 2004, vol. 42, No. 9, pp. 3963-3969.

Sauer et al., "A novel procedure for efficient genotyping of single nucleotide polymorphisms" *Nucleic Acids Research* (2000) 28:E13.1.

Scaramozzino et al., "Comparison of Flavivirus universal primer pairs and development of a rapid, highly sensitive heminested reverse transcription-PCR assay for detection of flaviviruses targeted to a conserved region of the NS5 gene sequences" *J. Clin. Microbiol.* (2001) 39:1922-1927.

Schabereiter-Gurtner et al "Application of broad-range 16s rRNA PCR amplification and DGGE fingerprinting for detection of tick-infecting bacteria" The Journal of Microbiological Methods (2003 52:251-260.

Scheffner, M. et al., "The E6 Oncoprotein Encoded by Human Papillomavirus Types 16 and 18 Promotes the Degradation of p53," Cell (1990) 63:1129-1136.

Schena M. "Genome analysis with gene expression microarrays" Bioessays (1996) 18:427-431.

Scheuermann et al. "Polymerase chain-reaction-based mRNA quantification Using an internal standard: analysis of oncogene expression" (1993) 218:446-473.

Schlecht, N. F. et al., "Viral Load as a Predictor of the Risk of Cervical Intraepithelial Neoplasia," Int. J. Cancer (2003) 103:519-524.

Schmidt et al., "Analysis of a marine pikoplankton community by 16s rRNA gene cloning and sequencing," J. Bacteriol. (1991) 173:4371-4378.

Schmitz, F. J. et al., "Specific information concerning taxonomy, pathogenicity and methicillin resistance of staphvlococci obtained bv a multiplex PCR." J. Med. Microbiol. (1997) 46:773-778.

Schmitz, F. J. et al., "Development of a multiplex-PCR for direct detection of the genes for enterotoxin B and C, and toxic shock syndrome toxin-1 in *Staphylococcus aureus* isolates," J. Med. Microbiol. (1998) 47(4):335-340.

Schmitz, F. J. et al., "Development of Resistance to Ciprofloxacin, Rifampin, and Mupirocin in Methicillin-Susceptible and -Resistant *Staphylococcus aureus* Isolates," Antimicrob. Agents Chemother. (2000) 44(11): 3229-3231.

Schram et al., "Mass Spectrometry of Nucleic Acid Components" *Biomedical Applications of Mass Spectrometry* (1990) 34:203-280.

Schultz et al., "Polymerase chain reaction products analyzed by charge detection mass spectrometry" *Rapid Communications in Mass Spectrometry* (1999) 13:15-20.

Schwartz, M, et al., "Prenatal diagnosis of alpha-1-antitrypsin deficiency using polymerase chain reaction (PCR). Comparison of conventional RFLP methods with PCR used in combination with allele specific oligonucleotides or RFLP analysis," 36 Clin. Genet. 419-426 (1989) ('787 reexamination).

Schweiger et al., "Application of a Fluorogenic PCR Assay for Typing and Subtyping of Influenza Viruses in Respiratory Samples" J. Clin. Microbiol. (2000) 38(4):1552-1558.

Sciacchitano et al., "Analysis of polymerase chain reaction-amplified DNA fragments of clostridium botulinum type E neurotoxin gene by high performance capillary electrophoresis." *J. Liq. Chromatogr. Relat. Technol.* (1996) 19:2165-2178.

Scott-Taylor, T.H. et al., "Conserved Sequences of the Adenovirus Genome for Detection of all Human Adenovirus Types by Hybridization", J. Clin. Microbiol., 1992, vol. 30, No. 7, pp. 1703-1710.

Seifarth, et al., "Rapid identification of all known retroviral reverse transcriptase sequences with a novel versatile detection assay," AIDS Res. Human Retrovir. (2000) 16:721-729.

Senko et al., "Determination of Monoisotopic Masses and Ion Populations for Large Biomolecules from Resolved Isotopic Distributions," *J. Am. Soc. Mass Spectrom.* (1995) 6:229.

Seshadri et al., "Differential Expression of Translational Elements by Life Cycle Variants of Coxiella burnetii" *Infect. Immun* . (1999) 67:6026-6033.

Shadan, F. F. et al., "n-Butyrate, a Cell Cycle Blocker, Inhibits the Replication of Polyomaviruses and Papillomaviruses but Not That of Adenoviruses and Herpesviruses," J. Virol. (1994) 68(8):4785-4796.

Shaver et al., "Variation in 16S-23S rRNA intergenic spacer regions among *Bacillus subtilis* 168 isolates" *Molecular Microbiology* (2001) 42:101-109.

Shaver et al., "Restriction fragment length polymorphism of rRNA operons for discrimination and intergenic spacer sequences for cataloging *Bacillus subtilis* sub-groups" *J. Microbiol Methods* (2002) 50:215-223.

Shi et al., "Design and application of 60mer oligonucleotide microarray in SARS coronavirus detection" Chinese Sci. Bull. (2003) 48:1165-1169.

Shimaoka, M. et al., "Development of Enzyme-Labeled Oligonucleotide Probe for Detection of mecA gene in Methicillin—Resistant *Staphylococcus aureus*," J. Clin. Microbiol (1994) 32(8): 1866-1869.

Shimaoka, M. et al., "Detection of the gene for toxic shock syndrome toxin 1 in *Staphylococcus aureus* by enzyme-labelled oligonucleotideprobes," J. Med. Microbiol. (1996) 44:215-218.

Shrestha, N. K. et al., "Rapid Identification of Staphylococcus aureus and the mecA Gene from BacT/Alert Blood Culture Bottles by Using the Lightcycler System," J. Clin. Microbiol. (2002) 40(1):2659-2661.

Simonsen et al., "The Impact of Influenza Epidemics on Hospitalizations" J. Infect. Dis. (2000) 181:831-837.

Skov, R L. et al., "Evaluation of a new 3-h hybridization method for detecting the mecA gene in *Staphylococcus aureus* and comparison with existing genotypic and phenotypic susceptibility testing methods," J. Antimicrob. Chemother. (1999) 43: 467-475.

Smirnov et al. "Application of DNA-binding polymers for preparation of DNA for analysis by matrix-assisted laser desorption/ionization mass spectrometry." Rapid Comm in Mass Spectrometry (2001) 15:1427-1432.

Smith and Waterman, Adv. Appl. Math., 1981, 2, 482-489.

Song et al., "Identification of cry11-type genes from *Bacilus thuringiensis* strains and characterization of a novel cry11-type gene" App. Environ. Microbiol. (2003) 69:5207-5211.

Spackman et al., "Development of a real-time reverse transcriptase PCR assay for type A influenza virus and the avian H5 and H7 hemagglutinin subtypes" Journal of Clinical Microbiology (2002) 40:3256-3260.

Spiess, et al., Trehalose is a potent PCR enhancer: Lowering of DNA melting temperature and thermal stabilization of Taq polymerase by the disaccharide trehalose, In: Clinical Chemistry, 2004, 50(7):1256-1259.

Srinivasan et al., "Matrix-assisted laser desorption/ionization time-of-flight mass spectrometry as a rapid screening method to detect mutations causing Tay-Sachs disease" *Rapid Communications in Mass Spectrometry* (1997) 11:1144-1150.

Steffens et al., "Sequence analysis of mitochondrial DNA hybervariable regions using infrared fluorescence detection" *BioTechniques* (1998) 24:1044-1046.

Stephensen CB et al., "Phylogenetic analysis of a highly conserved region of the polymerase gene from 11 coronaviruses and development of a consensus polymerase chain reaction assay" Virus Research Amsterdam NL, 60(2):181-189 (Apr. 1, 1999).

Stone et al., "Rapid detection and simultaneous subtype differentiation of influenza A viruses by real time PCR" (2004) *Journal of Virological Methods* (2004) 117:103-112.

Stoneking et al., "Population variation of human mDNA control region sequences detected by enzymatic amplification and sequence-specific oligonucleotide probes," American Journal of Human Genetics (1991) 48:370-382.

Stratagene, 1988 Catalog, p. 39.

Strommenger, B. et al., "Multiplex PCR Assay for Simultaneous Detection of Nine Clinically Relevant Antibiotic Resistance Genes in *Staphylococcus aureus*," J. Clin. Microbial. (2003) 41(9):4089-4094.

Stuhlmeier, R et al., "Fast, simultaneous, and sensitive detection of staphylococci," J. Clin. Pathol. (2003) 56:782-785.

Sumner et al. "PCR Amplification and Comparison of Nucleotide Sequences from the groESL Heat Shock Operon of Ehrlichia Species" Journal of Critical Microbiology (1997) 35:2087-2092.

Sundsfjord, A. et al., "Genetic methods for detection of antimicrobial resistance," APMIS (2004) 112:815-837.

Swanborg, R.H., "Human herpesvirus 6 and *Chlamydia pneumoniae* as etiologic agents in multiple sclerosis—a critical review" Microbes and Infection, 4:1327-1333 (2002).

Swaminathan, B., et al., Emerging Infectious Diseases, 2001, 7, 382-389.

Swenson, J. M. et al., "Perfomance of Eight Methods, Including Two New Rapid Methods, for Detection of Oxacillin Resistance in a Challenge Set of *Staphylococcus aureus* Organisms," J. Clin. Microbial. (2001) 39(10):3785-3788.

Takagaki, Y. et at., "Four factors are required for 3'-end cleavage of pre-mRNAs," Genes Dev. (1989) 3:1711-1724.

Takahashi et al., "Characterization of gryA, gryB, grIA and grIB mutations in fluoroquinolone-resistant clinical isolates of *Staphylococcus aureus*" *J. Antimicrob. Chemother* (1998) 41:49-57.

Takahata M, et al., "Mutations in the gyrA and grlA genes of quinolone-resistant clinical isolates of methicillin-resistant *Staphylococcus aureus*," The Journal of Antimicrobial Chemotherapy, 38(3):543-546 (Sep. 1996).

Takayama, R. et al., "Quantification of Adenovirus Species B and C Viremia by Real-Time PCR in Adults and Children Undergoing Stem Cell Transplantation", J. Med. Virol., 2007, vol. 79, No. 3, pp. 278-284.

Takeuchi et al., "Serotyping of Adenoviruses on Conjunctival Scrapings by PCR and Sequence Analysis" *Journal of Clinical Microbiology* (1999) 37:1839-1845.

Talaat et al., "Genome-directed primers for selective labeling of bacterial transcripts for DNA microarray analysis" *Nature Biotechnology* 17:676-682, 2000.

Tan, T.Y., "Use of molecular techniques for the detection of antibiotic resistance in bacteria," Expert. Rev. Mol. Diagn. (2003) 3(1):93-103.

Tanabe, F. et al., "The Properties and mec A Gene of the Methicillin-Resistant *Staphylccoccus aureus* Isolated in Fukushima Medical College Hospital," Fukushima J. Med. Sci (1993) 39(1):35-42.

Tang, K., "Matrix-Assisted Laser Desorption/Ionization Mass Spectrometry of Oligonucleotides," Dissertation submitted to the Faculty of Vanderbilt University (Aug. 1994) ('787 reexamination).

Tang, K, N.I. Taranenko, S.L. Allman, L.Y. Chang and C.H. Chen, "Double-Stranded DNA Analysis by Matrix Assisted Laser Desorption/Ionization," 42nd ASMS Conference on Mass Spectrometry (Jun. 1994) ('787 reexamination).

Tang, K, N.I. Taranenko, S.L. Allman, L.Y. Chang and C.H. Chen, "Detection of 500-Nucleotide DNA by Laser Desorption Mass Spectrometry," Rapid Commun. Mass Spectrom. (Sep. 1994) 8: 727-730.

Tatuch et al., "Heteroplasmic mtDNA mutation (T-G) at 8993 can cause Leigh disease when the percentage of abnormal mtDNA is high" *Am. J. Hum. Genet.* (1992) 50:852-858.

Tarassishin, L. et al., "Adenovirus core protein VII displays a linear epitope conserved in a range of human adenoviruses", J. Gen. Virol., 1999, vol. 80, pp. 47-50.

Tarassishin, L. et al., "An epitope on the adenovirus fibre tail is common to all human subgroups", Ach. Virol., 2000, vol. 145, pp. 805-811.

Taubenberger et al., "Characterization of the 1918 influenza virus polymerase genes" Nature (2005) 437:889-893.

Taylor, L.H., et al., Philos. Trans. R. Soc. Lond B. Biol. Sci. 2001, 356, 983-989.

Tenover, F. C. et al., "Characterization of a Strain of Community-Associated Methicillin-Resistant *Slaphylococcus aureus* Widely Disseminated in the United States," J. Clin.Microbiol. (2006) 44(1):108-118.

Teramura, T. et al., "Quantitative detection of serum adenovirus in a transplant recipient", Lancet, 2002, vol. 359, pp. 1945.

Thiel, et al., "Infectious RNA transcribed in vitro from a cDNA copy of the human coronavirus genome cloned in vaccinia virus" J. Gen. Virology 2001 82:1273-1281.

Thompson et al., "Influenza-Associated Hospitalizations in the United States" JAMA (2004) 292:1333-1340.

Thompson et al., "Clustal W: Improving the sensitivity of progressive multiple sequence alignment through sequence weighting, position-specific gap penalties and weight matrix choice" Nucleic Acid Res. (1994) 22:4673-80.

Tokue, Y. et al., "Comparison of a Polymerase Chain Reaction Assay and a Conventional Microbiologic Method for Detection of Methicillin-Resistant *Slaphylococcus aureus*," Antimicrob. Agents Chemother. (1992) 36(1):6-9.

Tong et al., "Ligation reaction specificities of an Nad+-dependent DNA ligase from the hyperthermophile Aquifex aeolicus" *Nucleic Acids Res* (2000) 28:1447-1454.

Top, F., Jr., "Control of Adenovirus Acute Respiratory Disease in U.S. Army Trainees", Yale J. Biol. Med., 1975, vol. 48, pp. 185-195.

Torroni et al., "Classification of European mtDNAs from an Analysis of Three European Populations" *Genetics* (1996) 144:1835-1850.

Towner, K. J. et al., "Development and evaluation of a PCR-based immunoassay for the rapid detection of methicillin-resistant *Staphylococcus aureus*," J. Med. Microbial. (1998) 47:607-613.

Tsuneyoshi et al., "Mass spectrometric gene diagnosis of one-base substitution from polymerase chain reaction amplified human DNA" (1997) 11:719-722.

Tsunoda et al., Time and Memory Efficient Algorithm for Extracting Palindromic and Repetitive Subsequences in Nucleic Acid Sequences Pacific Symposium on Biocomputing (1999) 4:202-213.

Udo, E. E. et al., "Rapid detection of methicillin resistance in staphylococci using a slide latex agglutination kit," Int. J Antimicrob. Agents. (2000) 15(1):19-24.

Udo, E. E. et al., "Genetic analysis of methicillin-resistant *Staphylococcus aureus* expressing high-and low-level mupirocin resistance." J. Med. Microbiol. (2001) 50:909-515.

Udo, E. E. et al., "A chromosomal location of the mupA gene in *Staphylococcus aureus* expressing high-level mupirocin resistance," J. Antimicrob. Chemother. (2003) 51:1283-1286.

Unal et al., "Detection of Methicillin-Resistant Staphylococci by Using the Polymerase Chain Reaction" J. Clin. Microbiol. (1992) 30:1685-1691.
Unpublished U.S. Appl. No. 10/318,463, filed Dec. 13, 2002.
Unpublished U.S. Appl. No. 10/323,186, filed Dec. 18, 2002.
Unpublished U.S. Appl. No. 10/323,187, filed Dec. 18, 2002.
Unpublished U.S. Appl. No. 10/324,721, filed Dec. 18, 2002.
Unpublished U.S. Appl. No. 10/728,486, filed Dec. 5, 2003.
Unpublished U.S. Appl. No. 11/209,439, filed Aug. 23, 2005.
Unpublished U.S. Appl. No. 11/233,630, filed Sep. 2, 2005.
Unpublished U.S. Appl. No. 11/682,259, filed Mar. 5, 2007.
Unpublished U.S. Appl. No. 60/604,329, filed Aug. 24, 2004.
Unpublished U.S. Appl. No. 60/632,862, filed Dec. 3, 2004.
Unpublished U.S. Appl. No. 60/639,068, filed Dec. 22, 2004.
Unpublished U.S. Appl. No. 60/648,188, filed Jan. 28, 2005.
Unpublished U.S. Appl. No. 60/658,248, filed Mar. 3, 2005.
Unpublished U.S. Appl. No. 90/010,209, filed Jun. 27, 2008.
Unpublished U.S. Appl. No. 90/010,210, filed Jun. 27, 2008.
Upton, A. et al., "Mupirocin and *Staphylococcus aureus*: a recent paradigm of emerging antibiotic resistance," J. Antimicrob. Chemother. (2003) 51: 613-617.
Vabret, A., et al., "Development of a PCR-and hybridization-based assay (PCR Adenovirus Consensusâ) for the detection and the species identification of adenoviruses in respiratory specimens", J. Clin. Virol., 2004, vol. 31, No. 2, pp. 116-122.
Van Aerschot et al., "In search of acyclic analogues as universal nucleosides in degenerate probes" *Nucleosides and Nucleotides* (1995) 14:1053-1056.
Van Baar et al., "Characterization of Bacteria by Matrix Assisted Laser Desorption/Ionization and Electrospray Mass Spectrometry" *FEMS Microbiol. Review* (2000) 24:195-219.
Van Camp et al., "Amplification and sequencing of variable regions in bacteria 23S ribosomal Rna genes with conserved primer sequences" *Current Microbiology* (1993) 27:147-151.
Vanchiere et al. "Detection of BK virus and Simian virus 40 in the urine of healthy children" Journal of Medical Virology (2005) 75:447-454.
Van Der Vossen et al., "DNA based typing, identification and detection systems for food spoilage microorganisms: development and implementation" *Int J. Food Microbiol.* (1996) 33:35-49.
Van Der Zee, et al., "Rapid and alternative screening methods for microbiological analysis" J. AOAC Int., 1997, 80, 934-940.
Van Dinten et al., "Proteolytic Processing of the Open Reading Frame 1b-Encoded Part of Arterivirus Replicase Is Mediated by nsp4 Serine Protease and Is Essential for Virus Replication" J. Virology, 1999, vol. 73, pp. 2027-2037.
Van Elden et al., "Simultaneous Detection of Influenza Viruses A and B Using Real-Time Quantitative PCR" J. Clin. Microbiol. (2001) 39(1):196-200.
Van Elden et al., "Clinical diagnosis of influenza virus infection: evaluation of diagnostic tools in general practice" Br. J. Gen. Pract. (2001) 51:630-634.
Van Ert et al., "Mass spectrometry provides accurate characterization of two genetic marker types in Bacillus anthracis" *Biotechniques* (2004) 37:642-644, 646, 648.
Van Leeuwen, W. B. et al., "Rapid Detection of Methicillin-Resistance in *Staphylococus aureus* Isolates by the MRSA-Screen Latex Agglutination Test,"J. Clin. Microbiol. (1999) 37(9):3029-3030.
Van Leeuwen, W. B. et al., "Multilocus Sequence Typing of *Staphylococcus aureus* with DNA Array Technology," J. Clin. Microbiol. (2003) 41(7):3323-3326.
Vanderhallen et al., "Identification of Encephalomyocarditis Virus in Clinical Samples by Reverse Transcription-PCR Followed by Genetic Typing Using Sequence Analysis" *J. Clin. Microbiol.* (1998) 36:3463-3467.
Vannuffel, P. et al.. "Specific Detection of Methicillin-Resistant Staphylococcus Species by Multiplex PCR," J. Clin Microbiol. (1995) 33(11):2864-2867.
Vannuffel, P. et al., "Rapid and Specific Molecular Identification of Methicillin-Resistant *Staphylococcus aureus* in Endotracheal Aspirates from Mechanically Ventilated Patients," J Clin. Microbiol. (1998) 36(8):2366-2368.

Videla, C. et al., "Genomic analysis of adenovirus isolated from Argentinean children with acute lower respiratory infections", J. Clin. Virol., 1999, vol. 14, pp. 67-71.
Vilchez, Regis A et al., "Detection of polyomavirus simian virus 40 tumor antigen DNA in AIDS related systemic non-Hodgkin lymphoma," J. Aids Journal of Acquired Immune Deficiency Syndromes, 29(2):109-116 (Feb. 1, 2002).
Voelter C et al., "Screening human tumor samples with a broad-spectrum polymerase chain reaction method for the detection of polyomaviruses", Virology, Academic Press, Orlando, US 237(2):389-396 (Oct. 1997).
Volokhov et al. Microarray analysis of erythromycin resistance determinants. Journal of Applied Microbiology 95:787-798 (2003).
Von Eiff, C. et al., "Pathogenesis of infections due to coagulase-negative staphylococci," Lancet Infect. Dis. (2002) 2:677-685.
Walker, E. S. et al., "A Decline in Mupimcin Resistance in Methicillin-Resistant *Staphylococcus aureus* Accompanied Administrative Control of Prescriptions," J. Clin. Microbiol. (2004) 42(6):2792-2795.
Wallace, et al., "The Enigma of Endonuclease VII. DNA Repair," 2:441-453 (2003).
Wallet, F. et al., "Choice of a routine method for detecting methicillin-resistance in staphylococci,"I Antimicrob. Chemother. (1996) 37:901-909.
Walters et al., "Genotyping single nucleotide polymorphisms using intact polymerase chain reaction products by electrospray quadrupole mass spectrometry" *Rapid Communications in Mass Spectrometry* (2001) 15:1752-1759.
Wang, G. et al., "Targeted Mutagenesis in Mammalian Cells Mediated by Intracellular Triple Helix Formation," Mol. Cell. Biol. (1995) 15(3):1759-1768.
Ward et al., "Design and performance testing of quantitative real time PCR assays for influenza A and B viral load measurement" *Journal of Clinical Virology* (2004) 29:179-188.
Weissenbacher, M. et al., "Etiologic and Clinical Evaluation of Acute Lower Respiratory Tract Infections in Young Argentinean Children: An Overview", Rev. Infect. Dis., 1990, vol. 12, Suppl. 8; pp. S889-S898.
Welham et al., "The Characterization of Micro-organisms by Matrix-assisted Laser Desorption/Ionization Time-of-flight Mass Spectrometry" *Rapid Communications in Mass Spectrometry* (1998) 12:176-180.
Wertheim, H. F. et al., "Effect of Mupirocin Treatment on Nasal. Pharyngeal, and Perineal Carriage of *Staphylococcus aureus* in Healthy Adults," Antimicrob. Agents Chemother. (2005) 49(4):1465-1467.
Westermann, P. et al., "Inhibition of expression of SV40 virus large T-antigen by antisense oligodeoxyribonucleotides," Biomed. Biochim. Acta (1989) 1:85-93.
Whiley, David M et al., "Simultaneous detection and differentiation of human polyomaviruses JC and BK by a rapid and sensitive PCR-ELAHA assay and a survey of the JCV subtypes within an Australian population," Journal of Medical Virology, 72(3):467-472 (Mar. 2004).
Wichelhaus, T. A. et al., "Rapid Detection of Epidemic Strains of Methicillin-Resistant *Staphylococcus aureus*," J. Clin. Microbiol. (1999) 37(3):690-693.
Wickham, T.J., "Targeting adenovirus", Gene Therapy, 2000, vol. 7, pp. 110-114.
Winger et al., "High resolution accurate mass measurements of biomolecules using a new electrospray ionization ion cyclotron resonance mass spectrometer" J. Am. Soc. Mass Spectrom. 4, 566, 1993.
Wintzingerode et al. "Base-specific fragmentation of amplified 16s rRNA genes analyzed by mass spectrometry: A tool for rapid bacterial identification" PNAS 99(10):7039-7044, 2002.
Wolter et al., "Negative Ion FAB Mass Spectrometric Analysis of Non-Charged Key Intermediates in Oligonucleotide Synthesis: Rapid Identification of Partially Protected Dinucleoside Monophosphates" *Biomed. Environ. Mass Spectrom* . (1987) 14:111-116.
Woo et al., "Identification of Leptospira inadai by continuous monitoring of fluorescence during rapid cycle PCR" *Systematic and Applied Microbiology* (1998) 21:89-96.

Wood, S.R. et al., "Rapid Detection and Serotyping of Adenovirus by Direct Immunofluorescence", J. Med. Virol., 1997, vol. 51, No. 3, pp. 198-201.

Wright et al., "Typing and Subtyping of Influenza Viruses in Clinical Samples by PCR" J. Clin. Microbiol. (1995) 33(5):1180-1184.

Wu et al., "Genetic Organization of the mecA Region in Methicillin-Susceptible and Methicillin-Resistant Strains of *Staphylococcus sciuri*" J. Bacteriol. (1998) 180(2):236-242.

Wu et al., "Establishment of a fluorescent polymerase chain reaction method for the detection of SARS-associated coronavirus and its clinical application" Chin. Med. J. (2003) 116:988-990.

Wunschel et al., "Discrimination Among the *B. cereus* Group, in Comparison to *B. subtilis*, by Structural Carbohydrate Profiles and Ribosomal RNA Spacer Region PCR" *System. Appl. Microbiol.* (1994) 17:625-635.

Wunschel et al., "Analysis of double-stranded polymerase chain reaction products from the *Bacillus cereus* group by electrospray ionization Fourier transform ion cyclotron resonance mass spectrometry" Rapid Communications in Mass Spectrometry (1996) 10:29-35.

Wunschel et al., "Mass spectrometric characterization of DNA for molecular biological applications: Advances using MALDI and ESI" Advances in Mass Spectrometry (1998) 14:Chapter 15/377-Chapter 15/406.

Wunschel et al., "Heterogeneity in *Baciullus cereus* PCR products detected by ESI-FTICR mass spectrometry" Anal. Chem. (1998) 70:1203-1207.

Xu et al., "Intercontinental Circulation of Human Influenza a(H1N2) Reassortant Viruses During the 2001-2002 Influenza Season" J. Infect. Dis. (2002):186:1490-1493.

Xu, W. et al., "Species-Specific Identification of Human Adenoviruses by a Multiplex PCR Assay", J. Clin. Microbiol., 2000, vol. 38, No. 11, pp. 4114-4120.

Xu, W. et al., "Type-Specific Identification of Human Adenovirus, 3, 7, and 21 by a Multiplex PCR Assay", J. Med. Virol., 2001, vol. 64, No. 4, pp. 537-542.

Yao et al., "Mass Spectrometry Based Proteolytic Mapping for Rapid Virus Detection" *Anal. Chem.* (2002) 74:2529-2534.

Yasui et al., "A specific oligonucleotide primer for the rapid detection of Lactobacillus lindneri by polymerase chain reaction" *Can. J. Microbiol.* (1997) 43:157-163.

Ye, K. et al., "Three Distinct Promoters Direct Transcription of Different 5' Untranslated Regions of the Human Interleukin 1 Type I Receptor: A Possible Mechanism for Control of Translation," Cytokine (1996) 8(6):421-429.

Yun, H J et al., "Increased antibacterial activity of OW286, a novel fluoronaphthyridone antibiotic, against *Staphylococcus aureus* strains with defined mutations in DNA gyrase and toposiomerase IV", International Journal of Antimicrobial Agents, Amsterdam, NL, 25(4):334-337 (Apr. 1, 2005).

Zeng et al., "Precision Mapping of Quantitative Trait Loci" *Genetics* (1994) 136:1457-1468.

Zhang et al., "Detection and identification of human influenza viruses by the polymerase chain reaction" J. Virol. Methods (1991) 33(1-2):165-189.

Zhang, K. et al., "New Quadriplex PCR Assay for Detection of Methicillin and Mupirocin Resistance and Simultaneous Discrimination of *Staphylococcus aureus* from Coagulase-Negative Staphylococci," J. Clin. Microbiol. (2004) 42(11):4947-4955.

Zhang, Y.-Q. et al., "Genome-based analysis of virulence genes in a non-biofilm-forming Staphylococcus epidemidis strain (ATCC 12228):" Mol. Microbiol. (2003) 49(6):1577-1593.

Alba M.M., et al., "Vida: A Virus Database System for the Organization of Animal Virus Genome Open Reading Frames," Nucleic Acids Research, 2001, vol. 29 (1), pp. 133-136.

Ausubel F.M., et al., eds., Short Protocols in Molecular Biology: a Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

Benson D.A., et al., "GenBank," Nucleic Acids Research, 1999, vol. 27 (1), pp. 12-17.

Bishop M.J., et al., "Molecular Sequence Databases" in: Nucleic Acid and Protein Sequence Analysis, 4th Chapter, Bishop M.J., et al., eds, IRL Press, 1987, pp. 83-113.

Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.

Butler J.M., et al., High Throughput Genotyping of Forensic STRs and SNPs using Time-of-Flight Mass Spectrometry, 9th International Symposium on Human Identification, 1998, Orlando FL.

Certificate of Correction mailed Jan. 6, 2009 for U.S. Appl. No. 10/660,996, filed Sep. 12, 2003.

Certificate of Correction mailed Aug. 7, 2007 for U.S. Appl. No. 10/660,997, filed Sep. 12, 2003.

Certificate of Correction mailed Dec. 12, 2006 for U.S. Appl. No. 10/156,608, filed May 24, 2002.

Certificate of Correction mailed Jul. 17, 2007 for U.S. Appl. No. 09/891,793, filed Jun. 26, 2001.

Certificate of Correction mailed Mar. 31, 2008 for U.S. Appl. No. 09/891,793, filed Jun. 26, 2001.

Certificate of Correction mailed Mar. 31, 2008 for U.S. Appl. No. 10/156,608, filed May 24, 2002.

Certificate of Correction mailed Mar. 31, 2008 for U.S. Appl. No. 10/660,997, filed Sep. 12, 2003.

Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.

Chiu N.H., et al., "Mass Spectrometry of Single-Stranded Restriction Fragments Captured by an Undigested Complementary Sequence," Nucleic Acids Research, 2000, vol. 28 (8), pp. E31.

Collins D.W., et al., "Numerical Classification of Coding Sequences," Nucleic Acids Research, 1992, vol. 20 (6), pp. 1405-1410.

Co-pending U.S. Appl. No. 10/521,662, 2005.
Co-pending U.S. Appl. No. 10/754,415, 2004.
Co-pending U.S. Appl. No. 10/807,019, 2004.
Co-pending U.S. Appl. No. 10/845,052, 2004.
Co-pending U.S. Appl. No. 10/964,571, 2004.
Co-pending U.S. Appl. No. 11/674,538, 2007.
Co-pending U.S. Appl. No. 11/929,910, 2007.
Co-pending U.S. Appl. No. 11/930,108, 2007.
Co-pending U.S. Appl. No. 11/930,741, 2007.
Co-pending Appl. No. US90/010,447, 2009.
Co-pending Appl. No. US90/010448, 2009.

Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.

Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.

Ecker D.J., et al., "Ibis T5000: a universal biosensor approach for microbiology," Nature Reviews Microbiology, 2008, vol. 6 (7), pp. 553-558.

Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.

Enright M.C., et al., "A multilocus sequence typing scheme for *Streptococcus pneumoniae*: identification of clones associated with serious invasive disease," Microbiology, 1998, vol. 144 (Pt 11), pp. 3049-3060.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.

European Search Report for Application No. EP10175659.1, mailed on Feb. 9, 2011, 4 pages.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Examiner Interview Summary mailed Oct. 3, 2005 for U.S. Appl. No. 10/326,046, filed Dec. 18, 2002.
Examiner Interview Summary mailed Nov. 6, 2008 for U.S. Appl. No. 10/728,486, filed Dec. 5, 2003.
Examiner Interview Summary mailed Feb. 27, 2006 for U.S. Appl. No. 10/326,644, filed Dec. 18, 2002.
Examiner Interview Summary mailed Jan. 27, 2006 for U.S. Appl. No. 10/323,211, filed Dec. 18, 2002.
Examiner Interview Summary mailed May 28, 2008 for U.S. Appl. No. 10/660,998, filed Sep. 12, 2003.
Examiner Interview Summary mailed Oct. 28, 2008 for U.S. Appl. No. 11/331,987, filed Jan. 13, 2006.
Examiner Interview Summary mailed Oct. 29, 2008 for U.S. Appl. No. 11/331,978, filed Jan. 13, 2006.
Examiner Interview Summary mailed Oct. 29, 2009 for U.S. Appl. No. 10/660,122, filed Sep. 11, 2003.
Examiner Interview Summary mailed Jul. 31, 2006 for U.S. Appl. No. 10/326,643, filed Dec. 18, 2002.
Extended European Search Opinion for Application No. EP10175659.1, mailed on Feb. 21, 2011.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Apr. 14, 2011 for U.S. Appl. No. 12/049,949, filed Mar. 17, 2008.
Final Office Action mailed Feb. 18, 2010 for U.S. Appl. No. 10/754,415, filed Jan. 9, 2004.
Final Office Action mailed Jun. 23, 2010 for U.S. Appl. No. 11/930,017, filed Oct. 30, 2007.
Genbank, "Bovine parainfluenza virus 3 strain Shipping Fever, complete genome," Accesion No. AF178655, Sep. 19, 2000.
Genbank, "*Homo sapiens* Haplotype V Mitochondrion, Complete Genome", Accession No. AF381990.1, Dec. 28, 2001.
Genbank, "Human Isolate L34 Mitochondrion D-loop Region", Accession No. U08081.1, Aug. 16, 1994.
GenBank, "il11b08.y1 Human insulinoma *Homo sapiens* cDNA clone Image:6029534 5-similar to SW:COX3_Human P00414 Cytochrome C Oxidase Polypeptide III ;, mRNA sequence", Accession No. BQ581956.1, Jun. 20, 2002.
GenBank, "or72a01.s1 NCI_CGAP_Lu5 *Homo sapiens* cDNA Clone Image:1601352 3-similar to SW:COX1_Human P00395 Cytochrome C Oxidase Polypeptide I ;, mRNA sequence", Accession No. AI002209.1, Jun. 10, 1998.
Genbank, "Virus Nonstructural Polyprotein and Stuctural Polyprotein Genes", Accession No. AF375051.1, Jun. 21, 2001.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.

International Preliminary Report on Patentability and Written Opinion for Application No. PCT/US2005/007404, mailed on Sep. 5, 2006, 7 pages.
International Preliminary Examination Report for Application No. PCT/US2002/06763, mailed on Jun. 11, 2003, 6 pages.
International Preliminary Examination Report for Application No. PCT/US2003/09802, mailed on Apr. 8, 2005, 7 pages.
International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US2005/00386, mailed on Jul. 10, 2006, 6 pages.
International Preliminary Report on Patentability and Written Opinion for Application No. PCT/US2005/030058, mailed on Aug. 20, 2007, 6 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2006/028397, mailed on Mar. 5, 2007, 14 pages.
International Search Report and Written Opinion for Application No. PCT/US2008/057901, mailed on Aug. 28, 2008, 14 pages.
International Search Report for Application No. PCT/US2005/007404, mailed on Feb. 22, 2006, 3 pages.
Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.
Kasai H., et al., "Construction of the gyrB Database for the Identification and Classification of Bacteria," Genome Informatics. Workshop on Genome Informatics, 1998, pp. 13-21.
Kidd-Ljunggren K., et al., "The hepatitis B virus X gene: analysis of functional domain variation and gene phylogeny using multiple sequences," Journal of General Virology, 1995, vol. 76 (pt 9), pp. 2119-2130.
Kikuchi K., et al., "Restriction Fragment Length Polymorphism Analysis of Clinical Isolates of Mycobacterium Haemophilum," Journal of Clinical Microbiology, 1994, vol. 32 (7), pp. 1763-1767.
Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.
Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.
Kowalak J.A., et al., "A Novel Method for the Determination of Post-Transcriptional Modification in RNA by Mass Spectrometry," Nucleic Acids Research, 1993, vol. 21 (19), pp. 4577-4585.
Laken S.J., et al., "Genotyping by Mass Spectrometric Analysis of Short DNA Fragments," Nature Biotechnology, 1998, vol. 16 (13), pp. 1352-1356.
Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.
Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Ni J., et al., "Interpretation of Oligonucleotide Mass Spectra for Determination of Sequence Using Electrospray Ionization and Tandem Mass Spectrometry," Analytical Chemistry, 1996, vol. 68 (13), pp. 1989-1999.

Non-Final Office Action mailed Aug. 4, 2010 for U.S. Appl. No. 12/049,949, filed Mar. 17, 2008.

Non-Final Office Action mailed Apr. 6, 2009 for U.S. Appl. No. 11/331,987, filed Jan. 13, 2006.

Non-Final Office Action mailed Apr. 7, 2006 for U.S. Appl. No. 10/964,571, filed Oct. 12, 2004.

Non-Final Office Action mailed Jun. 10, 2009 for U.S. Appl. No. 10/844,938, filed May 12, 2004.

Non-Final Office Action mailed Jan. 12, 2010 for U.S. Appl. No. 11/491,376, filed Jul. 21, 2006.

Non-Final Office Action mailed Oct. 13, 2010 for U.S. Appl. No. 10/754,415, filed Jan. 9, 2004.

Non-Final Office Action mailed Sep. 16, 2009 for U.S. Appl. No. 11/233,630, filed Sep. 21, 2005.

Non-Final Office Action mailed Feb. 23, 2009 for U.S. Appl. No. 10/660,122, filed Sep. 11, 2003.

Non-Final Office Action mailed May 26, 2010 for U.S. Appl. No. 11/869,449, filed Oct. 9, 2007.

Non-Final Office Action mailed Jul. 27, 2006 for U.S. Appl. No. 11/209,439, filed Aug. 8, 2005.

Non-Final Office Action mailed Jun. 28, 2010 for U.S. Appl. No. 11/930,002, filed Oct. 30, 2007.

Non-Final Office Action mailed Sep. 28, 2009 for U.S. Appl. No. 11/930,017, filed Oct. 30, 2007.

Non-Final Office Action mailed Dec. 29, 2010 for U.S. Appl. No. 12/616,422, filed Nov. 11, 2009.

Non-Final Office Action mailed Apr. 30, 2010 for U.S. Appl. No. 11/930,108, filed Oct. 31, 2007.

Notice of Allowance mailed Apr. 1, 2011 for U.S. Appl. No. 11/233,630, filed Sep. 21, 2005.

Notice of Allowance mailed Jun. 3, 2009 for U.S. Appl. No. 11/331,978, filed Jan. 13, 2006.

Notice of Allowance mailed Aug. 5, 2010 for U.S. Appl. No. 11/233,630, filed Sep. 21, 2005.

Notice of Allowance mailed Aug. 6, 2009 for U.S. Appl. No. 10/728,486, filed Dec. 5, 2003.

Notice of Allowance mailed Dec. 10, 2010 for U.S. Appl. No. 11/233,630, filed Sep. 21, 2005.

Notice of Allowance mailed Dec. 10, 2010 for U.S. Appl. No. 11/491,376, filed Jul. 21, 2006.

Notice of Allowance mailed Nov. 12, 2009 for U.S. Appl. No. 10/728,486, filed Dec. 5, 2003.

Notice of Allowance mailed Dec. 15, 2008 for U.S. Appl. No. 11/331,978, filed Jan. 13, 2006.

Notice of Allowance mailed Sep. 18, 2009 for U.S. Appl. No. 10/660,998, filed Sep. 12, 2003.

Notice of Allowance mailed Nov. 24, 2009 for U.S. Appl. No. 11/331,978, filed Jan. 13, 2006.

Notice of Allowance mailed Oct. 29, 2009 for U.S. Appl. No. 10/660,122, filed Sep. 11, 2003.

Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.

Office Action mailed Feb. 2, 2011 for U.S. Appl. No. 11/869,449, filed Oct. 9, 2007.

Office Action mailed Feb. 3, 2011 for U.S. Appl. No. 12/326,800, filed Dec. 2, 2008.

Office Action mailed Dec. 4, 2006 for Indian Application No. 1136KOLNP2003 filed Mar. 4, 2002.

Office Action mailed May 4, 2010 for U.S. Appl. No. 90/010,447, filed Apr. 9, 2009.

Office Action mailed May 4, 2010 for U.S. Appl. No. 90/010,448, filed Apr. 9, 2009.

Office Action mailed Aug. 5, 2010 for European Application No. 02709785.6 filed Mar. 4, 2002.

Office Action mailed Jan. 6, 2011 for Israel Application No. 157661 filed Mar. 4, 2002.

Office Action mailed Mar. 6, 2009 for U.S. Appl. No. 11/233,630, filed Sep. 21, 2005.

Office Action mailed Apr. 7, 2009 for Canadian Application No. 2525498 filed May 13, 2004.

Office Action mailed Feb. 7, 2008 for European Application No. 03796752.8 filed Dec. 5, 2003.

Office Action mailed Jun. 7, 2010 for European Application No. 06800205.4 filed Jul. 27, 2006.

Office Action mailed Jan. 8, 2007 for U.S. Appl. No. 09/891,793, filed Jun. 26, 2001.

Office Action mailed Sep. 8, 2006 for Chinese Application No. 02809122.1 filed Mar. 4, 2002.

Office Action mailed Dec. 9, 2009 for U.S. Appl. No. 90/010,210, filed Jun. 27, 2008.

Office Action mailed Dec. 9, 2009 for U.S. Appl. No. 90/010,447, filed Apr. 9, 2009.

Office Action mailed Dec. 9, 2009 for U.S. Appl. No. 90/010,448, filed Apr. 9, 2009.

Office Action mailed Feb. 9, 2007 for Chinese Application No. 02809122.1 filed Mar. 4, 2002.

Office Action mailed Jan. 9, 2008 for Japanese Application No. 2002570692 filed Mar. 4, 2002.

Office Action mailed Nov. 9, 2010 for U.S. Appl. No. 11/331,987, filed Jan. 13, 2006.

Office Action mailed Aug. 10, 2004 for U.S. Appl. No. 10/326,642, filed Dec. 18, 2002.

Office Action mailed Dec. 10, 2009 for U.S. Appl. No. 11/929,910, filed Oct. 30, 2007.

Office Action mailed Feb. 10, 2006 for Australian Application No. 2002244250 filed Mar. 4, 2002.

Office Action mailed Jun. 10, 2009 for U.S. Appl. No. 90/010,210, filed Jun. 27, 2008.

Office Action mailed Jun. 10, 2010 for U.S. Appl. No. 90/010,447, filed Apr. 9, 2009.

Office Action mailed Jun. 10, 2010 for U.S. Appl. No. 90/010,448, filed Apr. 9, 2009.

Office Action mailed Aug. 11, 2010 for U.S. Appl. No. 90/010,447, filed Apr. 9, 2009.

Office Action mailed Aug. 11, 2010 for U.S. Appl. No. 90/010,448, filed Apr. 9, 2009.

Office Action mailed Jun. 11, 2010 for U.S. Appl. No. 90/010,210, filed Jun. 27, 2008.

Office Action mailed May 12, 2002 for U.S. Appl. No. 09/798,007, filed Mar. 2, 2001.

Office Action mailed Aug. 13, 2009 for U.S. Appl. No. 11/674,538, filed Feb. 13, 2007.

Office Action mailed Jul. 13, 2010 for U.S. Appl. No. 11/929,930, filed Oct. 30, 2007.

Office Action mailed Mar. 14, 2011 for U.S. Appl. No. 11/930,002, filed Oct. 30, 2007.

Office Action mailed Dec. 15, 2008 for Israel Application No. 157661 filed Mar. 4, 2002.

Office action mailed Dec. 15, 2010 for Canadian Application No. 2508726 filed Dec. 5, 2003.

Office Action mailed Jan. 15, 2008 for Israel Application No. 157661 filed Mar. 4, 2002.

Office Action mailed Mar. 15, 2010 for European Application No. 08730682.5 filed Feb. 25, 2008.

Office Action mailed Apr. 16, 2009 for U.S. Appl. No. 90/010,210, filed Jun. 27, 2008.

Office Action mailed Aug. 16, 2010 for U.S. Appl. No. 11/929,707, filed Oct. 30, 2007.

Office Action mailed Feb. 16, 2011 for U.S. Appl. No. 11/929,910, filed Oct. 30, 2007.

Office Action mailed Mar. 16, 2010 for Canadian Application No. 2616281 filed Jul. 21, 2006.

Office Action mailed Nov. 16, 2009 for Japanese Application No. 2005508488 filed Dec. 5, 2003.

Office Action mailed Nov. 16, 2009 for Japanese Application No. 2005508560 filed Dec. 5, 2003.

Office Action mailed Sep. 17, 2008 for European Application No. 03796752.8 filed Dec. 5, 2003.

Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2008 for Australian Application No. 2003298030 filed Dec. 5, 2003.
Office Action mailed Sep. 18, 2008 for U.S. Appl. No. 10/660,998, filed Sep. 12, 2003.
Office Action mailed Sep. 19, 2006 for U.S. Appl. No. 10/660,122, filed Sep. 11, 2003.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Oct. 21, 2005 for U.S. Appl. No. 10/326,641, filed Dec. 18, 2002.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Oct. 23, 2003 for New Zealand Application No. 527857 filed Mar. 4, 2002.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jul. 24, 2007 for Mexican Application No. PAA2003007927 filed Sep. 2, 2003.
Office Action mailed Jun. 24, 2008 for European Application No. 06800205.4 filed Jul. 27, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Aug. 26, 2010 for Canadian Application No. 2508584 filed Dec. 5, 2003.
Office Action mailed Jul. 27, 2009 for Canadian Application No. 2439655 filed Mar. 4, 2002.
Office Action mailed Jul. 28, 2010 for U.S. Appl. No. 90/010,210, filed Jun. 27, 2008.
Office Action mailed Mar. 29, 2010 for Australian Application No. 2006272776 filed Jul. 21, 2006.
Office Action mailed Oct. 29, 2009 for U.S. Appl. No. 90/010,448, filed Apr. 9, 2009.
Office Action mailed Jul. 30, 2009 for Japanese Application No. 2002570692 filed Mar. 4, 2002.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2007 for Philippines Application No. PH12003500824 filed Mar. 4, 2002.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Partial European Search Report for Application No. EP01106974, mailed on Dec. 16, 2002, 2 pages.
Roberts M.S., et al., "Recombination and Migration Rates in Natural Populations of *Bacillus subtilis* and *Bacillus mojavensis*," Evolution, 1995, vol. 49 (6), pp. 1081-1094.
Ross P., et al., "High Level Multiplex Genotyping by MALDI-TOF Mass Spectrometry," Nature Biotechnology, 1998, vol. 16 (13), pp. 1347-1351.
Supplementary European Search Report for Application No. EP03814656, mailed on Oct. 16, 2007, 2 pages.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
U.S. Appl. No. 60/369,405, 2002.
U.S. Appl. No. 60/397,365, 2002.
U.S. Appl. No. 60/431,319, 2002.
U.S. Appl. No. 60/443,443, 2003.
U.S. Appl. No. 60/443,788, 2003.
U.S. Appl. No. 60/447,529, 2003.
U.S. Appl. No. 60/453,607, 2003.
U.S. Appl. No. 60/461,494, 2003.
U.S. Appl. No. 60/470,175, 2003.
U.S. Appl. No. 60/501,926, 2003.
U.S. Appl. No. 60/509,911, 2003.
U.S. Appl. No. 60/615,387, 2004.
U.S. Appl. No. 60/701,404, 2005.
U.S. Appl. No. 60/705,631, 2005.
U.S. Appl. No. 60/720,843, 2005.
U.S. Appl. No. 60/747,607, 2006.
U.S. Appl. No. 60/771,101, 2006.
U.S. Appl. No. 60/773,124, 2006.
U.S. Appl. No. 60/891,479, 2007.
U.S. Appl. No. 60/941,641, 2007.
Verma S., et al., "Modified Oligonucleotides: Synthesis and Strategy for Users," Annual Review of Biochemistry, 1998, pp. 99-134.
Watanabe K., et al., "ICB Database: the gyrB Database for Identification and Classification of Bacteria," Nucleic Acids Research, 2001, vol. 29 (1), pp. 344-345.
Written Opinion for Application No. PCT/US2004/33742, mailed on May 15, 2006, 5 pages.
Zhang J., et al., "PowerBLAST: A New Network BLAST Application for Interactive or Automated Sequence Analysis and Annotation," Genome Research, 1997, vol. 7 (6), pp. 649-656.
Notice of Allowance mailed May 25, 2011 for U.S. Appl. No. 11/929,707, filed Oct. 30, 2007.

\* cited by examiner

Figure 3

SEQUENCE LISTING

<160> NUMBER OF SEQ ID NOS: 93

<210> SEQ ID NO 1
<211> LENGTH: 11444

<212> TYPE: DNA
<213> ORGANISM: Venezuelan equine encephalitis virus

<400> SEQUENCE: 1

```
atgggcggcg caagagagaa gcccaaacca attacctacc caaaatggag aaagttcacg      60
ttgacatcga ggaagacagc ccattcctca gagctttaca acggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc ataagtatca ttgcatctgt ccgatgagat     300
gtgcggaaga tccggacaga ttgtacaagt atgcaactaa gctgaagaaa aattgcaagg     360
aaataactga caaggaattg gacaagaaaa tgaaggagct cgccgccgtc atgagcgacc     420
ctgacctgga aactgagact atgtgcctcc acgacgatga gtcatgtcgc tacgaggggc     480
aagtcgctgt ttaccaggat gtatacgcag ttgacggacc gacaagtctc tatcaccaag     540
ccaacaaggg agttagagtc gcctactgga taggctttga caccacccct tttatgttta     600
agaacttggc tggagcatat ccatcatact ctaccaactg gccgacgaa accgtgttaa      660
cggctcgtaa cataggccta tgcagctccg acgtcatgga gcggtcacgt agagggatgt     720
ccattcttag gaagaagtat ttgaaaccat ccaataatgt cctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc tgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgca    1140
tagtcgtcaa cggtcgcacc caaagaaaca ccaataccat gaagaattat cttttgcccg    1200
tagtggccca ggcatttgct aggtgggcaa aggaatataa ggaagatcaa gaagatgaga    1260
ggccactagg actacgagat agacagttag tcatggggtg ctgctgggct tttagaaggc    1320
acaagataac atctatttat aagcgcccag atacccaaac catcatcaaa gtgaacagcg    1380
atttccactc attcgtgctg cccaggatag gcagtaacac actggagatc gggctgagaa    1440
cgagaatcag gaaaatgcta gaagagcaca aggagccgtc acctctcatt actgccgagg    1500
acatacaaga ggctaagtgc gcagccgatg aggctaagga agtgcgtgaa gccgaggagc    1560
tgcgcgctgc tctaccacct ttggcagctg attttgagga gcccactctg gaagccgatg    1620
tcgacttgat gttacaagag gctggggccg gctcagtgga gacacctgt ggcttgataa     1680
aggttaccag ctatgccggc gaggacaaga tcggctctta cgcagtgctt tctccacagg    1740
ctgtactcaa gagtgagaaa ctatcttgca ttcaccctct cgctgaacaa gtcatagtga    1800
taacacactc tggccgaaaa gggcgttatg ccgtggaacc ctaccatgga aaagtagtgg    1860
tgccagaggg acatgcaata cccgtccagg actttcaagc tctgagtgaa agtgccacca    1920
tcgtgtacaa cgaacgagag ttcgtaaaca ggtacctgca ccatattgcc acacatggag    1980
gagcgctgaa cacagatgaa gaatattaca aaactgtcaa gcccagcgag cacgacggcg    2040
aatacctgta cgacatcgac aggaaacaat gcgtcaagaa agaattagtc actgggctag    2100
ggcttacagg cgagctggtg gatcctccct tccatgaatt tgcctacgag agtctgagaa    2160
cacgtccggc cgctccttac caagtaccaa ccatagggt gtatgcgtg ccggggtcag     2220
gcaagtctgg catcattaaa agcgcagtca ccaaaaaaga tctggtggtg agcgccaaga    2280
```

```
aagaaaactg cgcagaaata ataagggacg tcaagaaaat gaaagggctg gacgtcaatg    2340
ccagaactgt ggactcagtg ctcttgaatg gatgcaaaca ccccgtagag accctgtata    2400
ttgacgaagc ttttgcttgt catgcaggca ctctcagagc gctcatagcc atcataagac    2460
ctaaaaaggc agtgctctgc ggggatccaa aacagtgtgg cttttttcaat atgatgtgcc    2520 tgaaagtgca ttttaaccac gagatttgca cgcaggtctt ccacaaaagc atctctcgcc    2580
gttgcactaa atccgtgact tcggtcgtct caaccttgtt ttacgacaaa aggatgagaa    2640
cgacgaaccc gaaagagact aagattgtga ttgacactac tggcagtacc aaaccgaagc    2700
aggacgatct cattctcact tgtttcagag ggtgggtgaa gcagttgcaa atagattaca    2760
aaggcaacga aataatgacg gcagctgcct ctcaagggct gacccgtaaa ggcgtgtatg    2820
ccgttcggta caaggtgaat gaaaatcccc tgtacgcacc cacctcagaa catgtgaacg    2880
tcctactgac ccgcacggag gaccgtatcg tgtggaaaac actagccggt gatccatgga    2940
taaaaatact gacggccaag tatcctggga acttcactgc cacgatagag gaatggcaag    3000
cagagcatga tgccatcatg aggcacatct tggagagacc ggaccctacc gacgttttcc    3060
aaaataaggc gaacgtgtgt tgggccaagg cttttggtgc ggtactgaag actgcaggca    3120
tagacatgac cactgaacaa tggaacactg tggattactt cgaaacggac aaagctcact    3180
cagcagagat agtattgaac caactatgcg tgaggttctt tggactcgac ctggactccg    3240
gtctattttc tgcacccact gttccgttat ccattaggaa taatcactgg gataattccc    3300
cgtcgcctaa catgtacggg ttgaataaag aagtggtccg ccagctctcc cgcaggtacc    3360
cacaactgcc tcgagcagtt gccaccggaa gagtctatga catgaacact ggcacgctgc    3420
gcaattatga tccgcgcata aatcagtac ctgtgaacag aagactgcct catgctttag    3480
tcctccacca taatgaacac ccacagagtg acttttcttc attcgtcagc aaactgaagg    3540
gcagaactgt cttggtggtc ggggagaagt tgtccgtccc aggcaaaaag gtcgactggt    3600
tgtcagacca gcctgaggct acctttagag ctcggctgga tttaggtatc ccaggtgacg    3660
tgcccaaata cgacattgta tttattaacg tgaggactcc atataaatac catcattatc    3720
agcagtgtga agaccacgcc attaagctta gtatgttgac caagaaagct tgtctgcatt    3780
tgaatcccgg cggaacctgc gtcagcatag gttatggtta cgctgacagg gccagcgaga    3840
gcatcattgg tgctatagcg cggcagttca agttctcccg ggtatgcaaa ccgaaatcct    3900
cacatgaaga gacagaagta ctgtttgtat tcattgggta cgatcgcaag gcccgtacgc    3960
acaatcctta caagctttca tctaccttga ccaacatcta tacaggttcc agactccacg    4020
aagccggatg cgcaccctca tatcatgtgg tgcgagggga tattgccacg gccaccgaag    4080
gagtgatcat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaagttga aggggacaaa cagttggcag aggcttatga gtccatcgct aaaattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatcagacga ctcttcggtg acagaaccgg    4560
atgcagagct ggtgagggta catccgaaga gttctttggc tggaaggaag gctacagca    4620 caagtgatgg caagactttc tcatatttgg aagggaccaa atttcaccag gcggccaagg    4680
```

```
atatagcaga aattaatgcc atgtggccag ttgcaacgga ggccaatgag caagtatgca    4740
tgtatatcct cggtgaaagc atgagcagca ttaggtcgaa atgccccgtc gaggagtcgg    4800
aagcctccac accacctagc acgctgcctt gcttgtgcat ccatgctatg actccagaaa    4860
gagtacaacg cctaaaagcc tcacgtccag aacaaattac tgtgtgctca tcctttccat    4920
tgccgaagta tagaatcact ggtgtgcaga agatccagtg ctcccagcct atactgttct    4980
caccgaaggt gcctgcgtac attcatccac ggaagtacct cgtggaaaca ccaccggtag    5040
aagagactcc ggagtcgccg gcagagaacc aatccacaga ggggacacct gaacaaccag    5100
cacttgtaaa cgtggatgca accaggacta gaatgcctga accgatcatc attgaagagg    5160
aagaagagga tagtataagt ttgctgtcag acggcccgac ccaccaggtg ctgcaagtcg    5220
aggcagacat tcacgggtcg ccttctgtat ccagctcatc ctggtccatt cctcatgcat    5280
ccgactttga tgtggacagc ttatccatcc ttgacaccct ggatggagct agcgtgacca    5340
gcggggcagt gtcagccgag actaactcct acttcgcaag gagcatggag tttcgggcgc    5400
gaccggtgcc tgcgcctcga accgtattca ggaaccctcc acatcccgca ccgcgcacaa    5460
gaacaccgcc acttgcacac agcagggcca gctcgagaac tagcctagtt ccaccccgc    5520 caggcgtgaa tagggtgatt actagagagg agctcgaggc gcttaccccg tcccgcgctc    5580
ctagcaggtc ggcctcaaga actagcctgg tctctaaccc gccaggcgta aatagggtga    5640
ttacaagaga ggagtttgag gcgttcgtag cacaacaaca atgacggttt gacgcgggtg    5700
catacatctt ttcctccgat accggtcaag gcatttaca acaaaaatca gtaaggcaaa    5760
cggtgttatc cgaagtggtg ttggagagga ccgaattgga gatttcgtat gccccgcgcc    5820
tcgaccagga aaaagaagaa ctactacgca agaaattaca gctgaatccc acacctgcta    5880
acagaagcag ataccagtcc aggagggtgg agaatatgaa agccataaca gctagacgta    5940
ttctgcaagg cctagggcat tatttgaagg cagaaggaaa agtggagtgc atcgaaccc    6000 tgcatcctgt tcctttgtat tcatctagtg tgaatcgtgc ttttttcaagc cccaaggtcg    6060 cagtggaagc ctgcaatgcc atgctgaaag aaaattttcc gactgtagct tcctactgta    6120
ttattccaga gtacgatgcc tatctggaca tggttgacgg cgcttcttgt tgcttagaca    6180
ctgccagttt ttgccctgcg aagctgcgca gctttccaaa gaaacactcc tatttggaac    6240
ccacaatacg gtcggcagtg ccatcagcga ttcagaacac gctccagaac gtcctggcag    6300
ctgccacaaa aagaaattgc aacgtcacgc aaatgagaga attgcccgta ttggattcgg    6360
ctgcctttaa tgtggaatgc ttcaagaaat atgcgtgcaa taatgaatat tgggaaacgt    6420
ttaaagaaaa ccccatcagg cttactgaag aaaatgtggt aaattacatt actaaattaa    6480
aaggaccaaa agctgctgct ctttttgcga agacacataa tttgaatatg ttacaggaca    6540
taccaatgga caggtttgta atggacttaa agagggacgt gaaagtgact ccaggaacaa    6600
aacatactga agaacggccc aaggtacagg tgattcaggc tgccgatcca ctagcgacag    6660
cggatctgtg cggaatccac cgggagttgg ttaggagatt aaatgctgtc ctgcttccga    6720
acatccatac actgtttgac atgtcggctg aagactttga cgctattatt gccgagcatt    6780
tccagcctgg ggactgtgta ctggaaactg acattgcgtc gtttgataaa agtgaggacg    6840
acgccatggc tctgaccgcg ttaatgattc tggaagacct aggagtggac gcagagctgt    6900
tgacgctgat tgaggcggct ttcggcgaaa tatcatcaat acatttgccc accaaaacta    6960
aatttaaatt cggagccatg atgaaatccg gaatgttcct cacactgttt gtgaacacag    7020
tcatcaacat cgtaatcgca agcagagtgt taagagagcg gctaaccgga tcaccatgtg    7080
```

```
cagcattcat tggagatgac aatatcgtga aaggagtcaa atctgacaaa ttaatggcag    7140
acaggtgcgc cacttggttg aacatggaag tcaagatcat agacgccgtg gtgggcgaga    7200
aagcgcccta tttttgtgga gggtttatct tgtgtgactc cgtgaccggc acagcgtgcc    7260
gtgtggcaga ccccctaaaa aggctgttta agcttggcaa acccctggca gtagacgatg    7320
aacatgacga tgacaggaga agggcattac acgaagagtc aacacgctgg aatcgagtgg    7380
gaattcttcc agagctgtgt aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gatgttcccg ttccaaccaa tgtatccgat gcagccaatg ccctatcgta acccgttcgc    7620
ggccccgcgc aggccctggt tcccagaac cgacccttt ctggcgatgc aggtgcagga    7680
attaacccgc tcgatggcta acctgacgtt caagcaacgc cgggacgcgc cacctgaggg    7740
gccacctgct aagaaaccta agaggaggc cccgcaaaag caaaaggggg aggccaagg    7800 gaagaagaag aagaaccagg ggaagaagaa ggccaagacg gggccgccta atccgaaggc    7860
acagagtgga aacaagaaga agcccaacaa gaaaccaggc aagagacagc gcatggtcat    7920
gaaattggaa tctgacaaga cattcccaat tatgctggaa gggaagatta acggctacgc    7980
ttgcgtggtc ggagggaagt tattcaggcc gatgcacgtg gaaggcaaga tcgacaacga    8040
cgttctggcc gcacttaaga cgaagaaagc atccaaatat gatcttgagt atgcagatgt    8100
gccacagaac atgcgggccg atacattcaa gtacacccat gagaagcccc aaggctatta    8160
cagctggcat catggagcag tccaatatga aaatgggcgt ttcacggtgc aaaaggagt    8220 tggggccaag ggagacagcg gaagacccat tctggataat cagggacggg tggtcgctat    8280
tgtgctggga ggtgtgaatg aaggatctag gacagccctt tcagtcgtca tgtggaacga    8340
gaagggagta actgtgaagt atactccgga gaactgcgag caatggtcac tagtgaccac    8400
tatgtgcctg ctcgccaatg tgacgttccc atgtgccgaa ccaccaattt gctacgacag    8460
aaaaccagca gagactttgg ccatgctcag cgttaacgtt gacaacccgg gctacgatga    8520
gctgctggaa gcagctgtta agtgccccgg aagaaaaagg agatctaccg aggagctgtt    8580
taaggagtat aagctaacgc gcccttacat ggcagatgc atcagatgtg ccgttgggag    8640
ctgccatagt ccaatagcaa ttgaggcagt gaagagcgac gggcacgacg gctatgttag    8700
acttcagact cctcgcagt atggcctgga ttcctctggc aacttaaagg gaaggactat    8760
gcggtatgat atgcacggga ccattgaaga gataccacta catcaagtgt cactccacac    8820
atctcgcccg tgtcacattg tggatgggca tggttatttt ctgcttgcta ggtgcccggc    8880
aggggactcc atcaccatgg aatttaagaa aggttcagtc acacactcct gctcagtgcc    8940
gtatgaagtg aaatttaatc ctgtaggcag agaactctac actcatccac cagaacacgg    9000
agcagagcaa gcgtgccaag tctacgcgca cgatgcacag aacagaggag cttatgtcga    9060
gatgcacctc ccgggctcag aagtggacag cagtttgatt tccttgagcg gcagttcagt    9120
caccgtgaca cctcctgtcg ggactagcgc cttggtgaaa tgcaagtgcg gcggcacaaa    9180
gatctccgaa accatcaaca ggcaaaaca gttcagccag tgcacaaaga aggagcagtg    9240
cagagcatat cgactgcaga atgacaagtg ggtgtataat tctgacaaac tgcccaaagc    9300
agcgggagcc acccctaaaag gaaaactaca cgtcccgttc ttgctggcag acggcaaatg    9360
caccgtgcct ctagcaccgg aacctatgat aaccttcggt ttccgatcag tgtcactgaa    9420
actgcaccct aagaatccca catatctgac cactcgccaa cttgctgatg agcctcatta    9480
```

-continued

```
cacgcacgag ctcatatctg aaccagctgt taggaattt accgtcactg aaaaggggtg    9540
ggagtttgta tggggaaacc atccgccgaa aaggttttgg gcacaggaaa cagcacccgg    9600
aaatccacat gggctgccac atgaggtgat aactcattat taccacagat accctatgtc   9660
caccatcctg ggtttgtcaa tttgcgccgc cattgtaacc gtttccgttg cagcgtccac   9720
ctggctgttt tgcaaatcca gagtttcgtg cctaactcct taccggctaa cacctaacgc   9780
caggatgccg ctttgcctgg ccgtgctttg ctgcgcccgc actgcccggg ccgagaccac   9840
ctgggagtcc ttggatcacc tatggaacaa taaccaacag atgttctgga ttcaattgct   9900
gatccctctg gccgccttga ttgtagtgac tcgcctgctc aagtgcgtgt gctgtgtagt   9960
gcctttttta gtcgtggccg cgccgcagg cgccggcgcc tacgagcacg cgaccacgat   10020
gccgagccaa gcgggaatct cgtataacac catagtcaac agagcaggct acgcgccact   10080
ccctatcagc ataacaccaa caaagatcaa gctgataccc acagtgaact tggagtacgt   10140
cacctgccac tacaaaacag gaatggattc accagccatc aaatgctgcg gatctcagga   10200
atgtactcca actaacaggc ctgatgaaca gtgcaaagtc ttcacagggg tttacccgtt   10260
catgtgggga ggtgcatatt gcttttgcga cactgagaat actcaggtca gcaaggccta   10320
cgtaatgaaa tctgacgact gccttgcgga tcatgctgaa gcatacaaag cgcacacagc   10380
ctcagtgcag gcgttcctca acatcacagt ggggaacac tctattgtga ccaccgtgta   10440
tgtgaatgga gaaactcctg tgaacttcaa tgggtcaaa ctaactgcag gtccactttc   10500
cacagcttgg acacccttg acagaaaat cgtgcagtat gccggggaga tctataatta   10560 cgatttcct gagtatgggg caggacaacc aggagcattt ggagacatac aatccagaac   10620
agtctcaagc tcagatctgt atgccaatac caacctagtg ctgcagagac caaaagcagg   10680
agcgatccat gtgccataca ctcaggcacc atcgggtttt gagcaatgga agaaagataa   10740
agctccgtca ttgaaattca ccgccccttt cggatgcgaa atatatacaa accccattcg   10800
cgccgaaaat tgtgctgtag ggtcaattcc attagccttt gacattcccg acgccttgtt   10860
caccagggtg tcagaaacac cgacactttc agcggccgaa tgcactctta acgagtgcgt   10920
gtattcatcc gactttggcg ggatcgccac ggtcaagtat tcggccagca agtcaggcaa   10980
gtgcgcagtc catgtgccat cagggactgc taccctaaaa gaagcagcag tcgagctaac   11040
cgagcaaggg tcggcgacca ttcatttctc gaccgcaaat atccaccgg agttcaggct   11100 ccaaatatgc acatcatatg tcacgtgcaa aggtgattgt caccccccga agaccacat   11160 tgtgacacac ccccagtatc acgcccaaac atttacagcc gcggtgtcaa aaaccgcgtg   11220
gacgtggtta acatccctgc tgggaggatc ggccgtaatt attataattg gcttagtgct   11280
ggctactatt gtggccatgt acgtgctgac caaccagaaa cataattgaa catagcagca   11340
attggcaagc tgcttatata gaacttgcgg cgattggcat gccgctttaa aattttattt   11400
tattttcttt tcttttccga atcggatttt gttttaata tttc                      11444
```

<210> SEQ ID NO 2
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (11)..(11)
<223> OTHER INFORMATION: 5-propynylcytosine
<220> FEATURE:
<221> NAME/KEY: modified_base

```
<222> LOCATION: (13)..(14)
<223> OTHER INFORMATION: 5-propynyluracil
<220> FEATURE:
<221> NAME/KEY: modified_base
<222> LOCATION: (16)..(16)
<223> OTHER INFORMATION: 5-propynyluracil
<220> FEATURE:
<221> NAME/KEY: modified_base
<222> LOCATION: (17)..(17)
<223> OTHER INFORMATION: 5-propynylcytosine

<400> SEQUENCE: 2
aatgctagag cguutucgca                                            20

<210> SEQ ID NO 3
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (11)..(11)
<223> OTHER INFORMATION: 5-propynylcytosine
<220> FEATURE:
<221> NAME/KEY: modified_base
<222> LOCATION: (13)..(14)
<223> OTHER INFORMATION: 5-propynyluracil
<220> FEATURE:
<221> NAME/KEY: modified_base
<222> LOCATION: (16)..(16)
<223> OTHER INFORMATION: 5-propynyluracil
<220> FEATURE:
<221> NAME/KEY: modified_base
<222> LOCATION: (17)..(17)
<223> OTHER INFORMATION: 5-propynylcytosine

<400> SEQUENCE: 3
aatgctagag cguutucgca                                            20

<210> SEQ ID NO 4
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (8)..(8)
<223> OTHER INFORMATION: 5-propynylcytosine
<220> FEATURE:
<221> NAME/KEY: modified_base
<222> LOCATION: (10)..(11)
<223> OTHER INFORMATION: 5-propynyluracil
<220> FEATURE:
<221> NAME/KEY: modified_base
<222> LOCATION: (13)..(13)
<223> OTHER INFORMATION: 5-propynyluracil
<220> FEATURE:
<221> NAME/KEY: modified_base
<222> LOCATION: (14)..(14)
<223> OTHER INFORMATION: 5-propynylcytosine

<400> SEQUENCE: 4
gctagagcgu utucgca                                               17

<210> SEQ ID NO 5
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: modified_base
```

<222> LOCATION: (3)..(3)
<223> OTHER INFORMATION: 5-propynylcytosine
<220> FEATURE:
<221> NAME/KEY: modified_base
<222> LOCATION: (10)..(10)
<223> OTHER INFORMATION: 5-propynyluracil

<400> SEQUENCE: 5
tgcgaagggu acgtcgt                                                   17

<210> SEQ ID NO 6
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (3)..(3)
<223> OTHER INFORMATION: 5-propynyluracil
<220> FEATURE:
<221> NAME/KEY: modified_base
<222> LOCATION: (8)..(9)
<223> OTHER INFORMATION: 5-propynylcytosine
<220> FEATURE:
<221> NAME/KEY: modified_base
<222> LOCATION: (13)..(13)
<223> OTHER INFORMATION: 5-propynyluracil

<400> SEQUENCE: 6
tgugtgacca gaugac                                                    16

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aatgctagag cgttttcgca                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aatgctagag cgttttcgca                                                20

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
gctagagcgt tttcgca                                                   17

<210> SEQ ID NO 10
<211> LENGTH: 14
<212> TYPE: DNA
<213> ORGANISM: Artificial Sequence
<220> FEATURE:
<223> OTHER INFORMATION: Primer

<400> SEQUENCE: 10

```
tgcgaagggt acgt                                                        14
```

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11

```
tgcgaagggt acgtcgt                                                     17
```

<210> SEQ ID NO 12
<211> LENGTH: 16
<212> TYPE: DNA
<213> ORGANISM: Artificial Sequence
<220> FEATURE:
<223> OTHER INFORMATION: Primer

<400> SEQUENCE: 12

```
tgtgtgacca gatgac                                                      16
```

<210> SEQ ID NO 13
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (12)..(12)
<223> OTHER INFORMATION: 5-propynylcytosine
<220> FEATURE:
<221> NAME/KEY: modified_base
<222> LOCATION: (14)..(15)
<223> OTHER INFORMATION: 5-propynyluracil
<220> FEATURE:
<221> NAME/KEY: modified_base
<222> LOCATION: (17)..(17)
<223> OTHER INFORMATION: 5-propynyluracil
<220> FEATURE:
<221> NAME/KEY: modified_base
<222> LOCATION: (18)..(18)
<223> OTHER INFORMATION: 5-propynylcytosine

<400> SEQUENCE: 13

```
taatgctaga gcguutucgc a                                                21
```

<210> SEQ ID NO 14
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (12)..(12)
<223> OTHER INFORMATION: 5-propynylcytosine
<220> FEATURE:
<221> NAME/KEY: modified_base
<222> LOCATION: (14)..(15)
<223> OTHER INFORMATION: 5-propynyluracil
<220> FEATURE:
<221> NAME/KEY: modified_base
<222> LOCATION: (17)..(17)
<223> OTHER INFORMATION: 5-propynyluracil
<220> FEATURE:
<221> NAME/KEY: modified_base
<222> LOCATION: (18)..(18)
<223> OTHER INFORMATION: 5-propynylcytosine

<400> SEQUENCE: 14

```
taatgctaga gcguutcgc a                                              21
```

<210> SEQ ID NO 15
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (12)..(12)
<223> OTHER INFORMATION: 5-propynylcytosine
<220> FEATURE:
<221> NAME/KEY: modified_base
<222> LOCATION: (14)..(15)
<223> OTHER INFORMATION: 5-propynyluracil
<220> FEATURE:
<221> NAME/KEY: modified_base
<222> LOCATION: (17)..(17)
<223> OTHER INFORMATION: 5-propynyluracil
<220> FEATURE:
<221> NAME/KEY: modified_base
<222> LOCATION: (18)..(18)
<223> OTHER INFORMATION: 5-propynylcytosine

<400> SEQUENCE: 15

```
taatgctaga gcguutcgc a                                              21
```

<210> SEQ ID NO 16
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (9)..(9)
<223> OTHER INFORMATION: 5-propynylcytosine
<220> FEATURE:
<221> NAME/KEY: modified_base
<222> LOCATION: (11)..(12)
<223> OTHER INFORMATION: 5-propynyluracil
<220> FEATURE:
<221> NAME/KEY: modified_base
<222> LOCATION: (14)..(14)
<223> OTHER INFORMATION: 5-propynyluracil
<220> FEATURE:
<221> NAME/KEY: modified_base
<222> LOCATION: (15)..(15)
<223> OTHER INFORMATION: 5-propynylcytosine

<400> SEQUENCE: 16

```
tgctagagcg uutucgca                                                 18
```

<210> SEQ ID NO 17
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (4)..(4)
<223> OTHER INFORMATION: 5-propynylcytosine
<220> FEATURE:
<221> NAME/KEY: modified_base
<222> LOCATION: (11)..(11)
<223> OTHER INFORMATION: 5-propynyluracil

<400> SEQUENCE: 17

```
ttgcgaaggg uacgt                                                    15
```

```
<210> SEQ ID NO 18
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (4)..(4)
<223> OTHER INFORMATION: 5-propynylcytosine
<220> FEATURE:
<221> NAME/KEY: modified_base
<222> LOCATION: (11)..(11)
<223> OTHER INFORMATION: 5-propynyluracil

<400> SEQUENCE: 18
ttgcgaaggg uacgtcgt                                                 18

<210> SEQ ID NO 19
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (4)..(4)
<223> OTHER INFORMATION: 5-propynylcytosine
<220> FEATURE:
<221> NAME/KEY: modified_base
<222> LOCATION: (11)..(11)
<223> OTHER INFORMATION: 5-propynyluracil

<400> SEQUENCE: 19
ttgcgaaggg uacgtcgt                                                 18

<210> SEQ ID NO 20
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (4)..(4)
<223> OTHER INFORMATION: 5-propynyluracil
<220> FEATURE:
<221> NAME/KEY: modified_base
<222> LOCATION: (9)..(10)
<223> OTHER INFORMATION: 5-propynylcytosine
<220> FEATURE:
<221> NAME/KEY: modified_base
<222> LOCATION: (14)..(14)
<223> OTHER INFORMATION: 5-propynyluracil

<400> SEQUENCE: 20
ttgugtgacc agaugac                                                  17

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
tccatgctaa tgctagagcg ttttcgca                                      28

<210> SEQ ID NO 22
<211> LENGTH: 24
<212> TYPE: DNA
<213> ORGANISM: Artificial Sequence
```

```
<220> FEATURE:
<223> OTHER INFORMATION: Primer

<400> SEQUENCE: 22
tgtcagttgc gaagggtacg tcgt                                          24

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
taatgctaga gcgttttcgc a                                             21

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
ttgcgaaggg tacgtcgt                                                 18

<210> SEQ ID NO 25
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine

<400> SEQUENCE: 25
uccaatgcta gagcgttttc gca                                           23

<210> SEQ ID NO 26
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine

<400> SEQUENCE: 26
ucctgcgaag ggtacgtcgt                                               20

<210> SEQ ID NO 27
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: modified_base
```

```
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
<222> LOCATION: (4)..(4)
<223> OTHER INFORMATION: 5-propynyluracil

<400> SEQUENCE: 27
uccuaatgct agagcgtttt cgca                                          24

<210> SEQ ID NO 28
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
<222> LOCATION: (4)..(4)
<223> OTHER INFORMATION: 5-propynyluracil

<400> SEQUENCE: 28
uccutgcgaa gggtacgtcg t                                             21

<210> SEQ ID NO 29
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
<222> LOCATION: (4)..(5)
<223> OTHER INFORMATION: 5-propynyluracil

<400> SEQUENCE: 29
uccuuaatgc tagagcgttt tcgca                                         25

<210> SEQ ID NO 30
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
```

```
<222> LOCATION: (4)..(5)
<223> OTHER INFORMATION: 5-propynyluracil

<400> SEQUENCE: 30
uccuutgcga agggtacgtc gt                                      22

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
tccttcaatg ctagagcgtt ttcgca                                  26

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tccttctgcg aagggtacgt cgt                                     23

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
tgccagctac actgtgcgac cagatgac                                28

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
tattgtcagt tgcgaagggt acgt                                    24

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
tattgtcagt tgcgacgggt acgt                                    24

<210> SEQ ID NO 36
<211> LENGTH: 26
<212> TYPE: DNA
<213> ORGANISM: Artificial Sequence
<220> FEATURE:
<223> OTHER INFORMATION: Primer

<400> SEQUENCE: 36
tctatagtca gttgcgacgg gtacgt                                  26
```

```
<210> SEQ ID NO 37
<211> LENGTH: 31
<212> TYPE: DNA
<213> ORGANISM: Artificial Sequence
<220> FEATURE:
<223> OTHER INFORMATION: Primer

<400> SEQUENCE: 37
tgtcagctac attgtgtgac caaatgactg g                             31

<210> SEQ ID NO 38
<211> LENGTH: 31
<212> TYPE: DNA
<213> ORGANISM: Artificial Sequence
<220> FEATURE:
<223> OTHER INFORMATION: Primer

<400> SEQUENCE: 38
taccagccac actttgcgat cagatgacag g                             31

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
tccatgctaa cgccagagcg ttttcgca                                 28

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
tccatgctaa cgccagagcg ttttcgca                                 28

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
tgacgtagac ccccagagtc cgttt                                    25

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
tggcgctatg atgaaatctg gaatgtt                                  27

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43
```
tggcgctatg atgaaatctg gaatgtt                                        27

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
tgccttcatc ggcgatgaca acat                                           24

<210> SEQ ID NO 45
<211> LENGTH: 31
<212> TYPE: DNA
<213> ORGANISM: Artificial Sequence
<220> FEATURE:
<223> OTHER INFORMATION: Primer

<400> SEQUENCE: 45
tgtcggccga ggattttgat gctatcatag c                                   31

<210> SEQ ID NO 46
<211> LENGTH: 27
<212> TYPE: DNA
<213> ORGANISM: Artificial Sequence
<220> FEATURE:
<223> OTHER INFORMATION: Primer

<400> SEQUENCE: 46
tgcggtaccg tcaccatttc agaacac                                        27

<210> SEQ ID NO 47
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (7)..(8)
<223> OTHER INFORMATION: 5-propynylcytosine
<220> FEATURE:
<221> NAME/KEY: modified_base
<222> LOCATION: (11)..(11)
<223> OTHER INFORMATION: 5-propynyluracil
<220> FEATURE:
<221> NAME/KEY: modified_base
<222> LOCATION: (13)..(13)
<223> OTHER INFORMATION: 5-propynyluracil
<220> FEATURE:
<221> NAME/KEY: modified_base
<222> LOCATION: (14)..(14)
<223> OTHER INFORMATION: 5-propynylcytosine

<400> SEQUENCE: 47
gcacttccaa uguccaggat                                                20

<210> SEQ ID NO 48
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (7)..(8)
<223> OTHER INFORMATION: 5-propynylcytosine
<220> FEATURE:
<221> NAME/KEY: modified_base
<222> LOCATION: (11)..(11)
<223> OTHER INFORMATION: 5-propynyluracil
<220> FEATURE:
<221> NAME/KEY: modified_base
<222> LOCATION: (13)..(13)
<223> OTHER INFORMATION: 5-propynyluracil
<220> FEATURE:
<221> NAME/KEY: modified_base
<222> LOCATION: (14)..(14)
<223> OTHER INFORMATION: 5-propynylcytosine

<400> SEQUENCE: 48
gcacttccaa uguctaggat                                               20

<210> SEQ ID NO 49
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (5)..(5)
<223> OTHER INFORMATION: 5-propynylcytosine
<220> FEATURE:
<221> NAME/KEY: modified_base
<222> LOCATION: (7)..(7)
<223> OTHER INFORMATION: 5-propynylcytosine
<220> FEATURE:
<221> NAME/KEY: modified_base
<222> LOCATION: (8)..(8)
<223> OTHER INFORMATION: 5-propynyluracil
<220> FEATURE:
<221> NAME/KEY: modified_base
<222> LOCATION: (10)..(11)
<223> OTHER INFORMATION: 5-propynylcytosine
<220> FEATURE:
<221> NAME/KEY: modified_base
<222> LOCATION: (14)..(14)
<223> OTHER INFORMATION: 5-propynyluracil
<220> FEATURE:
<221> NAME/KEY: modified_base
<222> LOCATION: (16)..(16)
<223> OTHER INFORMATION: 5-propynyluracil

<400> SEQUENCE: 49
ggcgcacutc caauguc                                                  17

<210> SEQ ID NO 50
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (4)..(4)
<223> OTHER INFORMATION: 5-propynylcytosine
<220> FEATURE:
<221> NAME/KEY: modified_base
<222> LOCATION: (16)..(17)
<223> OTHER INFORMATION: 5-propynylcytosine

<400> SEQUENCE: 50
ttgcagcaca agaatccctc                                               20

<210> SEQ ID NO 51
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: modified_base

```
<222> LOCATION: (4)..(5)
<223> OTHER INFORMATION: 5-propynyluracil
<220> FEATURE:
<221> NAME/KEY: modified_base
<222> LOCATION: (9)..(11)
<223> OTHER INFORMATION: 5-propynylcytosine

<400> SEQUENCE: 51
tgguugagcc caac                                                     14

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
gcacttccaa tgtccaggat                                               20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gcacttccaa tgtctaggat                                               20

<210> SEQ ID NO 54
<211> LENGTH: 17
<212> TYPE: DNA
<213> ORGANISM: Artificial Sequence
<220> FEATURE:
<223> OTHER INFORMATION: Primer

<400> SEQUENCE: 54
ggcgcacttc caatgtc                                                  17

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ttgcagcaca agaatccctc                                               20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ttgcagcaca agaatccctc                                               20

<210> SEQ ID NO 57
<211> LENGTH: 14
<212> TYPE: DNA
<213> ORGANISM: Artificial Sequence
<220> FEATURE:
<223> OTHER INFORMATION: Primer

<400> SEQUENCE: 57
```

```
tggttgagcc caac                                                        14
```

```
<210> SEQ ID NO 58
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (8)..(9)
<223> OTHER INFORMATION: 5-propynylcytosine
<220> FEATURE:
<221> NAME/KEY: modified_base
<222> LOCATION: (12)..(12)
<223> OTHER INFORMATION: 5-propynyluracil
<220> FEATURE:
<221> NAME/KEY: modified_base
<222> LOCATION: (14)..(14)
<223> OTHER INFORMATION: 5-propynyluracil
<220> FEATURE:
<221> NAME/KEY: modified_base
<222> LOCATION: (15)..(15)
<223> OTHER INFORMATION: 5-propynylcytosine

<400> SEQUENCE: 58
tgcacttcca auguccagga t                                                21

<210> SEQ ID NO 59
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (8)..(9)
<223> OTHER INFORMATION: 5-propynylcytosine
<220> FEATURE:
<221> NAME/KEY: modified_base
<222> LOCATION: (12)..(12)
<223> OTHER INFORMATION: 5-propynyluracil
<220> FEATURE:
<221> NAME/KEY: modified_base
<222> LOCATION: (14)..(14)
<223> OTHER INFORMATION: 5-propynyluracil
<220> FEATURE:
<221> NAME/KEY: modified_base
<222> LOCATION: (15)..(15)
<223> OTHER INFORMATION: 5-propynylcytosine

<400> SEQUENCE: 59
tgcacttcca auguccagga t                                                21

<210> SEQ ID NO 60
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (8)..(9)
<223> OTHER INFORMATION: 5-propynylcytosine
<220> FEATURE:
<221> NAME/KEY: modified_base
<222> LOCATION: (12)..(12)
<223> OTHER INFORMATION: 5-propynyluracil
<220> FEATURE:
<221> NAME/KEY: modified_base
<222> LOCATION: (14)..(14)
<223> OTHER INFORMATION: 5-propynyluracil
<220> FEATURE:
<221> NAME/KEY: modified_base
```

<222> LOCATION: (15)..(15)
<223> OTHER INFORMATION: 5-propynylcytosine

<400> SEQUENCE: 60
tgcacttcca auguctagga t                                              21

<210> SEQ ID NO 61
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)..(6)
<223> OTHER INFORMATION: 5-propynylcytosine
<220> FEATURE:
<221> NAME/KEY: modified_base
<222> LOCATION: (8)..(8)
<223> OTHER INFORMATION: 5-propynylcytosine
<220> FEATURE:
<221> NAME/KEY: modified_base
<222> LOCATION: (9)..(9)
<223> OTHER INFORMATION: 5-propynyluracil
<220> FEATURE:
<221> NAME/KEY: modified_base
<222> LOCATION: (11)..(12)
<223> OTHER INFORMATION: 5-propynylcytosine
<220> FEATURE:
<221> NAME/KEY: modified_base
<222> LOCATION: (15)..(15)
<223> OTHER INFORMATION: 5-propynyluracil
<220> FEATURE:
<221> NAME/KEY: modified_base
<222> LOCATION: (17)..(17)
<223> OTHER INFORMATION: 5-propynyluracil

<400> SEQUENCE: 61
tggcgcacut ccaauguc                                                  18

<210> SEQ ID NO 62
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (5)..(5)
<223> OTHER INFORMATION: 5-propynylcytosine
<220> FEATURE:
<221> NAME/KEY: modified_base
<222> LOCATION: (17)..(18)
<223> OTHER INFORMATION: 5-propynylcytosine

<400> SEQUENCE: 62
tttgcagcac aagaatccct c                                              21

<210> SEQ ID NO 63
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (5)..(5)
<223> OTHER INFORMATION: 5-propynylcytosine
<220> FEATURE:
<221> NAME/KEY: modified_base
<222> LOCATION: (17)..(18)
<223> OTHER INFORMATION: 5-propynylcytosine

<400> SEQUENCE: 63
tttgcagcac aagaatccct c                                              21

<210> SEQ ID NO 64
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (5)..(5)
<223> OTHER INFORMATION: 5-propynylcytosine
<220> FEATURE:
<221> NAME/KEY: modified_base
<222> LOCATION: (17)..(18)
<223> OTHER INFORMATION: 5-propynylcytosine

<400> SEQUENCE: 64
tttgcagcac aagaatccct c                                              21

<210> SEQ ID NO 65
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (5)..(6)
<223> OTHER INFORMATION: 5-propynyluracil
<220> FEATURE:
<221> NAME/KEY: modified_base
<222> LOCATION: (10)..(12)
<223> OTHER INFORMATION: 5-propynylcytosine

<400> SEQUENCE: 65
ttgguugagc ccaac                                                     15

<210> SEQ ID NO 66
<211> LENGTH: 24
<212> TYPE: DNA
<213> ORGANISM: Artificial Sequence
<220> FEATURE:
<223> OTHER INFORMATION: Primer

<400> SEQUENCE: 66
tggcgcactt ccaatgtcca ggat                                           24

<210> SEQ ID NO 67
<211> LENGTH: 29
<212> TYPE: DNA
<213> ORGANISM: Artificial Sequence
<220> FEATURE:
<223> OTHER INFORMATION: Primer

<400> SEQUENCE: 67
tctgtcactt tgcagcacaa gaatccctc                                      29

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
tgcacttcca atgtccagga t                                              21

```
<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
tttgcagcac aagaatccct c                                           21

<210> SEQ ID NO 70
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine

<400> SEQUENCE: 70
uccgcacttc caatgtccag gat                                         23

<210> SEQ ID NO 71
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine

<400> SEQUENCE: 71
uccttgcagc acaagaatcc ctc                                         23

<210> SEQ ID NO 72
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
<222> LOCATION: (4)..(4)
<223> OTHER INFORMATION: 5-propynyluracil

<400> SEQUENCE: 72
uccugcactt ccaatgtcca ggat                                        24

<210> SEQ ID NO 73
<211> LENGTH: 24
<212> TYPE: DNA
<213> ORGANISM: Artificial Sequence
```

```
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
<222> LOCATION: (4)..(4)
<223> OTHER INFORMATION: 5-propynyluracil

<400> SEQUENCE: 73
uccuttgcag cacaagaatc cctc                                          24

<210> SEQ ID NO 74
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
<222> LOCATION: (4)..(5)
<223> OTHER INFORMATION: 5-propynyluracil

<400> SEQUENCE: 74
uccuugcact tccaatgtcc aggat                                         25

<210> SEQ ID NO 75
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)..(1)
<223> OTHER INFORMATION: 5-propynyluracil
<220> FEATURE:
<221> NAME/KEY: modified_base
<222> LOCATION: (2)..(3)
<223> OTHER INFORMATION: 5-propynylcytosine
<220> FEATURE:
<221> NAME/KEY: modified_base
<222> LOCATION: (4)..(5)
<223> OTHER INFORMATION: 5-propynyluracil

<400> SEQUENCE: 75
uccuuttgca gcacaagaat ccctc                                         25

<210> SEQ ID NO 76
<211> LENGTH: 26
<212> TYPE: DNA
<213> ORGANISM: Artificial Sequence
<220> FEATURE:
<223> OTHER INFORMATION: Primer

<400> SEQUENCE: 76
tccttcgcac ttccaatgtc caggat                                        26
```

```
<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
tccttcttgc agcacaagaa tccctc                                          26

<210> SEQ ID NO 78
<211> LENGTH: 28
<212> TYPE: DNA
<213> ORGANISM: Artificial Sequence
<220> FEATURE:
<223> OTHER INFORMATION: Primer

<400> SEQUENCE: 78
tgacgactat ccgctggttg agcccaac                                        28

<210> SEQ ID NO 79
<211> LENGTH: 27
<212> TYPE: DNA
<213> ORGANISM: Artificial Sequence
<220> FEATURE:
<223> OTHER INFORMATION: Primer

<400> SEQUENCE: 79
tgtcactttg caacacaaga atccctc                                         27

<210> SEQ ID NO 80
<211> LENGTH: 27
<212> TYPE: DNA
<213> ORGANISM: Artificial Sequence
<220> FEATURE:
<223> OTHER INFORMATION: Primer

<400> SEQUENCE: 80
tgtcactttg caacacaaga atccctc                                         27

<210> SEQ ID NO 81
<211> LENGTH: 27
<212> TYPE: DNA
<213> ORGANISM: Artificial Sequence
<220> FEATURE:
<223> OTHER INFORMATION: Primer

<400> SEQUENCE: 81
tgtcactttg cagcacaaga atccctc                                         27

<210> SEQ ID NO 82
<211> LENGTH: 28
<212> TYPE: DNA
<213> ORGANISM: Artificial Sequence
<220> FEATURE:
<223> OTHER INFORMATION: Primer

<400> SEQUENCE: 82
tgacgactat ccgctggttg agcccaac                                        28

<210> SEQ ID NO 83
<211> LENGTH: 28
<212> TYPE: DNA
<213> ORGANISM: Artificial Sequence
<220> FEATURE:
<223> OTHER INFORMATION: Primer

<400> SEQUENCE: 83
```

```
tgacgactat ccgctggttg agcccaac                                      28

<210> SEQ ID NO 84
<211> LENGTH: 27
<212> TYPE: DNA
<213> ORGANISM: Artificial Sequence
<220> FEATURE:
<223> OTHER INFORMATION: Primer

<400> SEQUENCE: 84
tgctggtgca cttccaatat ccaggat                                       27

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
tgccggtgcg ctgcctatgt ccaa                                          24

<210> SEQ ID NO 86
<211> LENGTH: 25
<212> TYPE: DNA
<213> ORGANISM: Artificial Sequence
<220> FEATURE:
<223> OTHER INFORMATION: Primer

<400> SEQUENCE: 86
tcgctctggc attagcatgg tcatt                                         25

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
tatgttgtcg tcgccgatga acgc                                          24

<210> SEQ ID NO 88
<211> LENGTH: 24
<212> TYPE: DNA
<213> ORGANISM: Artificial Sequence
<220> FEATURE:
<223> OTHER INFORMATION: Primer

<400> SEQUENCE: 88
tacgatgttg tcgtcgccga tgaa                                          24

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
tccaagtggc gcacctgtct gccat                                         25

<210> SEQ ID NO 90
<211> LENGTH: 26
<212> TYPE: DNA
<213> ORGANISM: Artificial Sequence
```

<220> FEATURE:
<223> OTHER INFORMATION: Primer

<400> SEQUENCE: 90
tcatcttggc ttttgtcaaa ggaggc                                        26

<210> SEQ ID NO 91
<211> LENGTH: 30
<212> TYPE: DNA
<213> ORGANISM: Artificial Sequence
<220> FEATURE:
<223> OTHER INFORMATION: Primer

<400> SEQUENCE: 91
tggtagttct ctcatttgtg tgacgttgca                                    30

<210> SEQ ID NO 92
<211> LENGTH: 4108
<212> TYPE: DNA
<213> ORGANISM: Artificial Sequence
<220> FEATURE:
<223> OTHER INFORMATION: Calibrant sequence pVIR001

<400> SEQUENCE: 92
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
taggtgacg cgttagaata tcaagctat gcatcaagct tggtaccgag ctcggatcca       300
ctagtaacgg ccgccagtgt gctggaattc aggactcaag ctggagtgtg gaatgcatgc     360
ttattcacat acaaactacc accatcacag cctggtaagt tcaagtttga caagactctt     420
gaacctacac acaattgcat ggctgggta acgatcaacg ttacaattcc aaaacaaaca      480
aacaccatca gtgaatttat cctctgtcac attttggata atcccaaccc ataaggtgtg     540
gagtttctac atcactgtaa atttaacata ttatgccagc caccgtaaaa cttgcttgtt     600
ccatgacgac tatgcgctgg ttgagcccaa ccagcagttt ttgcgcgtcg tccgcactga     660
cttgccagta tgccagtcat ttggtcacac aatgtagctg ggtctgtcac tttgcagcac     720
aagaatccct cgcggtgcat cgtagcagca tagcctgaag gcttcccata caggcctgga    780
agctattctt ttaacgacgt acccgtcgca actaactata ctgcgggcgg gcgcacttcc     840
aatgtcaagg atcgtgtcgg atgggtccac ctccgttcag ttttgaagcc agatgcgaaa     900
acgctctggc attagcatgg tcattttgtc ctgaattctg cagatatcca tcacactggc     960
ggccgctcga gcatgcatct agagggccca attcgcccta gtgagtcg tattacaatt     1020
cactggccgt cgttttacaa cgtcgtgact gggaaaaccc tggcgttacc caacttaatc    1080
gccttgcagc acatccccct ttcgccagct ggcgtaatag cgaagaggcc cgcaccgatc    1140
gcccttccca acagttgcgc agcctatacg tacggcagtt aaggtttac acctataaaa     1200
gagagagccg ttatcgtctg tttgtggatg tacagagtga tattattgac acgccggggc    1260
gacggatggt gatcccctg gccagtgcac gtctgctgtc agataaagtc tcccgtgaac     1320
tttacccggt ggtgcatatc ggggatgaaa gctggcgcat gatgaccacc gatatggcca    1380
gtgtgccggt ctccgttatc ggggaagaag tggctgatct cagccaccgc gaaaatgaca    1440
tcaaaaacgc cattaacctg atgttctggg aatataaat gtcaggcatg agattatcaa     1500
aaaggatctt cacctagatc cttttcacgt agaaagccag tccgcagaaa cggtgctgac    1560

```
cccggatgaa tgtcagctac tgggctatct ggacaaggga aaacgcaagc gcaaagagaa    1620
agcaggtagc ttgcagtggg cttacatggc gatagctaga ctgggcggtt ttatggacag    1680
caagcgaacc ggaattgcca gctggggcgc cctctggtaa ggttgggaag ccctgcaaag    1740
taaactggat ggctttcttg ccgccaagga tctgatggcg caggggatca agctctgatc    1800
aagagacagg atgaggatcg tttcgcatga ttgaacaaga tggattgcac gcaggttctc    1860
cggccgcttg ggtggagagg ctattcggct atgactgggc acaacagaca atcggctgct    1920
ctgatgccgc cgtgttccgg ctgtcagcgc aggggcgccc ggttcttttt gtcaagaccg    1980
acctgtccgg tgccctgaat gaactgcaag acgaggcagc gcggctatcg tggctggcca    2040
cgacgggcgt tccttgcgca gctgtgctcg acgttgtcac tgaagcggga agggactggc    2100
tgctattggg cgaagtgccg gggcaggatc tcctgtcatc tcaccttgct cctgccgaga    2160
aagtatccat catggctgat gcaatgcggc ggctgcatac gcttgatccg gctacctgcc    2220
cattcgacca ccaagcgaaa catcgcatcg agcgagcacg tactcggatg aagccggtc     2280 ttgtcgatca ggatgatctg gacgaagagc atcaggggct cgcgccagcc gaactgttcg    2340
ccaggctcaa ggcgagcatg cccgacgcg aggatctcgt cgtgacccat ggcgatgcct     2400
gcttgccgaa tatcatggtg gaaaatggcc gcttttctgg attcatcgac tgtggccggc    2460
tgggtgtggc ggaccgctat caggacatag cgttggctac ccgtgatatt gctgaagagc    2520
ttggcggcga atgggctgac cgcttcctcg tgctttacgg tatcgccgct cccgattcgc    2580
agcgcatcgc cttctatcgc cttcttgacg agttcttctg aattattaac gcttacaatt    2640
tcctgatgcg gtattttctc cttacgcatc tgtgcggtat ttcacaccgc atcaggtggc    2700
acttttcggg gaaatgtgcg cggaacccct atttgtttat ttttctaaat acattcaaat    2760
atgtatccgc tcatgagaca ataaccctga taaatgcttc aataatagca cgtgaggagg    2820
gccaccatgg ccaagttgac cagtgccgtt ccggtgctca ccgcgcgcga cgtcgccgga    2880
gcggtcgagt tctggaccga ccggctcggg ttctcccggg acttcgtgga ggacgacttc    2940
gccggtgtgg tccgggacga cgtgaccctg ttcatcagcg cggtccagga ccaggtggtg    3000
ccggacaaca ccctggcctg ggtgtgggtg cgcggcctgg acgagctgta cgccgagtgg    3060
tcggaggtcg tgtccacgaa cttccgggac gcctccgggc cggccatgac cgagatcggc    3120
gagcagccgt gggggcggga gttcgccctg cgcgacccgg ccggcaactg cgtgcacttc    3180
gtggccgagg agcaggactg acacgtgcta aaacttcatt tttaatttaa aaggatctag    3240
gtgaagatcc ttttttgataa tctcatgacc aaaatccctt aacgtgagtt ttcgttccac    3300
tgagcgtcag accccgtaga aaagatcaaa ggatcttctt gagatccttt ttttctgcgc    3360
gtaatctgct gcttgcaaac aaaaaaacca ccgctaccag cggtggtttg tttgccggat    3420
caagagctac caactctttt tccgaaggta actggcttca gcagagcgca gataccaaat    3480
actgttcttc tagtgtagcc gtagttaggc caccacttca agaactctgt agcaccgcct    3540
acatacctcg ctctgctaat cctgttacca gtggctgctg ccagtggcga taagtcgtgt    3600
cttaccgggt tggactcaag acgatagtta ccggataagg cgcagcggtc gggctgaacg    3660
gggggttcgt gcacacagcc cagcttggag cgaacgacct acaccgaact gagatacta    3720 cagcgtgagc tatgagaaag cgccacgctt cccgaaggga gaaaggcgga caggtatccg    3780
gtaagcggca gggtcggaac aggagagcgc acgagggagc ttccaggggg aaacgcctgg    3840
tatctttata gtcctgtcgg gtttcgccac ctctgacttg agcgtcgatt tttgtgatgc    3900
tcgtcagggg ggcggagcct atggaaaaac gccagcaacg cggcctttt acggttcctg     3960
```

```
gccttttgct ggccttttgc tcacatgttc tttcctgcgt tatcccctga ttctgtggat    4020
aaccgtatta ccgcctttga gtgagctgat accgctcgcc gcagccgaac gaccgagcgc    4080
agcgagtcag tgagcgagga agcggaag                                      4108

<210> SEQ ID NO 93
<211> LENGTH: 17
<212> TYPE: DNA
<213> ORGANISM: Artificial Sequence
<220> FEATURE:
<223> OTHER INFORMATION: Primer

<400> SEQUENCE: 93
gctagagcgt tttcgca                                                    17
```

COMPOSITIONS FOR USE IN IDENTIFICATION OF ALPHAVIRUSES

CROSS-REFERENCE TO RELATED APPLICATIONS

This application claims the benefit of priority to U.S. Provisional Application Ser. No. 60/550,023, filed Mar. 3, 2004, which is incorporated herein by reference in its entirety.

STATEMENT OF GOVERNMENT SUPPORT

This invention was made with United States Government support under DARPA contract MDA972-00-C-0053. The United States Government has certain rights in the invention.

FIELD OF THE INVENTION

The present invention relates generally to the field of genetic identification and quantification of alphaviruses and provides methods, compositions and kits useful for this purpose, as well as others, when combined with molecular mass analysis.

BACKGROUND OF THE INVENTION

A. Alphaviruses

Togaviridae is a family of viruses that includes the genus alphavirus. Alphaviruses are enveloped viruses with a linear, positive-sense single-stranded RNA genome. Members of the alphavirus genus include at least 30 species of arthropod-borne viruses, including Aura (AURA), Babanki (BAB), Barmah Forest (BF), Bebaru (BEB), Buggy Creek, Cabassou (CAB), Chikungunya (CHIK), Eastern equine encephalitis (EEE), Everglades (EVE), Fort Morgan (FM), Getah (GET), Highlands J (HJ), Kyzylagach (KYZ), Mayaro (MAY), Middelburg (MID), Mucambo (MUC), Ndumu (NDU), O'nyong-nyong (ONN), Pixuna (PIX), Ross River (RR), Sagiyama (SAG), Salmon pancreas disease (SPDV), Semliki Forest (SF), Una (UNA), Venezuelan equine encephalitis (VEE), Western equine encephalitis (WEE) and Whataroa (WHA) virus ("The Springer Index of Viruses," pgs. 1148-1155, Tidona and Darai eds., 2001, Springer, New York; Strauss and Strauss, Microbiol. Rev., 1994, 58, 491-562). Alphaviruses are evolutionarily differentiated based on nucleotide sequence of the nonstructural proteins, of which there are four (nsP1, nsP2, nsP3 and nsP4). The genus segregates into New World (American) and Old World (Eurasian/African/Australasian) alphaviruses based on geographic distribution. It is estimated that New World and Old World viruses diverged between 2,000 and 3,000 years ago (Harley et al., Clin. Microbiol. Rev., 2001, 14, 909-932).

Among the alphavirus species, there are seven distinct serocomplexes (SF, EEE, MID, NDU, VEE, WEE and BFV) into which members of the genus are sub-divided (Khan et al., J. Gen. Virol., 2002, 83, 3075-3084; Harley et al., Clin. Microbiol. Rev., 2001, 14, 909-932). Based on genomic sequence data from six of the seven serocomplexes, alphaviruses have been grouped into three large groups VEE/EEE, SFV and SIN. The VEE-EEE group is exclusively made up of New World viruses with a distribution in North America, South America and Central America. Members of this group include EEE, VEE, EVE, MUC and PIX. The SF group is primarily Old World, but contains one member (MAY) that is found in South America. Other members of the SF group include SF, MID, CHIK, ONN, RR, BF, GET, SAG, BEB and UNA. The SIN group is also primarily Old World, with the exception of AURA, which is a New World virus related to SIN and can be found in Brazil and Argentina. Other members of this group include SIN, WHA, BAB and KYZ. WEE, HJ and FM are considered recombinant viruses and are thus not included in any of the three groups. NDU and Buggy Creek are currently unclassified.

Many members of the alphavirus genus pose a significant health risk to humans, as well as horses, in many different geographic regions. EEE and WEE both cause a fatal encephalitis in humans and horses; however, EEE is more virulent with a mortality rate up to 50%, compared with 3-4% for WEE. VEE can also cause disease in humans and horses, but symptoms are typically flu-like and rarely lead to encephalitis. The geographic distribution for the encephalitis viruses is primarily in the Americas ("The Springer Index of Viruses," pgs. 1148-1155, Tidona and Darai eds., 2001, Springer, New York; Strauss and Strauss, Microbiol. Rev., 1994, 58, 491-562).

The SIN group of Old World viruses, including RR, ONN and CHIK, have been associated with outbreaks of acute and persistent arthritis and arthralgia (joint pain) in humans. Epidemics of acute, debilitating arthralgia have been caused by ONN and CHIK in Africa and Asia. RR, which is the etiological agent of epidemic polyarthritis, is endemic to Australia and caused a major epidemic throughout the Pacific islands in 1979. The outbreak affected over 50,000 people on the island of Fiji. Other alphaviruses have been linked to acute and persistent arthralgia in northern Europe and South Africa. Although each virus induces a somewhat different disease, infection with RR, ONN or CHIK typically causes symptoms such as generalized to severe joint pain, fever, rash, headache, nausea, myalgia and lymphadenitis. It has been reported that arthralgia associated with alphavirus infection can persist for months or years. CHIK has also been associated with a fatal hemorrhagic condition ("The Springer Index of Viruses," pgs. 1148-1155, Tidona and Darai eds., 2001, Springer, New York; Strauss and Strauss, Microbiol. Rev., 1994, 58, 491-562; Hossain et al., J. Gen. Virol., 2002, 83, 3075-3084).

Another alphavirus causing human disease and mortality is MAY, which is found in the Caribbean and South America. Mayaro virus infection causes fever, rash and arthropathy (diseases of the joint), and exhibits a mortality rate of up to 7% ("The Springer Index of Viruses," pgs. 1148-1155, Tidona and Darai eds., 2001, Springer, New York).

B. Bioagent Detection

A problem in determining the cause of a natural infectious outbreak or a bioterrorist attack is the sheer variety of organisms that can cause human disease. There are over 1400 organisms infectious to humans; many of these have the potential to emerge suddenly in a natural epidemic or to be used in a malicious attack by bioterrorists (Taylor et al., Philos. Trans. R. Soc. London B. Biol. Sci., 2001, 356, 983-989). This number does not include numerous strain variants, bioengineered versions, or pathogens that infect plants or animals.

Much of the new technology being developed for detection of biological weapons incorporates a polymerase chain reaction (PCR) step based upon the use of highly specific primers and probes designed to selectively detect individual pathogenic organisms. Although this approach is appropriate for the most obvious bioterrorist organisms, like smallpox and anthrax, experience has shown that it is very difficult to predict which of hundreds of possible pathogenic organisms might be employed in a terrorist attack. Likewise, naturally emerging human disease that has caused devastating consequence in public health has come from unexpected families of bacteria, viruses, fungi, or protozoa. Plants and animals also have their natural burden of infectious disease agents and there are equally important biosafety and security concerns for agriculture.

An alternative to single-agent tests is to do broad-range consensus priming of a gene target conserved across groups of bioagents. Broad-range priming has the potential to generate amplification products across entire genera, families, or, as with bacteria, an entire domain of life. This strategy has been successfully employed using consensus 16S ribosomal RNA primers for determining bacterial diversity, both in environmental samples (Schmidt et al., J. Bact., 1991, 173, 4371-4378) and in natural human flora (Kroes et al., Proc Nat Acad Sci (USA), 1999, 96, 14547-14552). The drawback of this approach for unknown bioagent detection and epidemiology is that analysis of the PCR products requires the cloning and sequencing of hundreds to thousands of colonies per sample, which is impractical to perform rapidly or on a large number of samples.

Conservation of sequence is not as universal for viruses, however, large groups of viral species share conserved protein-coding regions, such as regions encoding viral polymerases or helicases. Like bacteria, consensus priming has also been described for detection of several viral families, including coronaviruses (Stephensen et al., Vir. Res., 1999, 60, 181-189), enteroviruses (Qberste et al., J. Virol., 2002, 76, 1244-51); Oberste et al., J. Clin. Virol., 2003, 26, 375-7); Oberste et al., Virus Res., 2003, 91, 241-8), retroid viruses (Mack et al., Proc. Natl. Acad. Sci. U. S. A., 1988, 85, 6977-81); Seifarth et al., AIDS Res. Hum. Retroviruses, 2000, 16, 721-729); Donehower et al., J. Vir. Methods, 1990, 28, 33-46), and adenoviruses (Echavarria et al., J. Clin. Micro., 1998, 36, 3323-3326). However, as with bacteria, there is no adequate analytical method other than sequencing to identify the viral bioagent present.

In contrast to PCR-based methods, mass spectrometry provides detailed information about the molecules being analyzed, including high mass accuracy. It is also a process that can be easily automated. DNA chips with specific probes can only determine the presence or absence of specifically anticipated organisms. Because there are hundreds of thousands of species of benign pathogens, some very similar in sequence to threat organisms, even arrays with 10,000 probes lack the breadth needed to identify a particular organism.

There is a need for a method for identification of bioagents which is both specific and rapid, and in which no culture or nucleic acid sequencing is required. Disclosed in U.S. Pre-Grant Publication Nos. 2003-0027135, 2003-0082539, 2003-0228571, 2004-0209260, 2004-0219517 and 2004-0180328, and in U.S. application Ser. Nos. 10/660,997, 10/728,486, 10/754,415 and 10/829,826, all of which are commonly owned and incorporated herein by reference in their entirety, are methods for identification of bioagents (any organism, cell, or virus, living or dead, or a nucleic acid derived from such an organism, cell or virus) in an unbiased manner by molecular mass and base composition analysis of "bioagent identifying amplicons" which are obtained by amplification of segments of essential and conserved genes which are involved in, for example, translation, replication, recombination and repair, transcription, nucleotide metabolism, amino acid metabolism, lipid metabolism, energy generation, uptake, secretion and the like. Examples of these proteins include, but are not limited to, ribosomal RNAs, ribosomal proteins, DNA and RNA polymerases, RNA-dependent RNA polymerases, RNA capping and methylation enzymes, elongation factors, tRNA synthetases, protein chain initiation factors, heat shock protein groEL, phosphoglycerate kinase, NADH dehydrogenase, DNA ligases, DNA gyrases and DNA topoisomerases, helicases, metabolic enzymes, and the like.

To obtain bioagent identifying amplicons, primers are selected to hybridize to conserved sequence regions which bracket variable sequence regions to yield a segment of nucleic acid which can be amplified and which is amenable to methods of molecular mass analysis. The variable sequence regions provide the variability of molecular mass which is used for bioagent identification. Upon amplification by PCR or other amplification methods with the specifically chosen primers, an amplification product that represents a bioagent identifying amplicon is obtained. The molecular mass of the amplification product, obtained by mass spectrometry for example, provides the means to uniquely identify the bioagent without a requirement for prior knowledge of the possible identity of the bioagent. The molecular mass of the amplification product or the corresponding base composition (which can be calculated from the molecular mass of the amplification product) is compared with a database of molecular masses or base compositions and a match indicates the identity of the bioagent. Furthermore, the method can be applied to rapid parallel analyses (for example, in a multi-well plate format) the results of which can be employed in a triangulation identification strategy which is amenable to rapid throughput and does not require nucleic acid sequencing of the amplified target sequence for bioagent identification.

The result of determination of a previously unknown base composition of a previously unknown bioagent (for example, a newly evolved and heretofore unobserved virus) has downstream utility by providing new bioagent indexing information with which to populate base composition databases. The process of subsequent bioagent identification analyses is thus greatly improved as more base composition data for bioagent identifying amplicons becomes available.

The present invention provides methods of identifying unknown viruses, including viruses of the Togaviridae family and alphavirus genus. Also provided are oligonucleotide primers, compositions and kits containing the oligonucleotide primers, which define alphaviral identifying amplicons and, upon amplification, produce corresponding amplification products whose molecular masses provide the means to identify alphaviruses at the sub-species level.

SUMMARY OF THE INVENTION

The present invention provides primers and compositions comprising pairs of primers, and kits containing the same for use in identification of alphaviruses. The primers are designed to produce alphaviral bioagent identifying amplicons of DNA encoding genes essential to alphavirus replication. The invention further provides compositions comprising pairs of primers and kits containing the same, which are designed to provide species and sub-species characterization of alphaviruses.

BRIEF DESCRIPTION OF THE DRAWINGS

FIG. 3 is a pseudo four-dimensional plot of expected base compositions of alphavirus identifying amplicons obtained from amplification with primer pair no: 316 the epidemic, epizootic VEEV viruses of classes IAB-IC, ID and IIIA (which have the potential to cause severe disease in humans and animals) can be distinguished from the enzootic VEE types IE, IF, I, IIIB, IIIC, IV, V, and VI, which, in turn, are generally distinguishable from each other.

DETAILED DESCRIPTION

Figure 1:
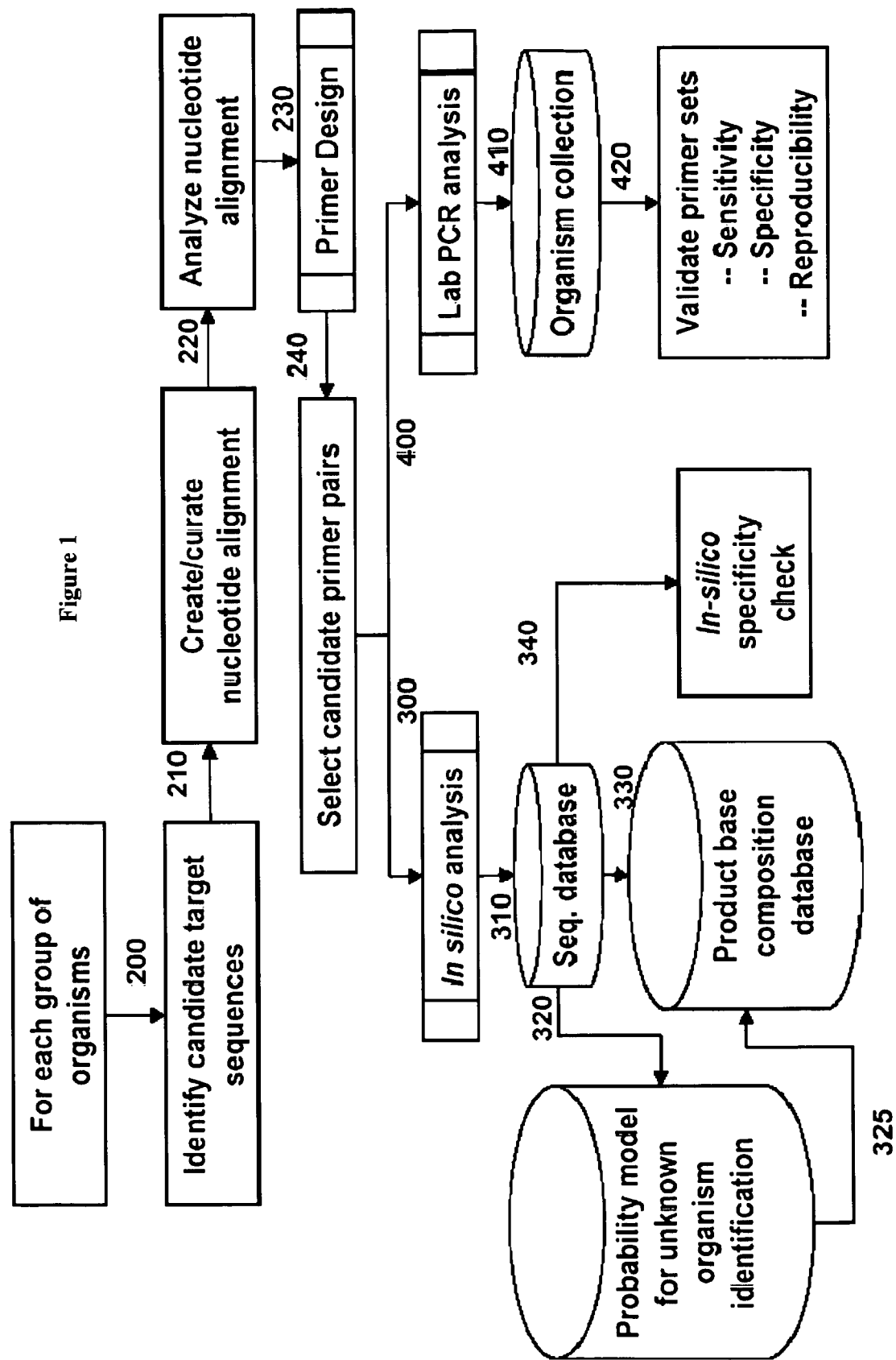
FIG. 1 is a process diagram illustrating a representative primer selection process.

In the context of the present invention, a "bioagent" is any organism, cell, or virus, living or dead, or a nucleic acid derived from such an organism, cell or virus. Examples of bioagents include, but are not limited to, cells, including but not limited to human clinical samples, cell cultures, bacterial cells and other pathogens), viruses, viroids, fungi, protists, parasites, and pathogenicity markers (including but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent which causes a disease or disorder.

As used herein, "intelligent primers" are primers that are designed to bind to highly conserved sequence regions of a bioagent identifying amplicon that flank an intervening variable region and yield amplification products which ideally provide enough variability to distinguish each individual bioagent, and which are amenable to molecular mass analysis. By the term "highly conserved," it is meant that the sequence regions exhibit between about 80-100%, or between about 90-100%, or between about 95-100% identity among all or at least 70%, at least 80%, at least 90%, at least 95%, or at least 99% of species or strains.

As used herein, "broad range survey primers" are intelligent primers designed to identify an unknown bioagent at the genus level. In some cases, broad range survey primers are able to identify unknown bioagents at the species or sub-species level. As used herein, "division-wide primers" are intelligent primers designed to identify a bioagent at the species level and "drill-down" primers are intelligent primers designed to identify a bioagent at the sub-species level. As used herein, the "sub-species" level of identification includes, but is not limited to, strains, subtypes, variants, and isolates.

As used herein, a "bioagent division" is defined as group of bioagents above the species level and includes but is not limited to, orders, families, classes, clades, genera or other such groupings of bioagents above the species level.

As used herein, a "sub-species characteristic" is a genetic characteristic that provides the means to distinguish two members of the same bioagent species. For example, one viral strain could be distinguished from another viral strain of the same species by possessing a genetic change (e.g., for example, a nucleotide deletion, addition or substitution) in one of the viral genes, such as the RNA-dependent RNA polymerase. In this case, the sub-species characteristic that can be identified using the methods of the present invention, is the genetic change in the viral polymerase.

As used herein, the term "bioagent identifying amplicon" refers to a polynucleotide that is amplified from a bioagent in an amplification reaction and which 1) provides enough variability to distinguish each individual bioagent and 2) whose molecular mass is amenable to molecular mass determination.

As used herein, a "base composition" is the exact number of each nucleobase (A, T, C and G) in a given sequence.

As used herein, a "base composition signature" (BCS) is the exact base composition (i.e., the number of A, T, G and C nucleobases) determined from the molecular mass of a bioagent identifying amplicon.

As used herein, a "base composition probability cloud" is a representation of the diversity in base composition resulting from a variation in sequence that occurs among different isolates of a given species. The "base composition probability cloud" represents the base composition constraints for each species and is typically visualized using a pseudo four-dimensional plot.

As used herein, a "wobble base" is a variation in a codon found at the third nucleotide position of a DNA triplet. Variations in conserved regions of sequence are often found at the third nucleotide position due to redundancy in the amino acid code.

In the context of the present invention, the term "unknown bioagent" may mean either: (i) a bioagent whose existence is known (such as the well known bacterial species *Staphylococcus aureus* for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

As used herein, "triangulation identification" means the employment of more than one bioagent identifying amplicons for identification of a bioagent.

In the context of the present invention, "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

As used herein, the term "etiology" refers to the causes or origins, of diseases or abnormal physiological conditions.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

The present invention provides methods for detection and identification of bioagents in an unbiased manner using bioagent identifying amplicons. Intelligent primers are selected to hybridize to conserved sequence regions of nucleic acids derived from a bioagent and which bracket variable sequence regions to yield a bioagent identifying amplicon which can be amplified and which is amenable to molecular mass determination. The molecular mass then provides a means to uniquely identify the bioagent without a requirement for prior knowledge of the possible identity of the bioagent. The molecular mass or corresponding base composition signature (BCS) of the amplification product is then matched against a database of molecular masses or base composition signatures. Furthermore, the method can be applied to rapid parallel multiplex analyses, the results of which can be employed in a triangulation identification strategy. The present method provides rapid throughput and does not require nucleic acid sequencing of the amplified target sequence for bioagent detection and identification.

Despite enormous biological diversity, all forms of life on earth share sets of essential, common features in their genomes. Since genetic data provide the underlying basis for identification of bioagents by the methods of the present invention, it is necessary to select segments of nucleic acids which ideally provide enough variability to distinguish each individual bioagent and whose molecular mass is amenable to molecular mass determination.

Unlike bacterial genomes, which exhibit conversation of numerous genes (i.e. housekeeping genes) across all organisms, viruses do not share a gene that is essential and conserved among all virus families. Therefore, viral identification is achieved within smaller groups of related viruses, such as members of a particular virus family or genus. For example, RNA-dependent RNA polymerase is present in all single-stranded RNA viruses and can be used for broad priming as well as resolution within the virus family.

In some embodiments of the present invention, at least one viral nucleic acid segment is amplified in the process of identifying the bioagent. Thus, the nucleic acid segments that can be amplified by the primers disclosed herein and that provide enough variability to distinguish each individual bioagent and whose molecular masses are amenable to molecular mass determination are herein described as bioagent identifying amplicons.

In some embodiments of the present invention, bioagent identifying amplicons comprise from about 45 to about 200 nucleobases (i.e. from about 45 to about 200 linked nucleosides). One of ordinary skill in the art will appreciate that the invention embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nucleobases in length, or any range therewithin.

It is the combination of the portions of the bioagent nucleic acid segment to which the primers hybridize (hybridization sites) and the variable region between the primer hybridization sites that comprises the bioagent identifying amplicon.

In some embodiments, bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example. Thus, in some embodiments, bioagent identifying amplicons are larger than 200 nucleobases and are amenable to molecular mass determination following restriction digestion. Methods of using restriction enzymes and cleavage primers are well known to those with ordinary skill in the art.

In some embodiments, amplification products corresponding to bioagent identifying amplicons are obtained using the polymerase chain reaction (PCR) which is a routine method to those with ordinary skill in the molecular biology arts. Other amplification methods may be used such as ligase chain reaction (LCR), low-stringency single primer PCR, and multiple strand displacement amplification (MDA) which are also well known to those with ordinary skill.

Intelligent primers are designed to bind to highly conserved sequence regions of a bioagent identifying amplicon that flank an intervening variable region and yield amplification products which ideally provide enough variability to distinguish each individual bioagent, and which are amenable to molecular mass analysis. In some embodiments, the highly conserved sequence regions exhibit between about 80-100%, or between about 90-100%, or between about 95-100% identity, or between about 99-100% identity. The molecular mass of a given amplification product provides a means of identifying the bioagent from which it was obtained, due to the variability of the variable region. Thus design of intelligent primers requires selection of a variable region with appropriate variability to resolve the identity of a given bioagent. Bioagent identifying amplicons are ideally specific to the identity of the bioagent.

Identification of bioagents can be accomplished at different levels using intelligent primers suited to resolution of each individual level of identification. Broad range survey intelligent primers are designed with the objective of identifying a bioagent as a member of a particular division (e.g., an order, family, class, clade, genus or other such grouping of bioagents above the species level of bioagents). As a non-limiting example, members of the alphavirus genus may be identified as such by employing broad range survey intelligent primers such as primers which target nsP1 or nsP4. In some embodiments, broad range survey intelligent primers are capable of identification of bioagents at the species or sub-species level.

Division-wide intelligent primers are designed with an objective of identifying a bioagent at the species level. As a non-limiting example, eastern equine encephalitis (EEE) virus, western equine encephalitis (WEE) virus and Venezuelan equine encephalitis (VEE) virus can be distinguished from each other using division-wide intelligent primers. Division-wide intelligent primers are not always required for identification at the species level because broad range survey intelligent primers may provide sufficient identification resolution to accomplishing this identification objective.

Drill-down intelligent primers are designed with the objective of identifying a bioagent at the sub-species level (including strains, subtypes, variants and isolates) based on sub-species characteristics. As one non-limiting example, subtypes IC, ID and IE of Venezuelan equine encephalitis virus can be distinguished from each other using drill-down primers. Drill-down intelligent primers are not always required for identification at the sub-species level because broad range survey intelligent primers may provide sufficient identification resolution to accomplishing this identification objective.

A representative process flow diagram used for primer selection and validation process is outlined in FIG. 1. For each group of organisms, candidate target sequences are identified (200) from which nucleotide alignments are created (210) and analyzed (220). Primers are then designed by selecting appropriate priming regions (230) which then makes possible the selection of candidate primer pairs (240). The primer pairs are then subjected to in silico analysis by electronic PCR (ePCR) (300) wherein bioagent identifying amplicons are obtained from sequence databases such as GenBank or other sequence collections (310) and checked for specificity in silico (320). Bioagent identifying amplicons obtained from GenBank sequences (310) can also be analyzed by a probability model which predicts the capability of a given amplicon to identify unknown bioagents such that the base compositions of amplicons with favorable probability scores are then stored in a base composition database (325). Alternatively, base compositions of the bioagent identifying amplicons obtained from the primers and GenBank sequences can be directly entered into the base composition database (330). Candidate primer pairs (240) are validated by in vitro amplification by a method such as PCR analysis (400) of nucleic acid from a collection of organisms (410). Amplification products thus obtained are analyzed to confirm the sensitivity, specificity and reproducibility of the primers used to obtain the amplification products (420).

Many of the important pathogens, including the organisms of greatest concern as biological weapons agents, have been completely sequenced. This effort has greatly facilitated the design of primers and probes for the detection of unknown bioagents. The combination of broad-range priming with division-wide and drill-down priming has been used very successfully in several applications of the technology, including environmental surveillance for biowarfare threat agents and clinical sample analysis for medically important pathogens.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The primers are employed as compositions for use in methods for identification of viral bioagents as follows: a primer pair composition is contacted with nucleic acid (such as, for example, DNA from a DNA virus, or DNA reverse transcribed from the RNA of an RNA virus) of an unknown viral bioagent. The nucleic acid is then amplified by a nucleic acid amplification technique, such as PCR for example, to obtain an amplification product that represents a bioagent identifying amplicon. The molecular mass of each strand of the double-stranded amplification product is determined by a molecular mass measurement technique such as mass spectrometry for example, wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known viral bioagents. A match between the molecular mass or base composition of the amplification product and the molecular mass or base composition of an analogous bioagent identifying amplicon for a known viral bioagent indicates the identity of the unknown bioagent. In some embodiments, the primer pair used is one of the primer pairs of Table 1. In some embodiments, the method is repeated using a different primer pair to resolve possible ambiguities in the identification process or to improve the confidence level for the identification assignment.

In some embodiments, a bioagent identifying amplicon may be produced using only a single primer (either the forward or reverse primer of any given primer pair), provided an appropriate amplification method is chosen, such as, for example, low stringency single primer PCR (LSSP-PCR). Adaptation of this amplification method in order to produce bioagent identifying amplicons can be accomplished by one with ordinary skill in the art without undue experimentation.

In some embodiments, the oligonucleotide primers are broad range survey primers which hybridize to conserved regions of nucleic acid encoding nsP1 of all (or between 80% and 100%, between 85% and 100%, between 90% and 100% or between 95% and 100%) known alphaviruses and produce bioagent identifying amplicons. In some embodiments, the oligonucleotide primers are broad range survey primers which hybridize to conserved regions of nucleic acid encoding nsP4 of all (or between 80% and 100%, between 85% and 100%, between 90% and 100% or between 95% and 100%) known alphaviruses and produce bioagent identifying amplicons. As used herein, the term broad range survey primers refers to primers that bind to nucleic acid encoding genes essential to alphavirus replication (e.g., for example, nsP1 and nsP4) of all (or between 80% and 100%, between 85% and 100%, between 90% and 100% or between 95% and 100%) known species of alphaviruses. In some embodiments, the broad range survey primer pairs comprise oligonucleotides ranging in length from 13-35 nucleobases, each of which have from 70% to 100% sequence identity with primer pair number 966, which corresponds to SEQ ID NOs: 21:66. In some embodiments, the broad range survey primer pairs comprise oligonucleotides ranging in length from 13-35 nucleobases, each of which have from 70% to 100% sequence identity with primer pair number 1131, which corresponds to SEQ ID NOs: 33:78.

In some cases, the molecular mass or base composition of a viral bioagent identifying amplicon defined by a broad range survey primer pair does not provide enough resolution to unambiguously identify a viral bioagent at the species level. These cases benefit from further analysis of one or more viral bioagent identifying amplicons generated from at least one additional broad range survey primer pair or from at least one additional division-wide primer pair. The employment of more than one bioagent identifying amplicon for identification of a bioagent is herein referred to as triangulation identification.

In other embodiments, the oligonucleotide primers are division-wide primers which hybridize to nucleic acid encoding genes of species within a genus of viruses. In other embodiments, the oligonucleotide primers are drill-down primers which enable the identification of sub-species characteristics. Drill down primers provide the functionality of producing bioagent identifying amplicons for drill-down analyses such as strain typing when contacted with nucleic acid under amplification conditions. Identification of such sub-species characteristics is often critical for determining proper clinical treatment of viral infections. In some embodiments, sub-species characteristics are identified using only broad range survey primers and division-wide and drill-down primers are not used.

In some embodiments, the primers used for amplification hybridize to and amplify genomic DNA, DNA of bacterial plasmids, DNA of DNA viruses or DNA reverse transcribed from RNA of an RNA virus.

In some embodiments, the primers used for amplification hybridize directly to viral RNA and act as reverse transcription primers for obtaining DNA from direct amplification of viral RNA. Methods of amplifying RNA using reverse transcriptase are well known to those with ordinary skill in the art and can be routinely established without undue experimentation.

One with ordinary skill in the art of design of amplification primers will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event. (e.g., for example, a loop structure or a hairpin structure). The primers of the present invention may comprise at least 70%, at least 75%, at least 80%, at least 85%, at least 90%, at least 95% or at least 99% sequence identity with any of the primers listed in Table 1. Thus, in some embodiments of the present invention, an extent of variation of 70% to 100%, or any range therewithin, of the sequence identity is possible relative to the specific primer sequences disclosed herein. Determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer.

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of viral nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range therewithin) sequence identity with the primer sequences specifically disclosed herein. Thus, for example, a primer may have between 70% and 100%, between 75% and 100%, between 80% and 100%, and between 95% and 100% sequence identity with SEQ ID NO: 21. Likewise, a primer may have similar sequence identity with any other primer whose nucleotide sequence is disclosed herein.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding bioagent identifying amplicon.

In some embodiments of the present invention, the oligonucleotide primers are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated A residues as a result of the non-specific enzyme activity of Taq polymerase (Magnuson et al., Biotechniques, 1996, 21, 700-709), an occurrence which may lead to ambiguous results arising from molecular mass analysis.

In some embodiments of the present invention, primers may contain one or more universal bases. Because any variation (due to codon wobble in the $3^{rd}$ position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-β-D-ribofuranosyl)-imidazole-4-carboxamide (Sala et al., Nucl. Acids Res., 1996, 24, 3302-3306).

In some embodiments, to compensate for the somewhat weaker binding by the wobble base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S Pre-Grant Publication No. 2003-0170682, which is also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, to enable broad priming of rapidly evolving RNA viruses, primer hybridization is enhanced using primers and probes containing 5-propynyl deoxy-cytidine and deoxy-thymidine nucleotides. These modified primers and probes offer increased affinity and base pairing selectivity.

In some embodiments, non-template primer tags are used to increase the melting temperature ($T_m$) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon from its molecular mass.

In some embodiments of the present invention, the mass modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$.

In some cases, a molecular mass of a given bioagent identifying amplicon alone does not provide enough resolution to unambiguously identify a given bioagent. The employment of more than one bioagent identifying amplicon for identification of a bioagent is herein referred to as triangulation identification. Triangulation identification is pursued by analyzing a plurality of bioagent identifying amplicons selected within multiple core genes. This process is used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well PCR methods are well known to those with ordinary skill in the arts of rapid throughput amplification of nucleic acids.

In some embodiments, the molecular mass of a given bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), time of flight (TOF), ion trap, quadrupole, magnetic sector, Q-TOF, and triple quadrupole.

Although the molecular mass of amplification products obtained using intelligent primers provides a means for identification of bioagents, conversion of molecular mass data to a base composition signature is useful for certain analyses. As used herein, a base composition signature (BCS) is the exact base composition determined from the molecular mass of a bioagent identifying amplicon. In one embodiment, a BCS provides an index of a specific gene in a specific organism.

In some embodiments, conversion of molecular mass data to a base composition is useful for certain analyses. As used herein, a base composition is the exact number of each nucleobase (A, T, C and G).

RNA viruses depend on error-prone polymerases for replication and therefore their nucleotide sequences (and resultant base compositions) drift over time within the functional constraints allowed by selection pressure. Base composition probability distribution of a viral species or group represents a probabilistic distribution of the above variation in the A, C, G and T base composition space and can be derived by analyzing base compositions of all known isolates of that particular species.

In some embodiments, assignment of base compositions to experimentally determined molecular masses is accomplished using base composition probability clouds. Base compositions, like sequences, vary slightly from isolate to isolate within species. It is possible to manage this diversity by building base composition probability clouds around the composition constraints for each species. This permits identification of organisms in a fashion similar to sequence analysis. A pseudo four-dimensional plot can be used to visualize the concept of base composition probability clouds. Optimal primer design requires optimal choice of bioagent identifying amplicons and maximizes the separation between the base composition signatures of individual bioagents. Areas where clouds overlap indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

The present invention provides bioagent classifying information similar to DNA sequencing and phylogenetic analysis at a level sufficient to identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is thus greatly improved as more BCS indexes become available in base composition databases.

Figure 2:
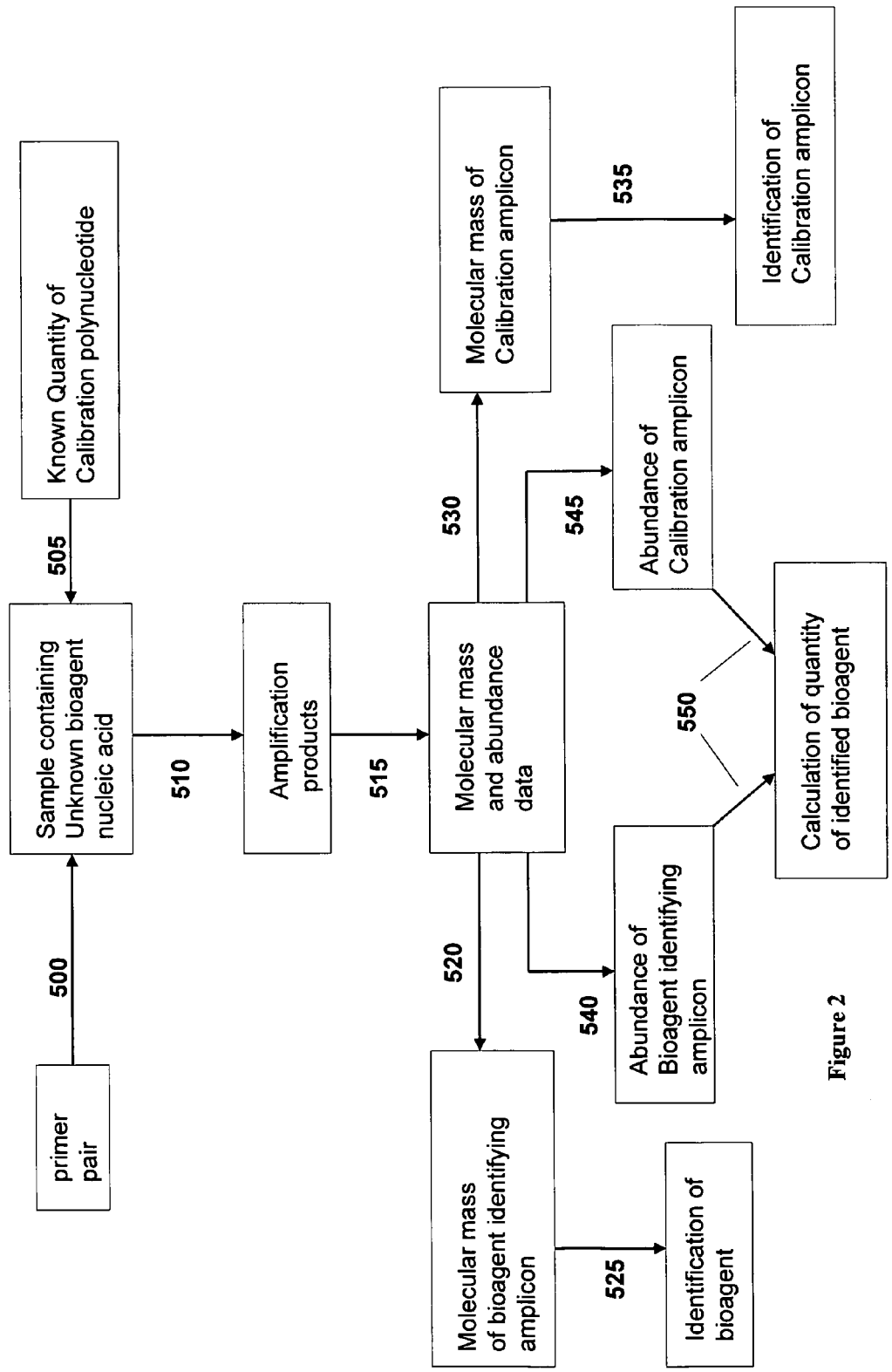
FIG. 2 is a representative process diagram for identification and determination of the quantity of a bioagent in a sample.

In some embodiments, the identity and quantity of an unknown bioagent can be determined using the process illustrated in FIG. 2. Primers (500) and a known quantity of a calibration polynucleotide (505) are added to a sample containing nucleic acid of an unknown bioagent. The total nucleic acid in the sample is then subjected to an amplification reaction (510) to obtain amplification products. The molecular masses of amplification products are determined (515) from which are obtained molecular mass and abundance data. The molecular mass of the bioagent identifying amplicon (520) provides the means for its identification (525) and the molecular mass of the calibration amplicon obtained from the calibration polynucleotide (530) provides the means for its identification (535). The abundance data of the bioagent identifying amplicon is recorded (540) and the abundance data for the calibration data is recorded (545), both of which are used in a calculation (550) which determines the quantity of unknown bioagent in the sample.

A sample comprising an unknown bioagent is contacted with a pair of primers which provide the means for amplification of nucleic acid from the bioagent, and a known quantity of a polynucleotide that comprises a calibration sequence. The nucleic acids of the bioagent and of the calibration sequence are amplified and the rate of amplification is reasonably assumed to be similar for the nucleic acid of the bioagent and of the calibration sequence. The amplification reaction then produces two amplification products: a bioagent identifying amplicon and a calibration amplicon. The bioagent identifying amplicon and the calibration amplicon should be distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample.

In some embodiments, construction of a standard curve where the amount of calibration polynucleotide spiked into the sample is varied, provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single vector which functions as the calibration polynucleotide. Multiplex amplification methods are well known to those with ordinary skill and can be performed without undue experimentation.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide should give rise to a calibration amplicon. Failure to produce a measurable calibration amplicon indicates a failure of amplification or subsequent analysis step such as amplicon purification or molecular mass determination. Reaching a conclusion that such failures have occurred is in itself, a useful event.

In some embodiments, the calibration sequence is comprised of DNA. In some embodiments, the calibration sequence is comprised of RNA.

In some embodiments, the calibration sequence is inserted into a vector which then itself functions as the calibration polynucleotide. In some embodiments, more than one calibration sequence is inserted into the vector that functions as the calibration polynucleotide. Such a calibration polynucleotide is herein termed a "combination calibration polynucleotide." The process of inserting polynucleotides into vectors is routine to those skilled in the art and can be accomplished without undue experimentation. Thus, it should be recognized that the calibration method should not be limited to the embodiments described herein. The calibration method can be applied for determination of the quantity of any bioagent identifying amplicon when an appropriate standard calibrant polynucleotide sequence is designed and used. The process of choosing an appropriate vector for insertion of a calibrant is also a routine operation that can be accomplished by one with ordinary skill without undue experimentation.

Bioagents that can be identified by the methods of the present invention include RNA viruses. The genomes of RNA viruses can be positive-sense single-stranded RNA, negative-sense single-stranded RNA or double-stranded RNA. Examples of RNA viruses with positive-sense single-stranded genomes include, but are not limited to members of the Caliciviridae, Picornaviridae, Flaviviridae, Togaviridae, Retroviridae and Coronaviridae families. Examples of RNA viruses with negative-sense single-stranded RNA genomes include, but are not limited to, members of the Filoviridae, Rhabdoviridae, Bunyaviridae, Orthomyxoviridae, Paramyxoviridae and Arenaviridae families. Examples of RNA viruses with double-stranded RNA genomes include, but are not limited to, members of the Reoviridae and Bimaviridae families.

In some embodiments of the present invention, RNA viruses are identified by first obtaining RNA from an RNA virus, or a sample containing or suspected of containing an RNA virus, obtaining corresponding DNA from the RNA by reverse transcription, amplifying the DNA to obtain one or more amplification products using one or more pairs of oligonucleotide primers that bind to conserved regions of the RNA viral genome, which flank a variable region of the genome, determining the molecular mass or base composition of the one or more amplification products and comparing the molecular masses or base compositions with calculated or experimentally determined molecular masses or base compositions of known RNA viruses, wherein at least one match identifies the RNA virus. Methods of isolating RNA from RNA viruses and/or samples containing RNA viruses, and reverse transcribing RNA to DNA are well known to those of skill in the art.

Alphaviruses represent RNA virus examples of bioagents which can be identified by the methods of the present invention. Alphaviruses are extremely diverse at the nucleotide and protein sequence levels and are thus difficult to detect and identify using currently available diagnostic techniques.

In one embodiment of the present invention, the alphavirus target gene is nsP4, which is the viral RNA-dependent RNA polymerase. In another embodiment, the target gene is nsP1, which functions to cap and methylate the 5' end of genomic and subgenomic alphaviral RNAs.

In other embodiments of the present invention, the intelligent primers produce bioagent identifying amplicons within stable and highly conserved regions of alphaviral genomes. The advantage to characterization of an amplicon in a highly conserved region is that there is a low probability that the region will evolve past the point of primer recognition, in which case, the amplification step would fail. Such a primer set is thus useful as a broad range survey-type primer. In another embodiment of the present invention, the intelligent primers produce bioagent identifying amplicons in a region which evolves more quickly than the stable region described above. The advantage of characterization bioagent identifying amplicon corresponding to an evolving genomic region is that it is useful for distinguishing emerging strain variants.

The present invention also has significant advantages as a platform for identification of diseases caused by emerging viruses. The present invention eliminates the need for prior knowledge of bioagent sequence to generate hybridization probes. Thus, in another embodiment, the present invention provides a means of determining the etiology of a virus infection when the process of identification of viruses is carried out in a clinical setting and, even when the virus is a new species never observed before. This is possible because the methods are not confounded by naturally occurring evolutionary variations (a major concern for characterization of viruses which evolve rapidly) occurring in the sequence acting as the template for production of the bioagent identifying amplicon. Measurement of molecular mass and determination of base composition is accomplished in an unbiased manner without sequence prejudice.

Another embodiment of the present invention also provides a means of tracking the spread of any species or strain of virus when a plurality of samples obtained from different locations are analyzed by the methods described above in an epidemiological setting. In one embodiment, a plurality of samples from a plurality of different locations are analyzed with primers which produce bioagent identifying amplicons, a subset of which contain a specific virus. The corresponding locations of the members of the virus-containing subset indicate the spread of the specific virus to the corresponding locations.

The present invention also provides kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more primer pairs recited in Table 1.

In some embodiments, the kit may comprise one or more broad range survey primer(s), division wide primer(s), or drill-down primer(s), or any combination thereof. A kit may be designed so as to comprise particular primer pairs for identification of a particular bioagent. For example, a broad range survey primer kit may be used initially to identify an unknown bioagent as a member of the alphavirus genus. Another example of a division-wide kit may be used to distinguish eastern equine encephalitis virus, western equine encephalitis virus and Venezuelan equine encephalitis virus from each other. A drill-down kit may be used, for example, to distinguish different subtypes of Venezuelan equine encephalitis virus, or to identify genetically engineered alphaviruses. In some embodiments, any of these kits may be combined to comprise a combination of broad range survey primers and division-wide primers so as to be able to identify the species of an unknown bioagent.

In some embodiments, the kit may contain standardized calibration polynucleotides for use as internal amplification calibrants. Internal calibrants are described in commonly owned U.S. Patent Application Ser. No: 60/545,425 which is incorporated herein by reference in its entirety.

In some embodiments, the kit may also comprise a sufficient quantity of reverse transcriptase (if an RNA virus is to be identified for example), a DNA polymerase, suitable nucleoside triphosphates (including any of those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a table of measured or calculated molecular masses and/or base compositions of bioagents using the primer pairs of the kit.

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

EXAMPLES

Example 1

Selection of Primers that Define Alphavirus Identifying Amplicons

For design of primers that define alphaviral bioagent identifying amplicons, relevant sequences from, for example, GenBank were obtained, aligned and scanned for regions where pairs of PCR primers would amplify products of about 45 to about 200 nucleotides in length and distinguish species and/or sub-species from each other by their molecular masses or base compositions. A typical process shown in FIG. 1 is employed.

A database of expected base compositions for each primer region is generated using an in silico PCR search algorithm, such as (ePCR). An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs.

Table 1 represents a collection of primers (sorted by forward primer name) designed to identify alphaviruses using the methods described herein. Primer sites were identified on two essential alphaviral genes, nsP1 (the RNA capping and methylation enzyme) and nsP4, the RNA-dependent RNA polymerase). The forward or reverse primer name shown in Table 1 indicates the gene region of the viral genome to which the primer hybridizes relative to a reference sequence. For example, the forward primer name AV_NC001449_888_901P_F indicates a forward primer that hybridizes to residues 888-901 of an alphavirus reference sequence represented by GenBank Accession No. NC001449 (SEQ ID NO: 1). In Table 1, $U^a$=5-propynyluracil; $C^a$=5-propynylcytosine; *=phosphorothioate linkage. The primer pair number is an in-house database index number.

TABLE 1

Primer Pairs for Identification of Alphavirus Bioagents

| Primer pair number | For. primer name | Forward sequence | For. SEQ ID NO: | Reverse primer name | Reverse sequence | Reverse SEQ ID NO: |
|---|---|---|---|---|---|---|
| 302 | AV_NC001449_159_178P_F | AATGCTAGAGC$^a$GU$^a$U$^a$TU$^a$C$^a$GCA | 2 | AV_NC001449_225_224P_4 | GCACTTC$^a$C$^a$AAU$^a$GU$^a$C$^a$CAGGAT | 47 |
| 303 | AV_NC001449_159_178P_F | AATGCTAGAGC$^a$GU$^a$U$^a$TU$^a$C$^a$GCA | 3 | AV_NC001449_225_224P_2_R | GCACTTC$^a$C$^a$AAU$^a$GU$^a$C$^a$TAGGAT | 48 |
| 304 | AV_NC001449_162_178P_F | GCTAGAGC$^a$GU$^a$U$^a$TU$^a$C$^a$GCA | 4 | AV_NC001449_231_247P_R | GGCGC$^a$AC$^a$U$^a$TC$^a$C$^a$AAU$^a$GU$^a$C | 49 |
| 306 | AV_NC001449_888_904P_F | TGC$^a$GAAGGGU$^a$ACGTCGT | 5 | AV_NC001449_972_991P_R | TTGC$^a$AGCACAAGAATC$^a$C$^a$CTC | 50 |
| 307 | AV_NC001449_1057_1072P_F | TGU$^a$GTGAC$^a$C$^a$AGAU$^a$GAC | 6 | AV_NC001449_1122_1135P_R | TGGU$^a$U$^a$GAGC$^a$C$^a$C$^a$AAC | 51 |
| 314 | AV_NC001449_159_178_F | AATGCTAGAGCGTTTTCGCA | 7 | AV_NC001449_225_244_R | GCACTTCCAATGTCCAGGAT | 52 |
| 315 | AV_NC001449_159_178_F | AATGCTAGAGCGTTTTCGCA | 8 | AV_NC001449_225_244_2_R | GCACTTCCAATGTCTAGGAT | 53 |
| 316 | AV_NC001449_162_178_F | GCTAGAGCGTTTTCGCA | 9 | AV_NC001449_231_247_R | GGCGCACTTCCAATGTC | 54 |
| 317 | AV_NC001449_888_901_F | TGCGAAGGGTACGT | 10 | AV_NC001449_972_991_R | TTGCAGCACAAGAATCCCTC | 55 |
| 318 | AV_NC001449_888_904_F | TGCGAAGGGTACGTCGT | 11 | AV_NC001449_972_991_R | TTGCAGCACAAGAATCCCTC | 56 |
| 319 | AV_NC001449_1057_1072_F | TGTGTGACCAGATGAC | 12 | AV_NC001449_1122_1135_R | TGGTTGAGCCCAAC | 57 |
| 494 | AV_NC001449_158_178P_F | TAATGCTAGAGC$^a$GU$^a$U$^a$TU$^a$C$^a$GCA | 13 | AV_NC001449_225_245P_R | TGCACTTC$^a$C$^a$AAU$^a$GU$^a$C$^a$CAGGAT | 58 |
| 494 | AV_NC001449_159_178P_F | TAATGCTAGAGC$^a$GU$^a$U$^a$TU$^a$C$^a$GCA | 14 | AV_NC001449_225_245P_R | TGCACTTC$^a$C$^a$AAU$^a$GU$^a$C$^a$CAGGAT | 59 |
| 495 | AV_NC001449_159_178P_F | TAATGCTAGAGC$^a$GU$^a$U$^a$TU$^a$C$^a$GCA | 15 | AV_NC001449_225_245P_2_R | TGCACTTC$^a$C$^a$AAU$^a$GU$^a$C$^a$TAGGAT | 60 |
| 496 | AV_NC001449_161_178P_F | TGCTAGAGC$^a$GU$^a$U$^a$TU$^a$C$^a$GCA | 16 | AV_NC001449_231_248P_R | TGGCGC$^a$AC$^a$U$^a$TC$^a$C$^a$AAU$^a$GU$^a$C | 61 |

TABLE 1-continued

Primer Pairs for Identification of Alphavirus Bioagents

| Primer pair number | For. primer name | Forward sequence | For. SEQ ID NO: | Reverse primer name | Reverse sequence | Reverse SEQ ID NO: |
|---|---|---|---|---|---|---|
| 497 | AV_NC001449_887_901P_F | TTGC$^a$GAAGGGU$^a$ACGT | 17 | AV_NC001449_972_992P_R | TTTGC$^a$AGCACAAGAAT C$^a$C$^a$CTC | 62 |
| 498 | AV_NC001449_887_904P_F | TTGC$^a$GAAGGGU$^a$ACGTCGT | 18 | AV_NC001449_972_992P_R | TTTGC$^a$AGCACAAGAAT C$^a$C$^a$CTC | 63 |
| 498 | AV_NC001449_887_904P_F | TTGC$^a$GAAGGGU$^a$ACGTCGT | 19 | AV_NC001449_972_992P_R | TTTGC$^a$AGCACAAGAAT C$^a$C$^a$CTC | 64 |
| 499 | AV_NC001449_1056_072P_F | TTGU$^a$GTGAC$^a$C$^a$AGAU$^a$GAC | 20 | AV_NC001449_1122_1136P_R | TTGGU$^a$U$^a$GAGC$^a$C$^a$AAC | 65 |
| 966 | AV_NC_001449_151_178_F | TCCATGCTAATGCTAGAGC GTTTTCGCA | 21 | AV_NC_001449_225_248_R | TGGCGCACTTCCAATGT CCAGGAT | 66 |
| 967 | AV_NC_001449_881_904_F | TGTCAGTTGCGAAGGGTAC GTCGT | 22 | AV_NC_001449_972_1000_R | TCTGTCACTTTGCAGCA CAAGAATCCCTC | 67 |
| 968 | AV_NC_001449_158_178_F | TAATGCTAGAGCGTTTTCG CA | 23 | AV_NC_001449_225_245_R | TGCACTTCCAATGTCCA GGAT | 68 |
| 969 | AV_NC_001449_887_904_F | TTGCGAAGGGTACGTCGT | 24 | AV_NC_001449_972_992_R | TTTGCAGCACAAGAATC CCTC | 69 |
| 970 | AV_NC_001449_156_178P_F | U$^a$C$^a$C$^a$AATGCTAGAGCGTT TTCGCA | 25 | AV_NC_001449_225_247P_R | U$^a$C$^a$C$^a$GCACTTCCAATG TCCAGGAT | 70 |
| 971 | AV_NC_001449_885_904P_F | U$^a$C$^a$C$^a$TGCGAAGGGTACGT CGT | 26 | AV_NC_001449_972_994P_R | U$^a$C$^a$C$^a$TTGCAGCACAAG AATCCCTC | 71 |
| 972 | AV_NC_001449_155_178P_F | U$^a$C$^a$C$^a$U$^a$AATGCTAGAGCG TTTTCGCA | 27 | AV_NC_001449_225_248P_R | U$^a$C$^a$C$^a$U$^a$GCACTTCCAA TGTCCAGGAT | 72 |
| 973 | AV_NC_001449_884_904P_F | U$^a$C$^a$C$^a$U$^a$TGCGAAGGGTAC GTCGT | 28 | AV_NC_001449_972_995P_R | U$^a$C$^a$C$^a$U$^a$TTGCAGCACA AGAATCCCTC | 73 |
| 974 | AV_NC_001449_154_178P_F | U$^a$C$^a$C$^a$U$^a$U$^a$AATGCTAGAGC GTTTTCGCA | 29 | AV_NC_001449_225_249P_R | U$^a$C$^a$C$^a$U$^a$U$^a$GCACTTCCA ATGTCCAGGAT | 74 |
| 975 | AV_NC_001449_883_904P_F | U$^a$C$^a$C$^a$U$^a$U$^a$TGCGAAGGGTA CGTCGT | 30 | AV_NC_001449_972_996P_R | U$^a$C$^a$C$^a$U$^a$U$^a$TTGCAGCAC AAGAATCCCTC | 75 |
| 976 | AV_NC_001449_153_178_F | TCCTTCAATGCTAGAGCGT TTTCGCA | 31 | AV_NC_001449_225_250_R | TCCTTCGCACTTCCAAT GTCCAGGAT | 76 |
| 977 | AV_NC_001449_882_904_F | TCCTTCTGCGAAGGGTACG TCGT | 32 | AV_NC_001449_972_997_R | TCCTTCTTGCAGCACAA GAATCCCTC | 77 |
| 1131 | AV_NC_001449_1045_1072_F | TGCCAGCTACACTGTGCGA CCAGATGAC | 33 | AV_NC_001449_1122_1149_R | TGACGACTATCCGCTGG TTGAGCCCAAC | 78 |
| 1146 | AV_NC_001449_878_901_F | TATTGTCAGTTGCGAAGGG TACGT | 34 | AV_NC_001449_972_998_R | TGTCACTTTGCAACACA AGAATCCCTC | 79 |
| 1147 | AV_NC_001449_878_901_2_F | TATTGTCAGTTGCGACGGG TACGT | 35 | AV_NC_001449_972_998_R | TGTCACTTTGCAACACA AGAATCCCTC | 80 |
| 1148 | AV_NC_001449_876_901_F | TCTATAGTCAGTTGCGACG GGTACGT | 36 | AV_NC_001449_972_998_2_R | TGTCACTTTGCAGCACA AGAATCCCTC | 81 |
| 1149 | AV_NC_001449_1045_1075_F | TGTCAGCTACATTGTGTGA CCAAATGACTGG | 37 | AV_NC_001449_1122_1149_2_R | TGACGACTATCCGCTGG TTGAGCCCAAC | 82 |
| 1150 | AV_NC_001449_1045_1075_2_F | TACCAGCCACACTTTGCGA TCAGATGACAGG | 38 | AV_NC_001449_1122_1149_2_R | TGACGACTATCCGCTGG TTGAGCCCAAC | 83 |
| 2048 | AV_NC_001449_151_178_2_F | TCCATGCTAACGCCAGAGC GTTTTCGCA | 39 | AV_NC_001449_225_251_R | TGCTGGTGCACTTCCAA TATCCAGGAT | 84 |
| 2049 | AV_NC_001449_151_178_2_F | TCCATGCTAACGCCAGAGC GTTTTCGCA | 40 | AV_NC_001449_228_251_R | TGCCGGTGCGCTGCCTA TGTCCAA | 85 |

TABLE 1-continued

Primer Pairs for Identification of Alphavirus Bioagents

| Primer pair number | For. primer name | Forward sequence | For. SEQ ID NO: | Reverse primer name | Reverse sequence | Reverse SEQ ID NO: |
|---|---|---|---|---|---|---|
| 2050 | AV_NC_001449_62_86_F | TGACGTAGACCCCCAGAGTCCGTTT | 41 | AV_NC_001449_147_171_R | TCGCTCTGGCATTAGCATGGTCATT | 86 |
| 2051 | AV_NC_001449_6971_6997_F | TGGCGCTATGATGAAATCTGGAATGTT | 42 | AV_NC_001449_7083_7106_R | TATGTTGTCGTCGCCGATGAACGC | 87 |
| 2052 | AV_NC_001449_6971_6997_F | TGGCGCTATGATGAAATCTGGAATGTT | 43 | AV_NC_001449_7086_7109_R | TACGATGTTGTCGTCGCCGATGAA | 88 |
| 2053 | AV_NC_001449_7082_7105_F | TGCCTTCATCGGCGATGACAACAT | 44 | AV_NC_001449_7134_7158_R | TCCAAGTGGCGCACCTGTCTGCCAT | 89 |
| 2054 | AV_NC_001449_6742_6772_F | TGTCGGCCGAGGATTTTGATGCTATCATAGC | 45 | AV_NC_001449_6816_6841_R | TCATCTTGGCTTTTGTCAAAGGAGGC | 90 |
| 2055 | AV_NC_001449_6254_6280_F | TGCGGTACCGTCACCATTTCAGAACAC | 46 | AV_NC_001449_6318_6347_R | TGGTAGTTCTCTCATTTGTGTGACGTTGCA | 91 |

In some embodiments, primer pairs for identification of alphavirus bioagents comprise forward primer sequence GCTAGAGCGTTTTCGCA (SEQ. ID NO: 93).

Example 2

One-Step RT-PCR of RNA Virus Samples

RNA was isolated from virus-containing samples according to methods well known in the art. To generate bioagent identifying amplicons for RNA viruses, a one-step RT-PCR protocol was developed. All RT-PCR reactions were assembled in 50 µl reactions in the 96 well microtiter plate format using a Packard MPII liquid handling robotic platform and MJ Dyad® thermocyclers (MJ research, Waltham, Mass.). The RT-PCR reaction consisted of 4 units of Amplitaq Gold®, 1.5× buffer II (Applied Biosystems, Foster City, Calif.), 1.5 mM MgCl$_2$, 0.4 M betaine, 10 mM DTT, 20 mM sorbitol, 50 ng random primers (Invitrogen, Carlsbad, Calif.), 1.2 units Superasin (Ambion, Austin, Tex.), 100 ng polyA DNA, 2 units Superscript III (Invitrogen, Carlsbad, Calif.), 400 ng T4 Gene 32 Protein (Roche Applied Science, Indianapolis, Ind.), 800 µM dNTP mix, and 250 nM of each primer.

The following RT-PCR conditions were used to amplify the sequences used for mass spectrometry analysis: 60° C. for 5 minutes, 4° C. for 10 minutes, 55° C. for 45 minutes, 95° C. for 10 minutes followed by 8 cycles of 95° C. for 30 seconds, 48° C. for 30 seconds, and 72° C. for 30 seconds, with the 48° C. annealing temperature increased 0.9° C. after each cycle. The PCR reaction was then continued for 37 additional cycles of 95° C. for 15 seconds, 56° C. for 20 seconds, and 72° C. for 20 seconds. The reaction concluded with 2 minutes at 72° C.

Example 3

Solution Capture Purification of PCR Products for Mass Spectrometry with Ion Exchange Resin-Magnetic Beads For solution capture of nucleic acids with ion exchange resin linked to magnetic beads, 25 µL of a 2.5 mg/mL suspension of BioClon amine terminated supraparamagnetic beads were added to 25 to 50 µl of a PCR (or RT-PCR) reaction containing approximately 10 µM of a typical PCR amplification product. The above suspension was mixed for approximately 5 minutes by vortexing or pipetting, after which the liquid was removed after using a magnetic separator. The beads containing bound PCR amplification product were then washed 3× with 50 mM ammonium bicarbonate/50% MeOH or 100 mM ammonium bicarbonate/50% MeOH, followed by three more washes with 50% MeOH. The bound PCR amplicon was eluted with 25 mM piperidine, 25 mM imidazole, 35% MeOH, plus peptide calibration standards.

Example 4

Mass Spectrometry and Base Composition Analysis

The ESI-FTICR mass spectrometer is based on a Bruker Daltonics (Billerica, Mass.) Apex II 70e electrospray ionization Fourier transform ion cyclotron resonance mass spectrometer that employs an actively shielded 7 Tesla superconducting magnet. The active shielding constrains the majority of the fringing magnetic field from the superconducting magnet to a relatively small volume. Thus, components that might be adversely affected by stray magnetic fields, such as CRT monitors, robotic components, and other electronics, can operate in close proximity to the FTICR spectrometer. All aspects of pulse sequence control and data acquisition were performed on a 600 MHz Pentium II data station running Bruker's Xmass software under Windows NT 4.0 operating system. Sample aliquots, typically 15 µl, were extracted directly from 96-well microtiter plates using a CTC HTS PAL autosampler (LEAP Technologies, Carrboro, N.C.) triggered by the FTICR data station. Samples were injected directly into a 10 µl sample loop integrated with a fluidics handling system that supplies the 100 µl/hr flow rate to the ESI source. Ions were formed via electrospray ionization in a modified Analytica (Branford, Conn.) source employing an off axis, grounded electrospray probe positioned approximately 1.5 cm from the metalized terminus of a glass desolvation capillary. The atmospheric pressure end of the glass capillary was biased at 6000 V relative to the ESI needle during data acquisition. A counter-current flow of dry N$_2$ was employed to assist in the desolvation process. Ions were accumulated in an external ion reservoir comprised of an rf-only hexapole, a skimmer cone, and an auxiliary gate electrode, prior to injection into the trapped ion cell where they were mass analyzed. Ionization duty cycles>99% were achieved by simultaneously accumulating ions in the external ion reservoir during ion detection. Each detection event consisted of 1M data points digitized over 2.3 s. To improve the signal-to-noise ratio (S/N), 32 scans were co-added for a total data acquisition time of 74 s.

The ESI-TOF mass spectrometer is based on a Bruker Daltonics MicroTOF™. Ions from the ESI source undergo orthogonal ion extraction and are focused in a reflectron prior to detection. The TOF and FTICR are equipped with the same automated sample handling and fluidics described above. Ions are formed in the standard MicroTOF™ ESI source that is equipped with the same off-axis sprayer and glass capillary as the FTICR ESI source. Consequently, source conditions were the same as those described above. External ion accumulation was also employed to improve ionization duty cycle during data acquisition. Each detection event on the TOF was comprised of 75,000 data points digitized over 75 µs.

The sample delivery scheme allows sample aliquots to be rapidly injected into the electrospray source at high flow rate and subsequently be electrosprayed at a much lower flow rate for improved ESI sensitivity. Prior to injecting a sample, a bolus of buffer was injected at a high flow rate to rinse the transfer line and spray needle to avoid sample contamination/carryover. Following the rinse step, the autosampler injected the next sample and the flow rate was switched to low flow. Following a brief equilibration delay, data acquisition commenced. As spectra were co-added, the autosampler continued rinsing the syringe and picking up buffer to rinse the injector and sample transfer line. In general, two syringe rinses and one injector rinse were required to minimize sample carryover. During a routine screening protocol a new sample mixture was injected every 106 seconds. More recently a fast wash station for the syringe needle has been implemented which, when combined with shorter acquisition times, facilitates the acquisition of mass spectra at a rate of just under one spectrum/minute.

Raw mass spectra were post-calibrated with an internal mass standard and deconvoluted to monoisotopic molecular masses. Unambiguous base compositions were derived from the exact mass measurements of the complementary single-stranded oligonucleotides. Quantitative results are obtained by comparing the peak heights with an internal PCR calibration standard present in every PCR well at 500 molecules per well. Calibration methods are commonly owned and disclosed in U.S. Provisional Patent Application Ser. No. 60/545,425.

Example 5

De Novo Determination of Base Composition of Amplification Products Using Molecular Mass Modified Deoxynucleotide Triphosphates Because the molecular masses of the four natural nucleobases have a relatively narrow molecular mass range (A=313.058, G=329.052, C=289.046, T=304.046—See Table 2), a persistent source of ambiguity in assignment of base composition can occur as follows: two nucleic acid strands having different base composition may have a difference of about 1 Da when the base composition difference between the two strands is G↔A (−15.994) combined with C↔T (+15.000). For example, one 99-mer nucleic acid strand having a base composition of $A_{27}G_{30}C_{21}T_{21}$ has a theoretical molecular mass of 30779.058 while another 99-mer nucleic acid strand having a base composition of $A_{26}G_{31}C_{22}T_{20}$ has a theoretical molecular mass of 30780.052. A 1 Da difference in molecular mass may be within the experimental error of a molecular mass measurement and thus, the relatively narrow molecular mass range of the four natural nucleobases imposes an uncertainty factor.

The present invention provides for a means for removing this theoretical 1 Da uncertainty factor through amplification of a nucleic acid with one mass-tagged nucleobase and three natural nucleobases. The term "nucleobase" as used herein is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

Addition of significant mass to one of the 4 nucleobases (dNTPs) in an amplification reaction, or in the primers themselves, will result in a significant difference in mass of the resulting amplification product (significantly greater than 1 Da) arising from ambiguities arising from the G↔A combined with C↔T event (Table 2). Thus, the same the G↔A (−15.994) event combined with 5-Iodo-C↔T (−110.900) event would result in a molecular mass difference of 126.894. If the molecular mass of the base composition $A_{27}G_{30}$ 5-Iodo-$C_{21}T_{21}$ (33422.958) is compared with $A_{26}G_{31}$5-Iodo-$C_{22}T_{20}$, (33549.852) the theoretica molecular mass difference is +126.894. The experimental error of a molecular mass measurement is not significant with regard to this molecular mass difference. Furthermore, the only base composition consistent with a measured molecular mass of the 99-mer nucleic acid is $A_{27}G_{30}$5-Iodo-$C_{21}T_{21}$. In contrast, the analogous amplification without the mass tag has 18 possible base compositions.

TABLE 2

Molecular Masses of Natural Nucleobases and the Mass-Modified Nucleobase 5-Iodo-C and Molecular Mass Differences Resulting from Transitions

| Nucleobase | Molecular Mass | Transition | Δ Molecular Mass |
|---|---|---|---|
| A | 313.058 | A-->T | −9.012 |
| A | 313.058 | A-->C | −24.012 |
| A | 313.058 | A-->5-Iodo-C | 101.888 |
| A | 313.058 | A-->G | 15.994 |
| T | 304.046 | T-->A | 9.012 |
| T | 304.046 | T-->C | −15.000 |
| T | 304.046 | T-->5-Iodo-C | 110.900 |
| T | 304.046 | T-->G | 25.006 |
| C | 289.046 | C-->A | 24.012 |
| C | 289.046 | C-->T | 15.000 |
| C | 289.046 | C-->G | 40.006 |
| 5-Iodo-C | 414.946 | 5-Iodo-C-->A | −101.888 |
| 5-Iodo-C | 414.946 | 5-Iodo-C-->T | −110.900 |
| 5-Iodo-C | 414.946 | 5-Iodo-C-->G | −85.894 |
| G | 329.052 | G-->A | −15.994 |
| G | 329.052 | G-->T | −25.006 |
| G | 329.052 | G-->C | −40.006 |
| G | 329.052 | G-->5-Iodo-C | 85.894 |

Example 6

Data Processing

Mass spectra of bioagent identifying amplicons are analyzed independently using a maximum-likelihood processor, such as is widely used in radar signal processing. This processor, referred to as GenX, first makes maximum likelihood estimates of the input to the mass spectrometer for each primer by running matched filters for each base composition aggregate on the input data. This includes the GenX response to a calibrant for each primer.

The algorithm emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bacterial bioagents and includes threat organisms as well as benign background organisms. The latter is used to estimate and subtract the spectral signature produced by the background organisms. A maximum likelihood detection of known background organisms is implemented using matched filters and a running-sum estimate of the noise covariance. Background signal strengths are estimated and used along with the matched filters to form signatures which are then subtracted. The maximum likelihood process is applied to this "cleaned up" data in a similar manner employing matched filters for the organisms and a running-sum estimate of the noise-covariance for the cleaned up data.

The amplitudes of all base compositions of bioagent identifying amplicons for each primer are calibrated and a final maximum likelihood amplitude estimate per organism is made based upon the multiple single primer estimates. Models of all system noise are factored into this two-stage maximum likelihood calculation. The processor reports the number of molecules of each base composition contained in the spectra. The quantity of amplification product corresponding to the appropriate primer set is reported as well as the quantities of primers remaining upon completion of the amplification reaction.

Example 7

Alignment of Alphavirus Sequences Using an nsP1 Primer Pair

A total of 42 alphavirus sequences, including two strains of EEEV, 20 strains of VEEV, one strain of Chikungnya virus, one strain of Igbo Ora virus, two strains of O'nyong-nyong virus, one strain of Ross River virus, one strain of Sagiyama virus, one strain of Mayaro virus, one strain of Barmah forest virus, two strains of Semliki forest virus, one strain of aura virus, one strain of Ockelbo virus, and seven strains of Sindbois virus were aligned and evaluated for identification of useful priming regions. In a representative example, with reference to the reference sequence NC_001449 (SEQ ID NO: 1) representing the genome of Venezualan equine encephalitis virus (VEEV), a pair of primers (no. 316—SEQ ID NOs: 9:54) was designed to produce an alphavirus identifying amplicon 86 nucleobases long corresponding to positions 162-247 of the nsP1 gene of VEEV. This pair of primers is expected to produce an alphavirus identifying amplicon that can provide the means to identify the virus strains described above.

Figure 3:
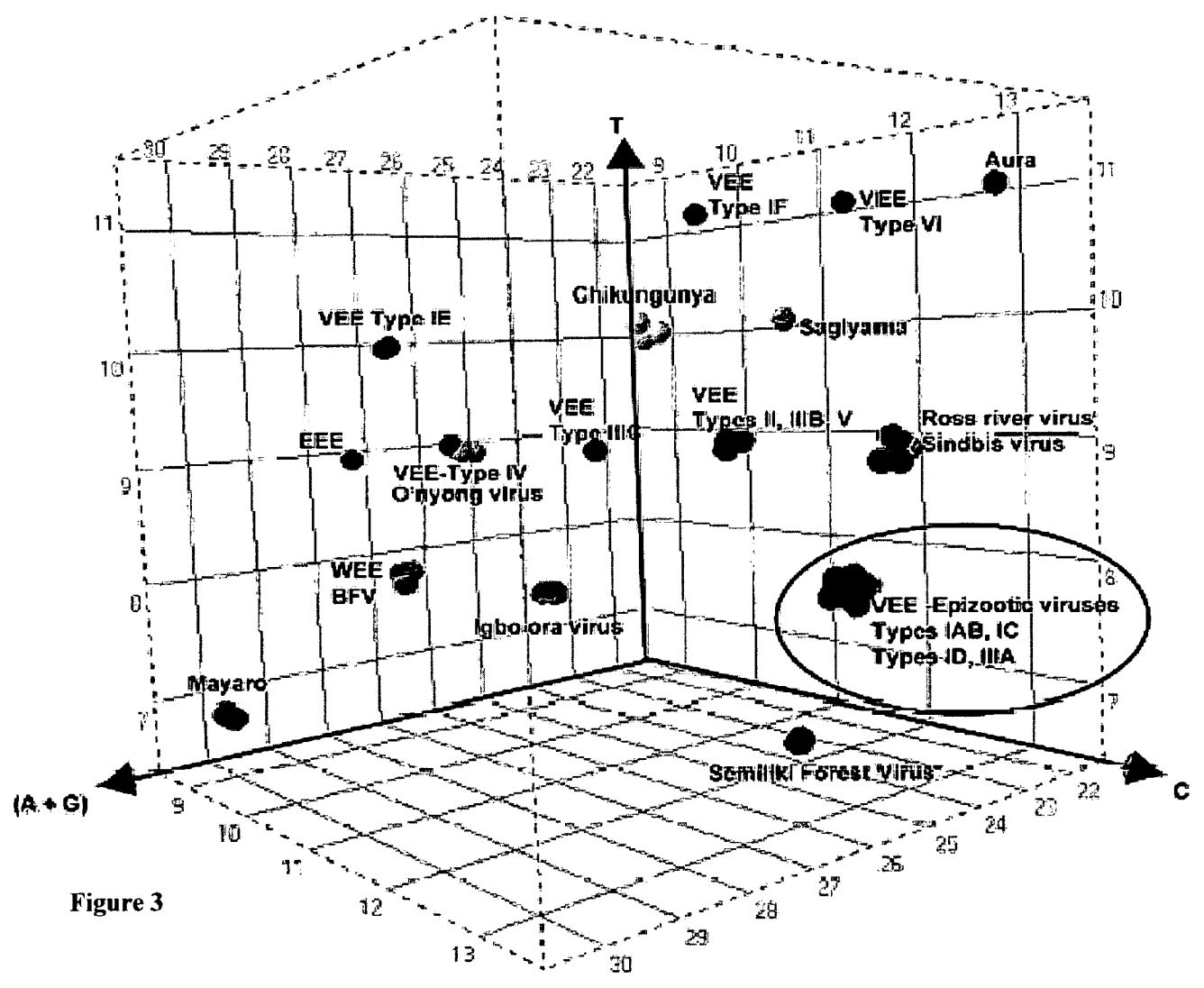

As shown in FIG. 3, in a pseudo four-dimensional plot of expected base compositions of alphavirus identifying amplicons arising from amplification with primer pair no: 316 the epidemic, epizootic VEEV viruses of classes IAB-IC, ID and IIIA (which have the potential to cause severe disease in humans and animals) can be distinguished from the enzootic VEE types IE, IF, I, IIIB, IIIC, IV, V, and VI, which, in turn, are generally distinguishable from each other.

Table 3 lists the results of base composition analysis of nine laboratory test isolates of alphaviruses obtained according to the methods described herein by amplification with primer pair 316 to obtain alphavirus identifying amplicons.

TABLE 3

Expected and Observed Base Compositions of Alphavirus Identifying Amplicons Produced with Primer Pair No: 316 (SEQ ID NOs: 9:54)

| Virus | Strain | Sequence Available | Expected Base Composition [A G C T] | Observed Base Composition [A G C T] |
|---|---|---|---|---|
| VEE | 3908 (subtype IC, 1995) | Yes | [21 23 23 19] | [21 23 23 19] |
| VEE | 66637 (subtype ID, 1981) | Yes | [21 23 23 19] | [21 23 23 19] |
| VEE | 68U201 (Subtype 1E, 1968) | Yes | [22 25 19 20] | [22 25 19 20] |
| VEE | 243937 (subtype 1C, 1992) | Yes | [21 23 23 19] | [21 23 23 19] |
| WEE | OR71 (71V1658) | Yes | [22 26 19 19] | [22 26 19 19] |
| WEE | SD83 (R43738) | No | — | [22 26 19 19] |
| WEE | ON41 (McMillan) | No | — | [22 27 18 19] |
| WEE | Fleming (Fleming) | No | — | [22 25 19 20] |
| EEE | (Parker Strain) | Yes | [23 25 19 19] | [23 25 19 19] |

Example 8

Identification of Six Alphavirus Strains

Two primers pairs (numbers 966 and 1131) which each amplify a sequence of the alphavirus gene nsP1 were tested for their ability to detect and differentiate among eight different known alphavirus strains using the methods described herein. The strains included in the study were the North American strain of Eastern equine encephalitis virus and the Tonate CaAn 410d, 78V3531, AG80-663, Cabassou CaAr 508 and Everglades Fe3-7c strains of Venezuelan equine encephalitis virus. RT-PCR reactions were spiked with either 10-fold or 100-fold dilutions of virus stock and performed according to the method described in Example 2. Each reaction also contained 500 RNA copies of a calibration sequence to quantitate the amount of virus present in each reaction. The calibration sequence is contained within a combination calibration polynucleotide designated RT-PCR calibrant pVIR001 (SEQ ID NO: 92). This calibration sequence was designed with reference to Venezuelan equine encephalitis virus (VEE) strain 3908, subtype IC (GenBank gi number 20800454) such that all primers disclosed herein with the exception of primer pair numbers 2050-2055, hybridize to the calibration sequence and produce alphavirus calibration amplicons that are distinguishable from alphavirus identifying amplicons. Mass spectral analysis of the alphavirus bioagent identifying amplicons resulted in the correct identification of all six alphavirus strains.

Example 9

Identification of Related Alphavirus Species

A series of eight strains of alphaviruses whose alphavirus identifying amplicon sequences (from primer pairs 966 and 1131) are unknown were analyzed using primer pairs 966 and 1131 by the methods described herein. These experiments were carried out without the presence of a calibrant. A representative set of results is shown in Table 4 where it is indicated that the "unknown" alphavirus strains can be assigned to related "known" strains.

TABLE 4

Representative Result Set of Identification of Alphaviruses with Primer Pair
Nos: 966 (SEQ ID NOs: 21:66) and 1131 (SEQ ID NOs: 33:78)

| Sample | Spiked Virus | Primer Pair No: | Base Composition [A G C T] | Match Type | Alphavirus Strain Matched |
|---|---|---|---|---|---|
| 1 | Sindbis Virus | 966 | [24 25 26 23] | exact | Sindbis virus (NoStrain_14_1, genome strain) |
| 1 | Sindbis Virus | 1131 | [29 26 27 23] | exact | Sindbis virus (DI-2, NoStrain_14_1, genome strain) |
| 2 | Nduma Virus | 966 | [26 27 22 23] | exact | Eastern equine encephalitis virus (North American) |
| 2 | Nduma Virus | 1131 | ND | | |
| 3 | Middleburg Virus | 966 | [26 27 22 23] | exact | Eastern equine encephalitis virus (North American) |
| 3 | Middleburg Virus | 1131 | [28 29 27 20] | | Deconvolved BC (none) |
| 4 | Mayaro Virus | 966 | [31 24 22 21] | | Mayaro virus (NoStrain_5_1, NoStrain_6_2) |
| 4 | Mayaro Virus | 1131 | [26 30 26 23] | mass adjust +−1 | Venezuelan equine encephalitis virus (78V3531) |
| 5 | Highlands J Virus | 966 | [28 28 22 20] | no match | Deconvolved BC (none) |
| 5 | Highlands J Virus | 1131 | [28 31 28 18] | cloud offset [−1 0 0 1] | Venezuelan equine encephalitis virus (243937, 3908, 6119, 66457, 66637, 71-180; 600035-71-180/4, 83U434, P676, PMCHo5, SH3, TC-83, Trinidad donkey, V198, ZPC738) |
| 6 | Getah Virus | 966 | [25 24 26 23] | cloud offset [−1 0 0 1] | Sindbis virus (NoStrain_14_1, genome strain) |
| 6 | Getah Virus | 1131 | ND | | |
| 1 | Barmah Virus | 966 | [30 23 23 22] | exact | Barmah Forest virus (BH2193) |
| 1 | Barmah Virus | 1131 | [25 27 30 22] | no match | Deconvolved BC (none) |
| 2 | Semliki Virus | 966 | [28 23 26 21] | exact | Semliki forest virus (A7-74, DI-19, DI-6, Defective RNA particle, L10, genome strain) |
| 2 | Semliki Virus | 1131 | ND | | |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, internet web sites, and the like) cited in the present application is incorporated herein by reference in its entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed is:

1. A composition comprising a purified oligonucleotide primer pair configured to generate amplicons from two or more members of the alphavirus genus by hybridizing a forward primer and a reverse primer to conserved regions of a nsP1 encoding gene in two or more members of said alphavirus genus, said primer pair comprising a forward primer with 100% sequence identity with SEQ ID NO: 93 and a reverse primer with 100% sequence identity with SEQ ID NO: 66.

2. The composition of claim 1 wherein either or both of said oligonucleotide primers comprises at least one modified nucleobase.

3. The composition of claim 1 wherein either or both of said oligonucleotide primers comprises a non-templated T residue on the 5' end.

4. The composition of claim 1 wherein either or both of said oligonucleotide primers comprises at least one non-template tag.

5. The composition of claim 1 wherein either or both of said oligonucleotide primers comprises at least one molecular mass modifying tag.

6. A kit comprising the composition of claim 1.

7. The kit of claim 6 further comprising at least one calibration polynucleotide.

8. The kit of claim 6 further comprising at least one ion exchange resin linked to magnetic beads.

9. A composition comprising a purified oligonucleotide primer pair configured to generate amplicons from two or more members of the alphavirus genus by hybridizing a forward primer and a reverse primer to conserved regions of a nsP1 encoding gene in two or more members of said alphavirus genus, said primer pair comprising a forward primer with 100% sequence identity with SEQ ID NO: 21 and a reverse primer with 100% sequence identity with SEQ ID NO: 66.

10. A method for generating alphavirus amplicons comprising:
1) providing a composition according to claim 1; and
2) contacting an alphavirus nucleic acid with the composition to generate alphavirus amplicons.

* * * * *